US010711315B2

(12) United States Patent
Von Der Mülbe et al.

(10) Patent No.: US 10,711,315 B2
(45) Date of Patent: Jul. 14, 2020

(54) METHOD FOR PRODUCING RNA

(71) Applicant: CureVac Real Estate GmbH, Tübingen (DE)

(72) Inventors: Florian Von Der Mülbe, Stuttgart (DE); Ladislaus Reidel, Rottennburg am Neckar (DE); Thomas Ketterer, Gomaringen (DE); Lilia Gontcharova, Reutlingen (DE); Susanne Bauer, Bodelshausen (DE); Steve Pascolo, Zurich (CH); Jochen Probst, Wolfschlugen (DE); Andreas Schmid, Sigmaringen (DE)

(73) Assignee: CureVac Real Estate GmbH, Tübingen (DE)

( * ) Notice: Subject to any disclaimer, the term of this patent is extended or adjusted under 35 U.S.C. 154(b) by 0 days.

(21) Appl. No.: 16/005,131

(22) Filed: Jun. 11, 2018

(65) Prior Publication Data
US 2018/0282790 A1    Oct. 4, 2018

Related U.S. Application Data

(63) Continuation of application No. 15/044,094, filed on Feb. 15, 2016, now Pat. No. 10,017,826, which is a continuation of application No. PCT/EP2015/000959, filed on May 8, 2015.

(51) Int. Cl.
*C12P 19/34* (2006.01)
*C12N 15/10* (2006.01)
*C12Q 1/689* (2018.01)

(52) U.S. Cl.
CPC ......... *C12Q 1/689* (2013.01); *C12N 15/1003* (2013.01); *C12P 19/34* (2013.01); *C12Q 2600/158* (2013.01)

(58) Field of Classification Search
CPC .............................. C12N 15/1003; C12P 19/34
See application file for complete search history.

(56) References Cited

U.S. PATENT DOCUMENTS

| | | | |
|---|---|---|---|
| 4,839,295 A | 6/1989 | Smith | |
| 5,057,426 A | 10/1991 | Henco et al. | |
| 5,298,392 A | 3/1994 | Atlas et al. | |
| 5,447,922 A | 9/1995 | Lawrence et al. | |
| 5,700,667 A | 12/1997 | Marble et al. | |
| 5,786,464 A | 7/1998 | Seed | |
| 6,114,148 A | 9/2000 | Seed | |
| 6,586,218 B2 | 7/2003 | Milburn et al. | |
| 6,773,885 B1 | 8/2004 | Walder et al. | |
| 6,794,140 B1 | 9/2004 | Goldsborough | |
| 6,989,442 B2 | 1/2006 | Vargeese | |
| 8,217,016 B2 | 7/2012 | Hoerr et al. | |
| 8,383,340 B2 | 2/2013 | Ketterer et al. | |
| 8,859,229 B2 | 10/2014 | Rabinovich et al. | |
| 8,859,275 B2 | 10/2014 | Notka et al. | |
| 2002/0102563 A1 | 8/2002 | Gjerde et al. | |
| 2005/0011836 A1 | 1/2005 | Bidlingmeyer et al. | |
| 2005/0215777 A1 | 9/2005 | Vargeese et al. | |
| 2008/0033158 A1 | 2/2008 | Ngo et al. | |
| 2008/0260706 A1 | 10/2008 | Rabinovish et al. | |
| 2010/0048883 A1 | 2/2010 | Ketterer et al. | |
| 2010/0189729 A1 | 7/2010 | Hoerr et al. | |
| 2010/0203076 A1 | 8/2010 | Fotin-Mleczek et al. | |
| 2011/0104693 A1 | 5/2011 | Seligmann | |
| 2011/0111975 A1 | 5/2011 | Schneider et al. | |
| 2015/0064725 A1 | 3/2015 | Schrum et al. | |
| 2015/0157565 A1 | 6/2015 | Heartlein | |
| 2015/0366997 A1 | 12/2015 | Guild et al. | |
| 2016/0001731 A1 | 1/2016 | Spivak et al. | |
| 2016/0017313 A1 | 1/2016 | Spivak et al. | |
| 2016/0024139 A1 | 1/2016 | Berlanda Scorza et al. | |
| 2016/0024492 A1 | 1/2016 | Issa et al. | |
| 2016/0024547 A1 | 1/2016 | Bancel et al. | |
| 2016/0031981 A1 | 2/2016 | Heartlein et al. | |
| 2016/0032273 A1 | 2/2016 | Shahrokh et al. | |
| 2016/0040154 A1 | 2/2016 | Heartlein et al. | |

FOREIGN PATENT DOCUMENTS

| | | |
|---|---|---|
| CA | 2468048 | 8/1995 |
| DE | 102006061015 | 6/2008 |
| JP | 8073477 | 3/1996 |
| WO | WO 1995/08626 | 3/1995 |
| WO | WO 2001/46687 | 6/2001 |
| WO | WO 2004/022574 | 3/2004 |
| WO | WO 2005/058933 | 6/2005 |

(Continued)

OTHER PUBLICATIONS

Martins, R. et al., Ribonucleic acid purification, J. Chromatogr. A, vol. 1355, pp. 1-14 (Year: 2014).*
Anderson et al., "HPLC purification of RNA for crystallography and NMR", RNA, 2(2): 110-117, 1996.
Azarani and Hecker, "RNA of chromatography under thermally denaturing conditions: analysis and quality determination of RNA," *Transgenomic*, Application Note 116, 2000.
Azarani et al., "RNA analysis by ion-pair reversed-phase high performance liquid chromatography", *Nucleic Acids Research*, 29(2): E7, 2001.
Bryant and Manning, "Isolation of mRNA by affinity chromatography," *The Nucleic Acid Protocols Handbook*, 2: 9-11, 2000.
Chaudhari et al., "A review on good manufacturing practice (GMP) for medicinal products", PharmaTutor, 2(9): 8-19, 2014.

(Continued)

*Primary Examiner* — Teresa E Strzelecka
(74) *Attorney, Agent, or Firm* — Parker Highlander PLLC

(57) ABSTRACT

The present invention relates to a method for producing RNA. In particular, the present invention relates to a method for producing RNA, which is scalable and provides RNA at a high purity. The present invention provides a method for producing RNA under GMP and/or cGMP-compliant conditions. The invention further provides specific processes for use as a quality control in the manufacturing of a template DNA and/or in a method for producing RNA, in particular by in vitro transcription.

16 Claims, 18 Drawing Sheets

Specification includes a Sequence Listing.

(56) References Cited

FOREIGN PATENT DOCUMENTS

| WO | WO 2006/004648 | 1/2006 |
|---|---|---|
| WO | WO 2008/097926 | 8/2008 |
| WO | WO 2012/077080 | 6/2012 |
| WO | WO 2014/140211 | 9/2014 |
| WO | WO 2014/144039 | 9/2014 |
| WO | WO 2014/144711 | 9/2014 |
| WO | WO 2014/144767 | 9/2014 |
| WO | WO 2014/152027 | 9/2014 |
| WO | WO 2014/152030 | 9/2014 |
| WO | WO 2014/152031 | 9/2014 |
| WO | WO 2014/152966 | 9/2014 |
| WO | WO 2014/160243 | 10/2014 |
| WO | WO 2015/052133 | 4/2015 |
| WO | WO 2015/164773 | 10/2015 |

OTHER PUBLICATIONS

Chem et al., "Comparison of quantitative PCR assays for *Escherichia coli* targeting ribosomal RNA and single copy genes", *Lett. Appl. Microbiol.*, 52:298-306, 2011.
Crain, "Preparation and enzymatic hydrolysis of DNA and RNA for mass spectrometry," *Nucleic Acid Constituents*, 193:782-790, 1990.
Dickman et al., "Enrichment and analysis of RNA centered on Ion Pair Reverse Phase Methodology", *RNA*, 12(4): 691-696, 2006.
Edelmann et al., "Production of pure and functional RNA for in vitro reconstitution experiments", *Methods*, 65:333-341, 2014.
Fernandez et al., "Cross flow filtration of RNA extracts by hollow fiber membrane," *Acta Biotechnol.*, 12:49-56, 1992.
Georgopoulos et al., "Use of high-performance liquid chromatographic fractionation of large RNA molecules in the assay of group 1 intron ribozyme activity", *J Chromatogr A.*, 868(1): 109-114, 2000.
Hashimoto, "Macroporous synthetic hydrophilic resin-based packings for the separation of biopolymers", *J Chromatogr.*, 544: 249-244, 1991.
International Search Report and Written Opinion issued in International Application No. PCT/EP2015/000959, dated Sep. 15, 2015.
International Search Report and Written Opinion issued in International Application No. PCT/EP2015/001164, dated Sep. 22, 2015.
Kallen et al., "A development that may evolve into a revolution in medicine: mRNA as the basis for novel, nucleotide-based vaccines and drugs", *Ther Adv Vaccines*, 2(1): 10-31, 2014.
Kern et al., "Application of solution equilibrium analysis to in vitro RNA transcription", *Biotechnology Progress*, 13(6): 747-756, 1997.
Kowalak et al., "A novel method for the determination of post-transcriptional modification in RNA by mass spectrometry," *Nucleic Acids Research*, 21(19):4577-4585, 1993.
Lajmi et al., "Membrane purification of an antisense oligonucleotide," *Org. Process Res. Dev.*, 8(4):651-657, 2004.
Liu and Price, "In vitro transcription on DNA templates immobilitzed to streptavidin magnesphere® paramagnetic particles," *Promega Notes*, 64:21, 1997.
McFarland et al., "Separation of oligo-RNA by reverse-phase HPLC", *Nucleic Acids Res.*, 7(4): 1067-1080, 1979.
Meng and Limbach, "Mass spectrometry of RNA: linking the genome to the proteome," *Brief Funct Genomic Proteomic*, 5(1):87-95, 2006.

Mitra, "Using analytical ultracentrifugation (AUC) to measure global conformational changes accompanying equilibrium tertiary folding of RNA molecules," *Methods in Enzymology*, 469:209-236, 2009.
Parkhomchuk et al., "Transcriptome analysis by strand-specific sequencing of complementary DNA," *Nucleic Acids Research*, 37(18):e123, 2009.
Pascolo, "Messenger RNA-based vaccines," *Expert Opin. Biol. Ther.*, 4(8):1285-1294, 2004.
Pascolo, "RNA-based therapies," *Drug Discovery Handbook*, Chapter 27, pp. 1259-1308, 2005.
Pascolo, "Vaccination with messenger RNA (mRNA)", *Toll-Like Receptors (TLRs) and Innate Immunity, Handbook of Experimental Pharmacology 183*, Bauer and Hartmann ed., Springer-Verlag, 2008.
Pascolo, "Vaccination with messenger RNA," *Methods in Molecular Medicine*, 127:23-40, 2006.
Pascolo, "Vaccination with messenger RNA", *Methods in Molecular Medicine, vol. 127: DNA Vaccines: Methods and Protocols*, 2$^{nd}$ Ed., Saltzman et al. ed., Humana Press, 2006.
Petro et al., "Molded continuous poly(styrene-co-divinylbenzene) rod as a separation medium for the very separation ofpolymers. Comparison of the chromatographic properties of the monolithic rod with columns packed with porous and non-porous beads in high-performance liquid chromatography of polystyrenes ", *J Chromatogr A.*, 752(1-2): 59-66, 1996. (abstract only).
Pomerantz and McCloskey, "Analysis of RNA hydrolyzates by liquid chromatography-mass spectrometry," *Methods in Enzymology*, 193:796-824, 1990.
Sahin et al., "mRNA-based therapeutics—developing a new class of drugs", *Nature Reviews Drug Discovery*, 13(10): 759-780, 2014.
Schlake et al., "Developing mRNA-vaccine technologies", *RNA Biology*, 9(11): 1319-1330, 2012.
Smith et al., "Fast and Accurate Method for Quantitating *E coli* Host-Cell DNA Contamination in Plasmid DNA Preparations", *Biotechniques*, 26:518-526, 1999.
Sobczak and Krzyzosiak, "RNA structure analysis assisted by capillary electrophoresis," *Nucleic Acids Research*, 30(22):e124, 2002.
Stadler et al., "Plasmid DNA purification", J. Gene Med., 6:S54-S66, 2004.
Williams and Lee, "Field-flow fractionation of proteins, polysaccharides, synthetic polymers, and supramolecular assemblies," *J. Sep. Sci.*, 29:1720-1732, 2006.
Wincott et al., "Synthesis, deprotection, analysis and purification of RNA and ribozymes", *Nucleic Acids Res.*, 23(14): 2677, 1995.
Zhao et al., "Multiple injections of electroporated autologous T cells expressing a chimeric antigen receptor mediate regression of human disseminated tumor," *Cancer Res.*, 70(22):9053-9061, 2010.
Zhao et al., "Multiple injections of electroporated autologous T cells expressing a chimeric antigen receptor mediate regression of human disseminated tumor," Supplementary Methods, *Cancer Res.*, 70(22):9053-9061, 2010.
Zou et al., "Engineered RNase P ribozymes are efficient in cleaving a human cytomegalovirus mRNA in vitro and are effective in inhibiting viral gene expression and growth in human cells", *J. of Biological Chemistry*, 278(39): 37265, 2003.

* cited by examiner

T7
TAATACGACTCACTATAGGGAGA

SP6
ATTTAGGTGACACTATAGAAGNG

T3
AATTAACCCTCACTAAAGGGAGA

Fig. 2

```
>P0624_DNA
CAGCTGCATTAATGAATCGGCCAACGCGCGGGGAGAGGCGGTTTGCGTAT
TGGGCGCTCTTCCGCTTCCTCGCTCACTGACTCGCTGCGCTCGGTCGTTC
GGCTGCGGCGAGCGGTATCAGCTCACTCAAAGGCGGTAATACGGTTATCC
ACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGG
CGAAACCCGACAGGACTATAAAGATACCAGGCGTTTCCCCCTGGAAGCTC
CCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGG
TATCTCAGTTCGGTGTAGGTCGTTCGCTCCAAGCTGGGCTGTGTGCACGA
ACCCCCCGTTCAGCCCGACCGCTGCGCCTTATCCGGTAACTATCGTCTTG
AGTCCAACCCGGTAAGACACGACTTATCGCCACTGGCAGCAGCCACTGGT
AACAGGATTAGCAGAGCGAGGTATGTAGGCGGTGCTACAGAGTTCTTGAA
GTGGTGGCCTAACTACGGCTACACTAGAAGAACAGTATTTGGTATCTGCG
CTCTGCTGAAGCCAGTTACCTTCGGAAAAAGAGTTGGTAGCTCTTGATCC
GGCAAACAAACCACCGCTGGTAGCGGTGGTTTTTTTGTTTGCAAGCAGCA
GATTACGCGCAGAAAAAAAGGATCTCAAGAAGATCCTTTGATCTTTTCTA
CGGGGTCTGACGCTCAGTGGAACGAAAACTCACGTTAAGGGATTTTGGTC
ATGAGATTATCAAAAGGATCTTCACCTAGATCCTTTTAAATTAAAAATG
AAGTTTTAAATCAATCTAAAGTATATATGAGTAAACTTGGTCTGACAGTT
ACCAATGCTTAATCAGTGAGGCACCTATCTCAGCGATCTGTCTATTTCGT
TCATCCATAGTTGCCTGACTCCCCGTCGTGTAGATAACTACGATACGGGA
GGGCTTACCATCTGGCCCCAGTGCTGCAATGATACCGCGAGACCCACGCT
CACCGGCTCCAGATTTATCAGCAATAAACCAGCCAGCCGGAAGGGCCGAG
CGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACG
TTGTTGCCATTGCTACAGGCATCGTGGTGTCACGCTCGTCGTTTGGTATG
GCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCA
GAAGTAAGTTGGCCGCAGTGTTATCACTCATGGTTATGGCAGCACTGCAT
AATTCTCTTACTGTCATGCCATCCGTAAGATGCTTTTCTGTGACTGGTGA
GTACTCAACCAAGTCATTCTGAGAATAGTGTATGCGGCGACCGAGTTGCT
CTTGCCCGGCGTCAATACGGGATAATACCGCGCCACATAGCAGAACTTTA
AAAGTGCTCATCATTGGAAAACGTTCTTCGGGGCGAAAACTCTCAAGGAT
CTTACCGCTGTTGAGATCCAGTTCGATGTAACCCACTCGTGCACCCAACT
GATCTTCAGCATCTTTTACTTTCACCAGCGTTTCTGGGTGAGCAAAAACA
GGAAGGCAAAATGCCGCAAAAAGGGAATAAGGGCGACACGGAAATGTTG
AATACTCATACTCTTCCTTTTTCAATATTATTGAAGCATTTATCAGGGTT
ATTGTCTCATGAGCGGATACATATTTGAATGTATTTAGAAAAATAAACAA
ATAGGGGTTCCGCGCACATTTCCCCGAAAAGTGCCACCTGACGTCTAATA
CGACTCACTATAGGGAGAAAGCTTACCATGTGGGTGCCGGTCGTGTTCCT
GACCCTCAGCGTGACGTGGATCGGCGCCGCGCCCTGATCCTGTCGCGGA
TCGTGGGGGGCTGGGAGTGCGAGAAGCACAGCCAGCCCTGGCAGGTGCTG
```

Fig. 6

```
GTGGCCAGCCGCGGCCGGGCCGTGTGCGGCGGCGTGCTGGTGCACCCCA
GTGGGTGCTGACCGCCGCCCACTGCATCCGGAACAAGAGCGTCATCCTGC
TGGGCCGGCACAGCCTGTTCCACCCCGAGGACACCGGCCAGGTGTTCCAG
GTGAGCCACAGCTTCCCCCACCCCCTGTACGACATGAGCCTCCTGAAGAA
CCGGTTCCTGCGGCCCGGCGACGACAGCAGCCACGACCTGATGCTGCTGC
GGCTGAGCGAGCCCGCCGAGCTGACCGACGCCGTGAAGGTGATGGACCTG
CCGACCCAGGAGCCCGCCCTGGGCACCACCTGCTACGCCAGCGGCTGGGG
GAGCATCGAGCCCGAGGAGTTCCTCACCCCCAAGAAGCTGCAGTGCGTGG
ACCTGCACGTGATCAGCAACGACGTGTGCGCCCAGGTGCACCCCAGAAG
GTGACCAAGTTCATGCTGTGCGCCGGCCGGTGGACCGGCGGCAAGAGCAC
CTGCAGCGGCGACAGCGGCGGCCCCCTGGTCTGCAACGGCGTGCTGCAGG
GCATCACCAGCTGGGGCAGCGAGCCCTGCGCCCTGCCCGAGCGCCCCAGC
CTGTACACCAAGGTGGTGCACTACCGGAAGTGGATCAAGGACACCATCGT
GGCCAACCCGTGACCACTAGTTATAAGACTGACTAGCCCGATGGGCCTCC
CAACGGGCCCTCCTCCCCTCCTTGCACCGAGATTAATAAAAAAAAAAAAA
AAAAAAAAAAAAAAAAAAAAAAAAAAAAAAAAAAAAAAAAAAAAAAAAA
ATGCATCCCCCCCCCCCCCCCCCCCCCCCCCCCCCAAAGGCTCTTTTC
AGAGCCACCAGAATTCGGATACTCTAGACATATGCTTAAG
```

Fig. 6 continued

>R1869_RNA product
GGGAGAAAGCUUACCAUGUGGGUGCCGGUCGUGUUCCUGACCCUCAGCGUGACGUGGAUC
GGCGCCGCGCCCCUGAUCCUGUCGCGGAUCGUGGGGGGCUGGGAGUGCGAGAAGCACAGC
CAGCCCUGGCAGGUGCUGGUGGCCAGCCGCGGCCGGGCCGUGUGCGGCGGCGUGCUGGUG
CACCCCCAGUGGGUGCUGACCGCCGCCCACUGCAUCCGGAACAAGAGCGUCAUCCUGCUG
GGCCGGCACAGCCUGUUCCACCCCGAGGACACCGGCCAGGUGUUCCAGGUGAGCCACAGC
UUCCCCCACCCCCUGUACGACAUGAGCCUCCUGAAGAACCGGUUCCUGCGGCCCGGCGAC
GACAGCAGCCACGACCUGAUGCUGCUGCGGCUGAGCGAGCCCGCCGAGCUGACCGACGCC
GUGAAGGUGAUGGACCUGCCGACCCAGGAGCCCGCCCUGGGCACCACCUGCUACGCCAGC
GGCUGGGGGAGCAUCGAGCCCGAGGAGUUCCUCACCCCCAAGAAGCUGCAGUGCGUGGAC
CUGCACGUGAUCAGCAACGACGUGUGCGCCCAGGUGCACCCCAGAAGGUGACCAAGUUC
AUGCUGUGCGCCGGCCGGUGGACCGGCGGCAAGAGCACCUGCAGCGGCGACAGCGGCGGC
CCCCUGGUCUGCAACGGCGUGCUGCAGGGCAUCACCAGCUGGGGCAGCGAGCCCUGCGCC
CUGCCCGAGCGCCCCAGCCUGUACACCAAGGUGGUGCACUACCGGAAGUGGAUCAAGGAC
ACCAUCGUGGCCAACCCGUGACCACUAGUUAUAAGACUGACUAGCCCGAUGGGCCUCCCA
ACGGGCCCUCCUCCCCUCCUUGCACCGAGAUUAAUAAAAAAAAAAAAAAAAAAAAAAAAA
AAAAAAAAAAAAAAAAAAAAAAAAAAAAAAAAAAAAAAAAAAUGCAUCCCCCCCCCCCCCC
CCCCCCCCCCCCCCAAAGGCUCUUUUCAGAGCCACCAGAAUU

Fig. 7

>HsKLK3(GC) Protein

MWVPVVFLTLSVTWIGAAPLILSRIVGGWECEKHSQPWQVLVASRGRAVCGGVLVHPQWVLTAAHCIRNKSVILLGR
HSLFHPEDTGQVFQVSHSFPHPLYDMSLLKNRFLRPGDDSSHDLMLLRLSEPAELTDAVKVMDLPTQEPALGTTCYA
SGWGSIEPEEFLTPKKLQCVDLHVISNDVCAQVHPQKVTKFMLCAGRWTGGKSTCSGDSGGPLVCNGVLQGITSWGS
EPCALPERPSLYTKVVHYRKWIKDTIVANP

Fig. 8

SEQUENCE LISTING

```
<160> NUMBER OF SEQ ID NOS: 21

<210> SEQ ID NO 1
<211> LENGTH: 3040
<212> TYPE: DNA
<213> ORGANISM: Artificial Sequence
<220> FEATURE:
<223> OTHER INFORMATION: Synthetic oligonucleotide (DNA sequence
      encoding RNA HsKLK3(GC)-muag-A64-N5-C30-histoneSL-N5 (R1869))

<400> SEQUENCE: 1
cagctgcatt aatgaatcgg ccaacgcgcg gggagaggcg gtttgcgtat tgggcgctct      60
tccgcttcct cgctcactga ctcgctgcgc tcggtcgttc ggctgcggcg agcggtatca     120
gctcactcaa aggcggtaat acggttatcc acagaatcag gggataacgc aggaaagaac     180
atgtgagcaa aaggccagca aaaggccagg aaccgtaaaa aggccgcgtt gctggcgttt     240
ttccataggc tccgcccccc tgacgagcat cacaaaaatc gacgctcaag tcagaggtgg     300
cgaaacccga caggactata aagataccag gcgtttcccc ctggaagctc cctcgtgcgc     360
tctcctgttc cgaccctgcc gcttaccgga tacctgtccg cctttctccc ttcgggaagc     420
gtggcgcttt ctcatagctc acgctgtagg tatctcagtt cggtgtaggt cgttcgctcc     480
aagctgggct gtgtgcacga accccccgtt cagcccgacc gctgcgcctt atccggtaac     540
tatcgtcttg agtccaaccc ggtaagacac gacttatcgc cactggcagc agccactggt     600
aacaggatta gcagagcgag gtatgtaggc ggtgctacag agttcttgaa gtggtggcct     660
aactacggct acactagaag aacagtattt ggtatctgcg ctctgctgaa gccagttacc     720
ttcggaaaaa gagttggtag ctcttgatcc ggcaaacaaa ccaccgctgg tagcggtggt     780
tttttgtttt gcaagcagca gattacgcgc agaaaaaaag gatctcaaga agatcctttg     840
atcttttcta cggggtctga cgctcagtgg aacgaaaact cacgttaagg gattttggtc     900
atgagattat caaaaaggat cttcacctag atccttttaa attaaaaatg aagttttaaa     960
tcaatctaaa gtatatatga gtaaacttgg tctgacagtt accaatgctt aatcagtgag    1020
gcacctatct cagcgatctg tctatttcgt tcatccatag ttgcctgact ccccgtcgtg    1080
tagataacta cgatacggga gggcttacca tctggcccca gtgctgcaat gataccgcga    1140
```

```
gacccacgct caccggctcc agatttatca gcaataaacc agccagccgg aagggccgag    1200
cgcagaagtg gtcctgcaac tttatccgcc tccatccagt ctattaattg ttgccgggaa    1260
gctagagtaa gtagttcgcc agttaatagt ttgcgcaacg ttgttgccat tgctacaggc    1320
atcgtggtgt cacgctcgtc gtttggtatg gcttcattca gctccggttc caacgatca     1380 aggcgagtta catgatcccc catgttgtgc aaaaaagcgg ttagctcctt cggtcctccg    1440
atcgttgtca gaagtaagtt ggccgcagtg ttatcactca tggttatggc agcactgcat    1500
aattctctta ctgtcatgcc atccgtaaga tgcttttctg tgactggtga gtactcaacc    1560
aagtcattct gagaatagtg tatgcggcga ccgagttgct cttgcccggc gtcaatacgg    1620
gataataccg cgccacatag cagaacttta aaagtgctca tcattggaaa acgttcttcg    1680
gggcgaaaac tctcaaggat cttaccgctg ttgagatcca gttcgatgta acccactcgt    1740
gcacccaact gatcttcagc atcttttact ttcaccagcg tttctgggtg agcaaaaaca    1800
ggaaggcaaa atgccgcaaa aaagggaata agggcgacac ggaaatgttg aatactcata    1860
ctcttccttt ttcaatatta ttgaagcatt tatcagggtt attgtctcat gagcggatac    1920
atatttgaat gtatttagaa aaataaacaa ataggggttc cgcgcacatt tccccgaaaa    1980
gtgccacctg acgtctaata cgactcacta tagggagaaa gcttaccatg tgggtgccgg    2040
tcgtgttcct gaccctcagc gtgacgtgga tcggcgccgc gcccctgatc ctgtcgcgga    2100
tcgtgggggg ctgggagtgc gagaagcaca gccagccctg gcaggtgctg gtggccagcc    2160
gcggccgggc cgtgtgcggc ggcgtgctgg tgcaccccca gtgggtgctg accgccgccc    2220
actgcatccg gaacaagagc gtcatcctgc tgggccggca cagcctgttc caccccgagg    2280
acaccggcca ggtgttccag gtgagccaca gcttccccca ccccctgtac gacatgagcc    2340
tcctgaagaa ccggttcctg cggcccgcg acgacagcag ccacgacctg atgctgctgc    2400
ggctgagcga gcccgccgag ctgaccgacg ccgtgaaggt gatggacctg ccgacccagg    2460
agcccgccct gggcaccacc tgctacgcca gcggctgggg gagcatcgag cccgaggagt    2520
tcctcacccc caagaagctg cagtgcgtgg acctgcacgt gatcagcaac gacgtgtgcg    2580
cccaggtgca cccccagaag gtgaccaagt tcatgctgtg cgccggccgg tggaccggcg    2640
gcaagagcac ctgcagcggc gacagcggcg gccccctggt ctgcaacggc gtgctgcagg    2700
gcatcaccag ctgggggagc gagccctgcg ccctgcccga gcgccccagc ctgtacacca    2760
aggtggtgca ctaccggaag tggatcaagg acaccatcgt ggccaacccg tgaccactag    2820
ttataagact gactagcccg atgggcctcc aacgggccc tcctcccctc cttgcaccga    2880
gattaataaa aaaaaaaaa aaaaaaaaa aaaaaaaaa aaaaaaaaa aaaaaaaaa         2940 aaaaaaaaaa atgcatcccc cccccccccc cccccccccc cccccccaaa ggctcttttc    3000
agagccacca gaattcggat actctagaca tatgcttaag                          3040
```

<210> SEQ ID NO 2
<211> LENGTH: 1003
<212> TYPE: RNA
<213> ORGANISM: Artificial Sequence
<220> FEATURE:
<223> OTHER INFORMATION: Synthetic oligonucleotide (RNA sequence R1869
      corresponding to SEQ ID NO:1 (HsKLK3(GC)-muag-A64-N5-C30-
      histoneSL-N5))

<400> SEQUENCE: 2

```
gggagaaagc uuaccaugug ggugccgguc guguuccuga cccucagcgu gacguggauc    60
ggcgccgcgc cccugauccu gucgcggauc gugggggggcu gggagugcga gaagcacagc   120
```

```
cagcccuggc aggugcuggu ggccagccgc ggccgggccg ugugcggcgg cgugcugguq      180 caccccccagu gggugcugac cgccgcccac ugcauccgga acaagagcgu cauccugcug     240
ggccggcaca gccuguucca ccccgaggac accggccagg uguuccaggu gagccacagc     300 uuccccccacc cccuguacga caugagccuc cugaagaacc gguuccugcg gcccggcgac    360
gacagcagcc acgaccugau gcugcugcgg cugagcgagc ccgccgagcu gaccgacgcc    420
gugaagguga uggaccugcc gacccaggag cccgcccugg gcaccaccug cuacgccagc    480
ggcuggggga gcaucgagcc cgaggaguuc cucaccccca agaagcugca gugcguggac    540
cugcacguga ucagcaacga cgugugcgcc caggugcacc cccagaaggu gaccaaguuc    600
augcugugcg ccggccggug gaccggcggc aagagcaccu gcagcggcga cagcggcggc    660
cccugguccu gcaacggcgu gcugcagggc aucaccagcu ggggcagcga gcccugcgcc    720
cugcccgagc gccccagccu guacaccaag guggugcacu accggaagug gaucaaggac    780
accaucgugg ccaaccccgug accacuaguu auaagacuga cuagcccgau gggccucccca   840 acgggcccuc cuccccuccu ugcaccgaga uuaauaaaaa aaaaaaaaaa aaaaaaaaaa    900
aaaaaaaaaa aaaaaaaaaa aaaaaaaaaa aaaaaaaaau gcaucccccc ccccccccccc    960 cccccccccc ccccaaagg cucuuuucag agccaccaga auu                       1003
```

<210> SEQ ID NO 3
<211> LENGTH: 261
<212> TYPE: PRT
<213> ORGANISM: Artificial Sequence
<220> FEATURE:
<223> OTHER INFORMATION: Synthetic polypeptide (protein sequence
      corresponding to RNA according to SEQ ID NO:2 (HsKLK3(GC)-muag-
      A64-N5-C30-histoneSL-N5; R1869))

<400> SEQUENCE: 3

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

-continued

```
Thr Lys Phe Met Leu Cys Ala Gly Arg Trp Thr Gly Lys Ser Thr
            195                 200                 205

Cys Ser Gly Asp Ser Gly Pro Leu Val Cys Asn Gly Val Leu Gln
210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
            245                 250                 255

Ile Val Ala Asn Pro
            260

<210> SEQ ID NO 4
<211> LENGTH: 23
<212> TYPE: DNA
<213> ORGANISM: Artificial Sequence
<220> FEATURE:
<223> OTHER INFORMATION: Synthetic T7 RNA polymerase promoter sequence

<400> SEQUENCE: 4
taatacgact cactataggg aga                                          23

<210> SEQ ID NO 5
<211> LENGTH: 23
<212> TYPE: DNA
<213> ORGANISM: Artificial Sequence
<220> FEATURE:
<223> OTHER INFORMATION: Synthetic SP6 RNA polymerase promoter sequence
<220> FEATURE:
<221> NAME/KEY: misc_feature
<222> LOCATION: (22)..(22)
<223> OTHER INFORMATION: n is a, c, g, or t

<400> SEQUENCE: 5
atttaggtga cactatagaa gng                                          23

<210> SEQ ID NO 6
<211> LENGTH: 23
<212> TYPE: DNA
<213> ORGANISM: Artificial Sequence
<220> FEATURE:
<223> OTHER INFORMATION: Synthetic T3 RNA polymerase promoter

<400> SEQUENCE: 6
aattaaccct cactaaaggg aga                                          23

<210> SEQ ID NO 7
<211> LENGTH: 24
<212> TYPE: DNA
<213> ORGANISM: Artificial Sequence
<220> FEATURE:
<223> OTHER INFORMATION: Synthetic M13 universal primer

<400> SEQUENCE: 7
cgccagggtt ttcccagtca cgac                                         24

<210> SEQ ID NO 8
<211> LENGTH: 16
<212> TYPE: DNA
<213> ORGANISM: Artificial Sequence
<220> FEATURE:
<223> OTHER INFORMATION: Synthetic primer EC 679U

<400> SEQUENCE: 8
ggacaaggca ctagcg                                                  16
```

<210> SEQ ID NO 9
<211> LENGTH: 18
<212> TYPE: DNA
<213> ORGANISM: Artificial Sequence
<220> FEATURE:
<223> OTHER INFORMATION: Synthetic primer EC 973 L

<400> SEQUENCE: 9
atgcgaggta cggtagga                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic probe EC1 FL

<400> SEQUENCE: 10
catccggtca gtggcagt                                                 18

<210> SEQ ID NO 11
<211> LENGTH: 19
<212> TYPE: DNA
<213> ORGANISM: Artificial Sequence
<220> FEATURE:
<223> OTHER INFORMATION: Synthetic probe EC1 LC

<400> SEQUENCE: 11
aagggcgaac agttcctga                                                19

<210> SEQ ID NO 12
<211> LENGTH: 17
<212> TYPE: DNA
<213> ORGANISM: Artificial Sequence
<220> FEATURE:
<223> OTHER INFORMATION: Synthetic sense primer bla13U

<400> SEQUENCE: 12
gataccgcga gacccac                                                  17

<210> SEQ ID NO 13
<211> LENGTH: 17
<212> TYPE: DNA
<213> ORGANISM: Artificial Sequence
<220> FEATURE:
<223> OTHER INFORMATION: Synthetic antisense primer bla355L

<400> SEQUENCE: 13
ggaaccggag ctgaatg                                                  17

<210> SEQ ID NO 14
<211> LENGTH: 16
<212> TYPE: DNA
<213> ORGANISM: Artificial Sequence
<220> FEATURE:
<223> OTHER INFORMATION: Synthetic probe BL04FL

<400> SEQUENCE: 14
gccagccgga agggcc                                                   16

<210> SEQ ID NO 15
<211> LENGTH: 19
<212> TYPE: DNA
<213> ORGANISM: Artificial Sequence
<220> FEATURE:
<223> OTHER INFORMATION: Synthetic probe BL04LC

```
<400> SEQUENCE: 15
gcgcagaagt ggtcctgca                                                19

<210> SEQ ID NO 16
<211> LENGTH: 18
<212> TYPE: DNA
<213> ORGANISM: Artificial Sequence
<220> FEATURE:
<223> OTHER INFORMATION: Synthetic forward primer 204-AS-FW

<400> SEQUENCE: 16
cactgcatcc ggaacaag                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic reverse primer 205-AS-RV

<400> SEQUENCE: 17
cacgtcgttg ctgatcac                                                 18

<210> SEQ ID NO 18
<211> LENGTH: 20
<212> TYPE: DNA
<213> ORGANISM: Artificial Sequence
<220> FEATURE:
<223> OTHER INFORMATION: Synthetic forward primer 799-AS-FW

<400> SEQUENCE: 18
ccagaaggtg accaagttca                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic reverse primer 792-AS-RV

<400> SEQUENCE: 19
gctctgaaaa gagcctttgg                                               20

<210> SEQ ID NO 20
<211> LENGTH: 13
<212> TYPE: RNA
<213> ORGANISM: Artificial Sequence
<220> FEATURE:
<223> OTHER INFORMATION: Synthetic oligonucleotide (consensus 'Kozak'
      sequence)

<400> SEQUENCE: 20
gccgccrcca ugg                                                      13

<210> SEQ ID NO 21
<211> LENGTH: 10
<212> TYPE: RNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: n = a or g
```

```
<400> SEQUENCE: 21 ccrnccaugg                                                              10
```

METHOD FOR PRODUCING RNA

This application is a continuation of U.S. application Ser. No. 15/044,094, filed Feb. 15, 2016, which is a continuation of International Application No. PCT/EP2015/000959, filed May 8, 2015, the entirety of each of which is incorporated herein by reference.

The sequence listing that is contained in the file named "CRVCP0176USC1.txt", which is 12 KB (as measured in Microsoft Windows®) and was created on Jun. 11, 2018, is filed herewith by electronic submission and is incorporated by reference herein.

The present invention relates to a method for producing RNA. In particular, the present invention relates to a method for producing RNA, which is scalable and provides RNA at a high purity. The present invention provides a method for producing RNA under GMP and/or cGMP-compliant conditions. The invention further provides specific processes for use as a quality control in the manufacturing of a template DNA and/or in a method for producing RNA, in particular by in vitro transcription.

Molecular medicine aims at curing or preventing numerous diseases by employing various therapeutic approaches, such as gene therapy and genetic vaccination. Such approaches are frequently based on the introduction of nucleic acids, such as DNA or RNA, into a subject's cell or tissue, followed by the translation of the information coded by the nucleic acids into the desired polypeptides or proteins.

Genetic vaccinations, pioneered by injecting naked plasmid DNA, were demonstrated in the early 1990s on mice. However, during clinical trials (phase I/II clinical studies) it became clear that this technology was unable to fulfil the expectations in humans that have been aroused by the studies in mice.

1990 Wolff et al. showed that the injection of naked genetic information in the form of plasmid DNA or mRNA can lead to protein expression in mice (Science. 1990 Mar. 23; 247(4949 Pt 1):1465-8). These results were followed by investigations which showed that naked plasmid DNA can be used for vaccination. The use of mRNA for vaccination, however, was paid little attention until the late 1990s, when it was demonstrated that the transfer of mRNA into dendritic cells triggers immune responses. The direct injection of mRNA for vaccination remained a marginal theme. One of the main reasons for this was the instability of mRNA due to its rapid degradation by ribonucleases and the associated limited effectiveness of the mRNA as a genetic tool in vivo. In the meantime, however, numerous methods for stabilizing mRNA have been described in the prior art, for example in EP-A-1083232, WO 99/14346, U.S. Pat. Nos. 5,580,859 and 6,214,804.

RNA as the nucleic acid for a genetic vehicle has numerous advantages over DNA, including:

i) The RNA introduced into the cell does not integrate into the genome (whereas DNA does integrate into the genome to a certain degree and can also be inserted into an intact gene of the genome of the host cell, causing a mutation of this gene, which can lead to a partial or total loss of the genetic information or to misinformation).

ii) No viral sequences, such as promoters etc., are required for the effective transcription of RNA (whereas a strong promoter (e.g. the viral CMV promoter) is required for the expression of DNA introduced into the cell). The integration of such promoters into the genome of the host cell can lead to undesirable changes in the regulation of gene expression.

iii) The degradation of RNA that has been introduced takes place in a limited period of time, so that it is possible to achieve transient gene expression, which can be discontinued after the required treatment period (whereas this is not possible in the case of DNA that has been integrated into the genome).

iv) RNA does not lead to the induction of pathogenic anti-RNA antibodies in the patient (whereas the induction of anti-DNA antibodies is known to cause an undesirable immune response).

v) RNA is widely applicable; any desired RNA for any desired protein of interest can be prepared in short period of time for therapeutic purposes, even on an individual patient basis (personalized medicine).

In summary, it remains to be emphasized that mRNA represents a transient copy of the coded genetic information in all organisms, serves as a model for the synthesis of proteins and, unlike DNA, represents all the necessary prerequisites for the preparation of a suitable vector for the transfer of exogenous genetic information in vivo.

These beneficial characteristics of mRNA were discovered in the recent years and clinical development of mRNA-based therapeutics is in progress (reviewed in Sahin et al. 2014. Nat Rev Drug Discov. 2014 October; 13(10):759-80. doi: 10.1038/nrd4278. Epub 2014 Sep. 19. And Kallen and Thess 2014. Ther Adv Vaccines. 2014 January; 2(1):10-31. doi: 10.1177/2051013613508729. Review).

By then, the synthesis of in vitro transcribed mRNA at a laboratory scale (up to 1 mg), produced under non-GMP (good manufacturing practice) conditions was the technical standard in the art.

For this reason, several methods for improving the production of in vitro transcribed RNA were developed. Pascolo 2006 (Methods Mol Med. 2006; 127:23-40) and Probst et al. (2012 Messenger RNA Vaccines Gene Vaccines, Springer Vienna, ISBN 978-3-7091-0438-5) describe the principles of the production of pharmaceutical grade mRNA, which is performed in vitro in a reaction termed run-off transcription, where the template plasmid DNA (pDNA) contains an RNA polymerase promoter and all structural mRNA elements (except the 5' Cap and, in some protocols, the 3' poly(A) tail). Purified plasmid DNA is linearized by sequence-specific cleavage with a restriction enzyme to ensure defined termination of transcription and is then used as a DNA template for RNA in vitro transcription. Besides linearized template DNA, the in vitro transcription reaction mixture contains reaction buffer, recombinant RNA polymerase, nucleotides and, in some protocols, Cap analogue. Alternative protocols include a separate enzymatic capping reaction after transcription. Transcription stops as the RNA polymerase reaches the end of the DNA template releasing both the template DNA and the newly synthesized mRNA. Polyadenylation of the mRNA molecule is either encoded on the pDNA by a poly(T) sequence of about 50 nucleotides and added during the in vitro transcription reaction, or by synthesizing the poly-A tail enzymatically in a post-transcriptional step. Finally, different protocols are employed to purify the mRNA product, all of which include a step of nuclease digestion for subsequent removal of template DNA.

Furthermore it was shown that a current good manufacturing practice (cGMP)-compliant chromatographic method increases the activity of introduced mRNA molecules up to about five times (regarding protein expression in vivo) (Probst et al, Gene Ther. 2007 August; 14(15):1175-80. Epub 2007 May 3 and WO2008077592).

Some prior art documents concern specific aspects of the production of in vitro transcribed RNA:

WO2014/152027 describes methods for production of RNA transcripts using a non-amplified, linearized DNA template in an RNA in vitro transcription reaction. These methods include the linearization of plasmid DNA as template for the in vitro transcription reaction, in vitro transcription and several purification steps between the different steps of the method.

WO2014/144039 describes several methods for characterizing samples comprising RNA transcripts including oligonucleotide mapping, reverse transcriptase sequencing, charge distribution analysis, or detection of RNA impurities.

WO2008/077592 discloses a method for purifying large RNA on a preparative scale with ion-pairing reversed phase HPLC using a porous reversed stationary phase. It is reported that a particular advantage of using the specified porous stationary phase is that excessively high pressures can be avoided, facilitating a preparative purification of RNA. However, the method involves the use of harsh organic solvents (e.g. acetonitrile) and high temperatures (78° C.) for the separation column, and a low temperature (12° C.) for the sampler. The nature of the contaminant(s) that can be successfully separated from a desired RNA using the method is not exemplified, including any requirements for preceding steps such as DNase treatment. Additionally, chromatographic separation of RNA based on ion-pairing reversed phase HPLC or ion exchange resin are based on the molecule's total charge and may be effective for purification of RNA molecules of up to about 4,000-5,000 bases.

As illustrated above, RNA is emerging as an innovative candidate for a variety of pharmaceutical applications, but efficient large-scale production, in particular under current good manufacturing practice (cGMP) or GMP compliance, continues to be a challenge.

However, for example, for conducting preclinical and clinical trials and commercialization as human therapeutic, and in order to produce a large amount of RNA, e.g. RNA vaccine in a pandemic scenario, an up-scaled cGMP or GMP-compliant production process needs to be developed and established. Such a process should be capable of producing at least 1 g mRNA, preferably at least 5 g, or more preferably at least 10 g mRNA per batch.

So far, no cGMP or GMP-compliant production process for manufacturing in vitro transcribed RNA at a large scale, including (c)GMP-compliant quality controls, is described in the art. A (c)GMP compliant production process has to ensure the consistent production of a homogeneous ultra-pure (no contaminations from individual production steps, such as template DNA or bacterial DNA), sterile, non-pyrogenic (endotoxin free) and stable mRNA medicament in a highly reproducible manner (that is: no batch-to-batch variability). Effective quality controls are thus required for intermediates in the production process (e.g. plasmid DNA) as well as for the end products (mRNA/formulated mRNA). A (c)GMP-compliant production process is a prerequisite to further establish mRNA as a powerful therapeutic tool in modern molecular medicine. Therefore, there is an urgent need to establish a (c)GMP-compliant mRNA production process.

Moreover, there is an unmet need of an effective method for determining the homogeneity and physical-chemical integrity of RNA transcripts for clinical. Methods for determining the homogeneity and physical-chemical integrity of RNA manufactured for use as a human therapeutic are needed in order to demonstrate consistency of production batches and for maintaining safety and efficacy of the therapeutic product during long-term storage. Furthermore, in order to facilitate industrial applications, the RNA manufacturing process must enable consistent, cost- and time-efficient operation (e.g. quick, easy, reproducible, high yield) on a large scale, preferably in compliance with (c)GMP.

It is one object of the present invention to develop a scalable current good manufacturing practice (c)GMP-compliant production process including appropriate quality controls to produce RNA of a high quality in large quantities. It is further an object of the present invention to provide a scalable method for producing RNA, which preferably allows production of RNA for clinical use, on a large scale. In particular, it is an object of the present invention to provide a method for producing RNA, in particular for producing RNA under (c)GMP compliant conditions, wherein the method is suitable for industrial application. In particular, RNA should be provided without contaminations, such as template DNA or bacterial DNA. A further object underlying the present invention is the provision of a method for determining the quality, especially the homogeneity and/or physical-chemical integrity, of in vitro produced RNA. In particular, it is an object of the present invention to provide a method for controlling the quality of RNA produced in vitro, wherein the method is preferably applicable in a (c)GMP compliant environment.

The problem underlying the present invention is solved by the claimed subject-matter.

The present invention provides a method for producing RNA, particularly an mRNA molecule, suitable for manufacturing clinical-grade RNA of high purity, reproducibly and in compliance with (c)GMP. In particular, the present invention provides a method for producing RNA as defined by the claims and the description herein.

In a particular aspect, the present invention concerns a method for producing RNA comprising the following steps:

a) providing a template DNA comprising a nucleic acid sequence encoding an RNA sequence;

b) in vitro transcription of the template DNA in order to obtain a composition comprising the RNA;

wherein the method comprises at least one step for controlling the quality of the template DNA provided in step a), wherein the at least one step for controlling the quality of the template DNA comprises at least one selected from the group consisting of determining the concentration of the template DNA in a sample, determining the integrity of the template DNA, determining the identity of the template DNA, and determining the purity of the template DNA;

and/or at least one step for controlling the quality of the RNA obtained in step b), wherein the at least one step for controlling the quality of the RNA obtained in step b) comprises at least one step selected from the group consisting of determining the concentration of the RNA in a sample, determining the integrity of the RNA, determining the identity of the RNA, determining the purity of the RNA, determining the pH of a sample comprising the RNA, determining the osmolality of a sample comprising the RNA, determining the presence and/or the amount of the template DNA in a sample comprising the RNA, and determining the presence and/or the amount of an organic solvent in a sample comprising the RNA.

It has surprisingly been found by the inventors that the inventive method, in particular the specific combination of steps as defined herein, is suitable for large-scale production of highly pure RNA, in particular in a GMP or cGMP-compliant manner.

Disclosed herein are methods for production of RNA transcripts, particularly mRNA, useful for manufacturing RNA of excellent purity at a large scale, reproducibly and in compliance with (c)GMP. The major production steps preferably include the provision of a template DNA for in vitro transcription, e.g. by cloning the gene or sequence of interest into an appropriate plasmid DNA vector (see also FIG. 1). In another step, an in vitro transcription reaction is performed using the template DNA, preferably as defined herein, as a template. For example, a plasmid DNA template may be linearized using restriction endonucleases to ensure defined termination of the subsequent run-off in vitro transcription. The template DNA serves as a template for enzymatic RNA in vitro transcription. In certain embodiments, the RNA product is lyophilized and formulated after removal of the template DNA and RNA purification.

An aspect of the present invention relates to at least one purification step, preferably a combination of purification steps, which allows to efficiently remove a starting material or a by-product of any upstream manufacturing processes, including organic solvents, enzymes, bacterial contaminations, DNA contaminations and the like.

Another aspect of the present invention is that along with a defined production step, and/or a defined purification step, quality controls are performed in compliance with a (c)GMP production. Moreover, several quality end-control measurements are preferably performed with the final RNA product to ensure product safety, ensuring a drug-safety-profile of a clinical-grade RNA medicament. These measurements include the detection of potentially hazardous contaminations during the production process (e.g., endotoxin, bacterial DNA, DNA contaminations, bacterial contaminations, contaminations with organic solvents) and the like. Moreover, quality and integrity of intermediates of the method are monitored. In a specific aspect, the invention provides a method for controlling the quality of the RNA product or any intermediate in a process for producing RNA, preferably a process for producing RNA by in vitro transcription. In a particular aspect, the invention provides a method for controlling the quality of a templated DNA used in such a process and/or the quality of an RNA (final product or intermediate) obtained in a process for producing RNA.

The inventive manufacturing process, in particular if including purification steps and quality controls, ensures the production of a homogeneous ultra-pure (no contaminations with product intermediates, enzymes, solvents), sterile, non-pyrogenic (endotoxin free) and stable RNA, e.g. an mRNA medicament, being manufactured in a highly reproducible manner.

The present invention thus represents a milestone to further establish RNA particularly mRNA as an inventive therapeutic tool in modern molecular medicine.

For the sake of clarity and readability, the following definitions are provided. Any technical feature mentioned for these definitions may be read on each and every embodiment of the invention. Additional definitions and explanations may be specifically provided in the context of these embodiments.

Enzyme: Enzymes are catalytically active biomolecules that perform biochemical reactions such as DNA dependent RNA transcription (e.g., RNA polymerases), or double stranded DNA digestion (e.g., restriction endonucleases). Enzymes are typically composed of amino acids and/or RNA (ribozymes, snRNA).

Restriction endonucleases: Restriction endonucleases or restriction enzymes are a class of enzymes that occur naturally in bacteria and in some viruses. Restriction endonucleases can be used in the laboratory to cleave DNA molecules into smaller fragments for molecular cloning and gene characterization. Restriction enzymes bind specifically to and cleave double-stranded DNA at specific sites within or adjacent to a particular sequence known as the recognition site. Most of the restriction enzymes recognize a specific sequence of nucleotides that are four, five or six nucleotides in length and display twofold symmetry. Some cleave both strands exactly at the axis of symmetry, generating fragments of DNA that carry blunt ends; others cleave each strand at similar locations on opposite sides of the axis of symmetry, creating fragments of DNA that carry single-stranded termini (cohesive ends). The restriction endonucleases are categorized into four groups (Types I, II, III, and IV) based on their composition and enzyme cofactor requirements, the nature of their target sequence, and the position of their DNA cleavage site relative to the target sequence. All types of enzymes recognize specific short DNA sequences and carry out the cleavage of DNA, yielding specific fragments with terminal 5'-phosphates. Restriction endonucleases recognize and bind particular sequences of nucleotides (the 'recognition site') on DNA molecules. Once bound, they cleave the molecule within (e.g., BamHI), to one side of (e.g., SapI), or to both sides (e.g., TspRI) of the recognition sequence. Particularly preferred is the use of the following restriction enzymes: BciVI (BfuI), BcuI (SpeI), EcoRI, AatII, AgeI (BshTI), ApaI, BamHI, BglII, BlpI (Bpu1102I), BsrGI (Bsp1407), ClaI (Bsu15I), EcoRI, EcoRV (Eco32I), HindIII, KpnI, MluI, NcoI, NdeI, NheI, NotI, NsiI, Mph1103I), PstI, PvuI, PvuII, SacI, SalI, ScaI, SpeI, XbaI, XhoI, SacII (Cfr42I), XbaI. Restriction enzymes recognize short DNA sequences and cleave double-stranded DNA at specific sites within or adjacent to these sequences. Approximately 3,000 restriction enzymes, recognizing over 230 different DNA sequences, have been discovered. They have been found mostly in bacteria, but have also been isolated from viruses, archaea and eukaryotes. A list of known restriction enzymes can be found at the rebase database:

http://rebase.neb.com/rebase/rebase.html

Restriction site: A restriction site, also termed restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence. Most restriction endonucleases recognize palindromic or partially palindromic sites. A palindrome is defined as dyad symmetry around an axis. For example, EcoRI digestion produces "sticky" ends, whereas SmaI restriction enzyme cleavage produces "blunt" ends. Recognition sequences in DNA differ for each restriction enzyme, producing differences in the length, sequence and strand orientation (5' end or the 3' end) of a sticky-end "overhang" of an enzyme restriction. Different restriction enzymes that recognize the same sequence are known as neoschizomers. These often cleave in different locales of the sequence. Different enzymes that recognize and cleave in the same location are known as isoschizomers.

Protein: A protein typically comprises one or more peptides or polypeptides. A protein is typically folded into 3-dimensional form, which may be required for the protein to exert its biological function. The sequence of a protein or peptide is typically understood to be the order, i.e. the succession of its amino acids.

Recombinant protein: The term 'recombinant protein' refers to proteins that have been produced in a heterologous system, that is, in an organism that naturally does not produce such a protein, or a variant of such a protein. Typically, the heterologous systems used in the art to produce recombinant proteins are bacteria (e.g., *Escherichia coli*), yeast (e.g., *Saccharomyces cerevisiae*) or certain mammalian cell culture lines.

Plasmid DNA (vectors): The term 'plasmid DNA' or 'plasmid DNA vector' refer to a circular nucleic acid molecule, preferably to an artificial nucleic acid molecule. A plasmid DNA in the context of the present invention is suitable for incorporating or harboring a desired nucleic acid sequence, such as a nucleic acid sequence comprising a sequence encoding an RNA and/or an open reading frame encoding at least one peptide or polypeptide. Such plasmid DNA constructs/vectors may be storage vectors, expression vectors, cloning vectors, transfer vectors etc. A storage vector is a vector, which allows the convenient storage of a nucleic acid molecule, for example, of an RNA molecule. Thus, the plasmid DNA may comprise a sequence corresponding (coding for), e.g., to a desired RNA sequence or a part thereof, such as a sequence corresponding to the open reading frame and the 5'- and/or 3'UTR of an mRNA. An expression vector may be used for production of expression products such as RNA, e.g. mRNA in a process called RNA in vitro transcription. For example, an expression vector may comprise sequences needed for RNA in vitro transcription of a sequence stretch of the vector, such as a promoter sequence, e.g. an RNA promoter sequence, preferably T3, T7 or SP6 RNA promotor sequences. A cloning vector is typically a vector that contains a cloning site, which may be used to incorporate nucleic acid sequences (insert) into the vector. A cloning vector may be, e.g., a plasmid vector or a bacteriophage vector. A transfer vector may be a vector, which is suitable for transferring nucleic acid molecules into cells or organisms, for example, viral vectors. Preferably, a plasmid DNA vector in the sense of the present invention comprises a multiple cloning site, an RNA promoter sequence, optionally a selection marker, such as an antibiotic resistance factor, and a sequence suitable for multiplication of the vector, such as an origin of replication. Particularly preferred in the context of the present invention are plasmid DNA vectors, or expression vectors, comprising promoters for DNA-dependent RNA polymerases such as T3, T7 and Sp6. As plasmid backbone, particularly preferred are pUC19 and pBR322.

Template DNA: As used herein, the term 'template DNA' (or 'DNA template') typically relates to a DNA molecule comprising a nucleic acid sequence encoding the RNA sequence to be in vitro transcribed. The template DNA is used as template for in vitro transcription in order to produce the RNA encoded by the template DNA. Therefore, the template DNA comprises all elements necessary for in vitro transcription, particularly a promoter element for binding of a DNA dependent RNA polymerase as e.g. T3, T7 and SP6 RNA polymerases 5' of the DNA sequence encoding the target RNA sequence. Furthermore the template DNA may comprise primer binding sites 5' and/or 3' of the DNA sequence encoding the target RNA sequence to determine the identity of the DNA sequence encoding the target RNA sequence e.g. by PCR or DNA sequencing. As used herein, the term 'template DNA' may also refer to a DNA vector, such as a plasmid DNA, which comprises a nucleic acid sequence encoding the RNA sequence. Further, the 'template DNA' in the context of the present invention may be a linear or a circular DNA molecule.

Target Sequence: A 'target sequence' as used herein is typically understood as the sequence of the RNA, which is encoded by the nucleic acid sequence comprised in the template DNA. The target sequence is thus the sequence to be synthesized by in vitro transcription, e.g. a protein-coding sequence or another RNA as defined herein like isRNA, antisense RNA etc.

Linear template DNA plasmid: The linear template DNA plasmid is obtained by contacting the plasmid DNA with a restriction enzyme under suitable conditions so that the restriction enzyme cuts the plasmid DNA at its recognition site(s) and disrupts the plasmid structure. Hence, the linear template DNA comprises a free 5' end and a free 3' end, which are not linked to each other. If the plasmid DNA contains only one recognition site for the restriction enzyme, the linear template DNA has the same number of nucleotides as the plasmid DNA. If the plasmid DNA contains more than one recognition site for the restriction enzyme, the linear template DNA has a smaller number of nucleotides than the plasmid DNA. The linear template DNA is then the fragment of the plasmid DNA, which contains the elements necessary for RNA in vitro transcription, that is a promoter element for RNA transcription and the template DNA element. The DNA sequence encoding the target RNA sequence of the linear template DNA determines the sequence of the transcribed RNA by the rules of base-pairing.

5'-cap: A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. Further examples of 5' cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3' phosphorothioate, phosphorodithioate, or bridging or non-bridging methylphosphonate moiety. Further modified 5'-CAP structures which may be used in the context of the present invention are CAP1 (methylation of the ribose of the adjacent nucleotide of m7GpppN), CAP2 (methylation of the ribose of the 2nd nucleotide downstream of the m7GpppN), CAP3 (methylation of the ribose of the 3rd nucleotide downstream of the m7GpppN), CAP4 (methylation of the ribose of the 4th nucleotide downstream of the m7GpppN), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Poly(A) sequence: A poly(A) sequence, also called poly(A) tail or 3'-poly(A) tail, is typically understood to be a sequence of adenine nucleotides, e.g., of up to about 400 adenine nucleotides, e.g. from about 20 to about 400, preferably from about 50 to about 400, more preferably from about 50 to about 300, even more preferably from about 50 to about 250, most preferably from about 60 to about 250 adenine nucleotides. A poly(A) sequence is typically located at the 3' end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

RNA, mRNA: RNA is the usual abbreviation for ribonucleic acid. It is a nucleic acid molecule, i.e. a polymer consisting of nucleotide monomers. These nucleotides are usually adenosine-monophosphate, uridine-monophosphate, guanosine-monophosphate and cytidine-monophosphate monomers, which are connected to each other along a so-called backbone. The backbone is formed by phosphodiester bonds between the sugar, i.e. ribose, of a first and a phosphate moiety of a second, adjacent monomer. The specific order of the monomers, i.e. the order of the bases linked to the sugar/phosphate-backbone, is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA, which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence. Aside from messenger RNA, several non-coding types of RNA exist which may be involved in regulation of transcription and/or translation, and immunostimulation. The term "RNA" further encompass other coding RNA molecules, such as viral RNA, retroviral RNA and replicon RNA, small interfering RNA (siRNA), antisense RNA, CRISPR RNA, ribozymes, aptamers, riboswitches, immunostimulating RNA, transfer RNA (tRNA), ribosomal RNA (rRNA), small nuclear RNA (snRNA), small nucleolar RNA (snoRNA), microRNA (miRNA), and Piwi-interacting RNA (piRNA).

5'-untranslated region (5'-UTR): As used herein, the term '5'-UTR' typically refers to a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'-UTR may be post-transcriptionally modified, for example by addition of a 5'-CAP. In the context of the present invention, a 5'-UTR corresponds to the sequence of a mature mRNA, which is located between the 5'-CAP and the start codon. Preferably, the 5'-UTR corresponds to the sequence, which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence, which corresponds to such RNA sequence. In the context of the present invention, the term "a 5'-UTR of a gene", such as "a 5'-UTR of a TOP gene", is the sequence, which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR. Preferably, the 5'-UTR used according to the present invention is heterologous to the coding region of the mRNA sequence. Even if 5'-UTR's derived from naturally occurring genes are preferred, also synthetically engineered UTR's may be used in the context of the present invention.

3'-untranslated region (3'-UTR): In the context of the present invention, a 3'-UTR is typically the part of an mRNA, which is located between the protein coding region (i.e. the open reading frame) and the 3'-terminus of the mRNA. A 3'-UTR of an mRNA is not translated into an amino acid sequence. The 3'-UTR sequence is generally encoded by the gene, which is transcribed into the respective mRNA during the gene expression process. In the context of the present invention, a 3'-UTR corresponds to the sequence of a mature mRNA, which is located 3' to the stop codon of the protein coding region, preferably immediately 3' to the stop codon of the protein coding region, and which extends to the 5'-side of the 3'-terminus of the mRNA or of the poly(A) sequence, preferably to the nucleotide immediately 5' to the poly(A) sequence. The term "corresponds to" means that the 3'-UTR sequence may be an RNA sequence, such as in the mRNA sequence used for defining the 3'-UTR sequence, or a DNA sequence, which corresponds to such RNA sequence. In the context of the present invention, the term "a 3'-UTR of a gene", such as "a 3'-UTR of an albumin gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence of the 3'-UTR. Preferably, the 3'-UTR used according to the present invention is heterologous to the coding region of the mRNA sequence. Even if 3'-UTR's derived from naturally occurring genes are preferred, also synthetically engineered UTR's may be used in the context of the present invention.

In vitro transcribed RNA: An in vitro transcribed RNA is an RNA molecule that has been synthesized from a template DNA, commonly a linearized and purified plasmid template DNA, a PCR product, or an oligonucleotide. RNA synthesis occurs in a cell free ("in vitro") assay catalyzed by DNA dependent RNA polymerases. In a process called RNA in vitro transcription, virtually all nucleotides analogues into RNA. Particular examples of DNA dependent RNA polymerases are the T7, T3, and SP6 RNA polymerases. An in vitro transcribed RNA may comprise elements such as 5'-cap, optionally a 5'UTR, an open reading frame, optionally a 3'UTR and a poly(A) sequence. Aside from proteinogenic messenger RNA, several non-coding types of RNA exist which may be involved in regulation of transcription and/or translation. Such All RNA molecules as defined herein may also be synthesized by RNA in vitro transcription.

DNA: DNA is the usual abbreviation for deoxy-ribonucleic-acid. It is a nucleic acid molecule, i.e. a polymer consisting of nucleotide monomers. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single-stranded or double-stranded. In the double stranded form, the nucleotides of the first strand typically hybridize with the nucleotides of the second strand, e.g. by A/T-base-pairing and G/C-base-pairing.

Cloning site, multiple cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Open reading frame: An open reading frame (ORF) in the context of the invention may typically be a sequence of several nucleotide triplets, which may be translated into a peptide or protein. An open reading frame preferably contains a start codon, i.e. a combination of three subsequent nucleotides coding usually for the amino acid methionine (ATG), at its 5'-end and a subsequent region, which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated in a longer nucleic acid sequence, for example in a vector or an mRNA. An open reading frame may also be termed "protein coding region".

RNA in vitro transcription: The term "RNA in vitro transcription" (or 'in vitro transcription') relates to a process wherein RNA, in particular mRNA, is synthesized in a cell-free system (in vitro). Preferably, cloning vectorsDNA, particularly plasmid DNA vectors are applied as template for the generation of RNA transcripts. These cloning vectors are generally designated as transcription vector. RNA may be obtained by DNA dependent in vitro transcription of an appropriate DNA template, which according to the present invention is preferably a linearized plasmid DNA template. The promoter for controlling RNA in vitro transcription can be any promoter for any DNA dependent RNA polymerase. Particular examples of DNA dependent RNA polymerases are the T7, T3, and SP6 RNA polymerases. A DNA template for RNA in vitro RNA transcription may be obtained by cloning of a nucleic acid, in particular cDNA corresponding to the respective RNA to be in vitro transcribed, and introducing it into an appropriate vector for RNA in vitro transcription, for example in plasmid circular plasmid DNA. The cDNA may be obtained by reverse transcription of mRNA or chemical synthesis. Moreover, the DNA template for in vitro RNA synthesis may also be obtained by gene synthesis. Preferably cloning vectors are used for RNA in vitro RNA transcription, which are generally designated transcription vectors.

Transformation: In the context of the present invention, transformation comprises the (non-viral) transfer of DNA, most commonly plasmid DNA into competent bacteria. Common transformation techniques comprise heat-shock transformation of chemically competent bacteria (most commonly *Escherichia coli*) and electro-shock transformation of electro competent bacteria, commonly referred to as electroporation. Following that, transformed bacteria are selectively cultured in a suitable medium (e.g., LB-medium) containing antibiotics. The resistance against the antibiotics is transferred by the resistance gene, encoded by the plasmid.

Polymerase chain reaction (PCR): The polymerase chain reaction (PCR) is a technology in molecular biology used to amplify a a piece of DNA across several orders of magnitude, generating thousands to millions of copies of a particular DNA sequence. Developed in 1983 by Kary Mullis (Bartlett, J. M. S.; Stirling, D. (2003). "A Short History of the Polymerase Chain Reaction". PCR Protocols. Methods in Molecular Biology 226 (2nd ed.). pp. 3-6) PCR is now a common and often indispensable technique used in medical and biological research labs for a variety of applications. The method relies on thermal cycling, consisting of cycles of repeated heating and cooling of the reaction for DNA melting and enzymatic replication of the DNA. Primers (short DNA fragments) containing sequences complementary to the target sequence along with a heat-stable DNA polymerase, such as Taq polymerase, enable selective and repeated amplification. As PCR progresses, the DNA generated is itself used as a template for replication, setting in motion a chain reaction in which the DNA template is exponentially amplified. The DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample through a defined series of temperature steps. In the first step, the two strands of the DNA double helix are physically separated at a high temperature in a process called DNA melting. In the second step, the temperature is lowered and the two DNA strands become templates for DNA polymerase to selectively amplify the target DNA. The selectivity of PCR results from the use of primers that are complementary to the DNA region targeted for amplification under specific thermal cycling conditions.

Quantitative Polymerase chain reaction (qPCR) or real-time polymerase chain reaction: A real-time polymerase chain reaction is a laboratory technique of molecular biology based on the polymerase chain reaction (PCR), which is used to amplify and simultaneously detect or quantify a targeted DNA molecule. The procedure follows the general principle of polymerase chain reaction (PCR); its key feature is that the amplified DNA is detected as the reaction progresses in "real time". Two common methods for the detection of products in quantitative PCR are: (1) non-specific fluorescent dyes that intercalate with any double-stranded DNA, and (2) sequence-specific DNA probes consisting of oligonucleotides that are labelled with a fluorescent reporter, which permits detection only after hybridization of the probe with its complementary sequence to quantify nucleic acids. Quantitative PCR is carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and DNA polymerase. The PCR process generally consists of a series of temperature changes that are repeated 25-40 times. These cycles normally consist of three stages: the first, at around 95° C., allows the separation of the nucleic acid's double chain; the second, at a temperature of around 50-60° C., allows the binding of the primers with the DNA template; the third, at between 68-72° C., facilitates the polymerization carried out by the DNA polymerase. Due to the small size of the fragments the last step is usually omitted in this type of PCR as the enzyme is able to increase their number during the change between the alignment stage and the denaturing stage. In addition, some thermal cyclers add another short temperature phase lasting only a few seconds to each cycle, with a temperature of, for example, 80° C., in order to reduce the noise caused by the presence of primer dimers when a non-specific dye is used. The temperatures and the timings used for each cycle depend on a wide variety of parameters, such as: the enzyme used to synthesize the DNA, the concentration of divalent ions and deoxyribonucleotides (dNTPs) in the reaction and the bonding temperature of the primers. The type of quantitative PCR technique used depends on the DNA sequence in the samples, the technique can either use non-specific fluorochromes or hybridization probes.

Quantitative PCR with double-stranded DNA-binding dyes as reporters: A DNA-binding dye such as SYBR Green binds to all double-stranded (ds) DNA in PCR, causing fluorescence of the dye. An increase in DNA product during PCR therefore leads to an increase in fluorescence intensity and is measured at each cycle, thus allowing DNA concentrations to be quantified.

1. The reaction is prepared as usual, with the addition of fluorescent dsDNA dye.
2. The reaction is run in a quantitative PCR instrument, and after each cycle, the levels of fluorescence are measured with a detector; the dye only fluoresces when bound to the dsDNA (i.e., the PCR product). With reference to a standard dilution, the dsDNA concentration in the PCR can be determined. Like other quantitative PCR methods, the values obtained do not have absolute units associated with them (i.e., mRNA copies/cell). As described above, a comparison of a measured DNA/RNA sample to a standard dilution will only give a fraction or ratio of the sample relative to the standard, allowing only relative comparisons between different samples.

Fluorescent reporter probe method: Fluorescent reporter probes detect only the DNA containing the probe sequence; therefore, use of the reporter probe significantly increases specificity, and enables quantification even in the presence of non-specific DNA amplification. Fluorescent probes can be used in multiplex assays—for detection of several genes in the same reaction—based on specific probes with different-coloured labels, provided that all targeted genes are amplified with similar efficiency. The specificity of fluorescent reporter probes also prevents interference of measurements caused by primer dimers, which are undesirable potential by-products in PCR. The method relies on a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the Taq polymerase breaks the reporter-quencher proximity and thus allows unquenched emission of fluorescence, which can be detected after excitation with a laser. An increase in the product targeted by the reporter probe at each PCR cycle therefore causes a proportional increase in fluorescence due to the breakdown of the probe and release of the reporter.

1. The PCR is prepared as usual (see PCR), and the reporter probe is added.
2. As the reaction commences, during the annealing stage of the PCR both probe and primers anneal to the DNA target.
3. Polymerisation of a new DNA strand is initiated from the primers, and once the polymerase reaches the probe, its 5'-3'-exonuclease degrades the probe, physically separating the fluorescent reporter from the quencher, resulting in an increase in fluorescence.
4. Fluorescence is detected and measured in a real-time PCR machine, and its geometric increase corresponding to exponential increase of the product is used to determine the quantification cycle (Cq) in each reaction.

Ligation, DNA ligation: Ligation in molecular biology is the joining of two nucleic acid fragments through the action of an enzyme. It is an essential laboratory procedure in the molecular cloning of DNA whereby DNA fragments are joined together to create recombinant DNA molecules, such as when a foreign DNA fragment is inserted into a plasmid. The ends of DNA fragments are joined together by the formation of phosphodiester bonds between the 3'-hydroxyl of one DNA terminus with the 5'-phosphoryl of another. Ligation in the laboratory is normally performed using T4 DNA ligase, however, procedures for ligation without the use of standard DNA ligase are also popular.

Kozak sequence: As used herein, the term 'Kozak sequence' typically refers to a sequence on an mRNA molecule, which is recognized by the ribosome as the translational start site of a protein encoded by that mRNA molecule. In a preferred embodiment, that sequence may comply with a consensus sequence for a nucleotide sequence mediating initiation of translation, preferably with the consensus sequence (gcc)gccRccAUGG (SEQ ID NO: 20), wherein a lower case letter denotes the most common base at a position where the base can nevertheless vary; upper case letters indicate highly conserved bases, 'AUGG'; 'R' indicates that a purine (adenine or guanine, preferably adenine) is present at this position; and the sequence in brackets is of uncertain significance.

HPLC: High-performance liquid chromatography (HPLC; formerly referred to as high-pressure liquid chromatography), is a technique in analytic chemistry used to separate the components in a mixture, to identify each component, and to quantify each component. It relies on pumps to pass a pressurized liquid solvent containing the sample mixture through a column filled with a solid adsorbent material. Each component in the sample interacts slightly differently with the adsorbent material, causing different flow rates for the different components and leading to the separation of the components as they flow out the column. HPLC is distinguished from traditional ("low pressure") liquid chromatography because operational pressures are significantly higher (50-350 bar), while ordinary liquid chromatography typically relies on the force of gravity to pass the mobile phase through the column. Due to the small sample amount separated in analytical HPLC, typical column dimensions are 2.1-4.6 mm diameter, and 30-250 mm length. Also HPLC columns are made with smaller sorbent particles (2-50 micrometer in average particle size). This gives HPLC superior resolving power when separating mixtures, which is why it is a popular chromatographic technique. The schematic of an HPLC instrument typically includes a sampler, pumps, and a detector. The sampler brings the sample mixture into the mobile phase stream which carries it into the column. The pumps deliver the desired flow and composition of the mobile phase through the column. The detector generates a signal proportional to the amount of sample component emerging from the column, hence allowing for quantitative analysis of the sample components. A digital microprocessor and user software control the HPLC instrument and provide data analysis. Some models of mechanical pumps in a HPLC instrument can mix multiple solvents together in ratios changing in time, generating a composition gradient in the mobile phase. Various detectors are in common use, such as UV/Vis, photodiode array (PDA) or based on mass spectrometry. Most HPLC instruments also have a column oven that allows for adjusting the temperature the separation is performed at.

Endotoxin: Endoxins are lipopolysaccharides (LPS), also known as lipoglycans, which are large molecules consisting of a lipid and a polysaccharide composed of O-antigen, outer core and inner core joined by a covalent bond; they are found in the outer membrane of Gram-negative bacteria, and elicit strong immune responses in animals.

It comprises three parts:
1. O antigen (or O polysaccharide)
2. Core oligosaccharide
3. Lipid A O-antigen: A repetitive glycan polymer contained within an LPS is referred to as the O antigen, O polysaccharide, or O side-chain of the bacteria. The O antigen is attached to the core oligosaccharide, and comprises the outermost domain of the LPS molecule. The composition of the O chain varies from strain to strain.

Core oligosaccharide: The Core domain always contains an oligosaccharide component that attaches directly to lipid A and commonly contains sugars such as heptose and 3-deoxy-D-mannooctulosonic Acid (also known as KDO, keto-deoxyoctulosonate). The LPS Cores of many bacteria also contain non-carbohydrate components, such as phosphate, amino acids, and ethanolamine substituents.

Lipid A:

Lipid A is, in normal circumstances, a phosphorylated glucosamine disaccharide decorated with multiple fatty acids. These hydrophobic fatty acid chains anchor the LPS into the bacterial membrane, and the rest of the LPS projects from the cell surface. The lipid A domain is responsible for much of the toxicity of Gram-negative bacteria. When bacterial cells are lysed by the immune system, fragments of membrane containing lipid A are released into the circulation, causing fever, diarrhea, and possible fatal endotoxic shock (also called septic shock). The Lipid A moiety is a very conserved component of the LPS.

Pyrogen: A pyrogen is a substance that induces fever. These can be either internal (endogenous) or external (exogenous) to the body. The bacterial substance lipopolysaccharide (LPS), present in the cell wall of some bacteria, is an example of an exogenous pyrogen.

Bioburden: As defined herein, the term 'bioburden' typically relates to the number of bacteria, which are present in a given sample, such as the product RNA or an intermediate product of the method according to the invention. In preferred embodiments, the bioburden is determined by any suitable method known in the art, preferably by using a method as described in PhEur 2.6.12.

Lyophilization: Freeze-drying, also known as lyophilization, or cryodesiccation, is a dehydration process typically used to preserve a perishable material or make the material more convenient for transport. Freeze-drying works by freezing the material and then reducing the surrounding pressure to allow the frozen water in the material to sublimate directly from the solid phase to the gas phase.

DNA Sequencing: DNA sequencing is the process of determining the precise order of nucleotides within a DNA molecule. It includes any method or technology that is used to determine the order of the four bases—adenine, guanine, cytosine, and thymine—in a strand of DNA. It includes Maxam-Gilbert sequencing, Sanger sequencing (chain-termination sequencing), next generation sequencing, cycle sequencing, capillary electrophoresis DNA sequencing, single-molecule real-time sequencing, Ion Torrent sequencing, pyrosequencing, sequencing by synthesis, sequencing by ligation.

RNA Sequencing: In order to sequence RNA, the usual method is first to reverse transcribe the sample to generate cDNA fragments. This can then be sequenced as described above for DNA Sequencing.

Reverse Transcriptase: A Reverse transcriptase (RT) is an enzyme used to generate complementary DNA (cDNA) from an RNA template, a process termed reverse transcription. It is mainly associated with retroviruses. Retroviral RT has three sequential biochemical activities: RNA-dependent DNA polymerase activity, ribonuclease H, and DNA-dependent DNA polymerase activity.

Reverse Transcription: Reverse transcription is the process of generating a complementary DNA form an RNA template by a reverse transcriptase.

RT-PCR (Reverse transcription polymerase chain reaction): In RT-PCR, the RNA template is first converted into a complementary DNA (cDNA) using a reverse transcriptase. The cDNA is then used as a template for exponential amplification using PCR.

RNA polymerase/DNA-dependent RNA polymerase: RNA polymerase (RNAP or RNApol), also known as DNA-dependent RNA polymerase, is an enzyme that produces primary transcript RNA. In cells, RNAP is necessary for constructing RNA chains using DNA genes as templates, a process called transcription. RNA polymerase enzymes are essential to life and are found in all organisms and many viruses. In chemical terms, RNAP is a nucleotidyl transferase that polymerizes ribonucleotides at the 3' end of an RNA transcript. Particularly preferred in the context of the present invention are T3, T7 and Sp6 RNA polymerases. FIG. 2 shows consensus promoter sequences. The +1 base is the first base incorporated into RNA during transcription. The underline indicates the minimum sequence required for efficient transcription.

In one aspect, the present invention relates to a method for producing RNA comprising the following steps:
a) providing a template DNA comprising a nucleic acid sequence encoding an RNA sequence;
b) in vitro transcription of the template DNA in order to obtain a composition comprising the RNA;
wherein the method comprises
at least one step for controlling the quality of the template DNA provided in step a), wherein the at least one step for controlling the quality of the template DNA comprises at least one selected from the group consisting of determining the concentration of the template DNA in a sample, determining the integrity of the template DNA, determining the identity of the template DNA, and determining the purity of the template DNA;

and/or at least one step for controlling the quality of the RNA obtained in step b), wherein the at least one step for controlling the quality of the RNA obtained in step b) comprises at least one step selected from the group consisting of determining the concentration of the RNA in a sample, determining the integrity of the RNA, determining the identity of the RNA, determining the purity of the RNA, determining the pH of a sample comprising the RNA, determining the osmolality of a sample comprising the RNA, determining the presence and/or the amount of the template DNA in a sample comprising the RNA, and determining the presence and/or the amount of an organic solvent in a sample comprising the RNA.

According to the invention, the concentration of the template DNA in a sample, the integrity of the template DNA, the identity of the template DNA, preferably the identity of the nucleic acid sequence encoding an RNA sequence, and/or the purity of the template DNA may be determined by any method known in the art. The template DNA is preferably provided in step a) in the form of a liquid composition comprising the template DNA as defined herein. Typically, a (liquid) sample will be taken for each step of quality control. Such sample preferably represents the quality of the template DNA provided in step a). More preferably, such a sample is used for the quality control without further manipulation (e.g. undiluted). Alternatively, a sample may be further processed in order to perform the respective quality control. In a preferred embodiment, the at least one step for controlling the quality of the template DNA comprises a method as described herein, preferably as described herein with respect to methods suitable to be used as quality control of template DNA. In a particularly preferred embodiment, the at least one step for controlling the quality of the template DNA is as described herein, preferably a step as described herein under section 'A. Quality Control 1'. In this context, the expression 'controlling the quality of the template DNA' may refer to a quality control carried out using the (final) product of step a) (i.e. the template DNA comprising a nucleic acid sequence encoding an RNA sequence, which is used as template in step b) of the inventive method), and/or any intermediate product provided in step a) of the method (e.g. a fragment of the template DNA). In a preferred embodiment the quality of the template DNA is controlled at least at two different stages of step a), wherein preferably at least one quality control is carried out using an intermediate DNA product and at least one quality control is carried out using the final product of step a), i.e. the template DNA comprising a nucleic acid sequence encoding an RNA sequence.

In a preferred embodiment, the concentration of the template DNA provided in step a) is determined by photometric measurement, preferably as described herein.

In a further embodiment of the inventive method, the identity of the template DNA provided in step a) is determined in order to control the quality of the template DNA. In this context, it is preferred that the identity of the nucleic acid sequence encoding the RNA sequence, is determined. Any suitable method for directly or indirectly determining the identity of a nucleic acid molecule may be used. Preferably, the identity of the template DNA, more preferably the nucleic acid sequence encoding the RNA, is determined by using at least one step selected from polymerase chain reaction (PCR), restriction analysis or sequence analysis, preferably as described herein.

In a preferred embodiment, the inventive method comprises determining the purity of the template DNA provided in step a). More preferably, the purity of the template DNA provided in step a) is determined by determining in a sample comprising the template DNA the presence and/or the amount of RNA; the presence and/or the amount of protein; the presence and/or the amount of endotoxin; the presence and/or the amount of bacterial DNA; and/or the presence and/or the amount of ribonuclease. According to an embodiment of the present invention, the presence of an RNA, a protein, an endotoxin, a bacterial DNA, and/or ribonuclease may be determined in a qualitative manner. More preferably, such impurities are quantified by using suitable quantitative methods in order to determine the respective amounts.

For instance, the presence and/or the amount of bacterial DNA in a sample comprising the template DNA provided in step a) may be determined by using a polymerase chain reaction (PCR) method. In order to determine the amount of bacterial DNA in a sample comprising the template DNA, quantitative PCR methods, preferably as described herein, are preferably used. Depending on the primer pair, which is employed in such a PCR based method, different bacterial DNA sequences may be amplified and detected.

In a preferred embodiment, the presence and/or the amount of bacterial DNA is determined by using an universal primer pair for bacterial DNA. In that embodiment, the primers are preferably designed in order to amplify universally occurring bacterial DNA. By using such an approach, the general bioburden of the template DNA is preferably determined.

Alternatively, a PCR based method may be used in order to determine the presence and/or the amount of a specific microbial agent, such as a specific bacterial strain. In that embodiment, primer pairs are preferably used having a high specificity for DNA from a certain organism. As an alternative, an universal primer pair for bacterial DNA may be employed. In a preferred embodiment of the invention, the presence and/or the amount of *E. coli* DNA is determined using a primer pair specific for *E. coli* DNA. Preferably, a primer pair is used that is suitable for amplifying the *E. coli* uidA gene. This embodiment is particularly preferred if *E. coli* is used for DNA template amplification.

As explained above with respect to the at least one step for controlling the quality of the template DNA, also the at least one step for controlling the quality of the RNA obtained in step b) may be any suitable method known in the art. According to the inventive method, any method may be used in the at least one step for controlling the quality of the RNA obtained in step b). Preferably, the at least one step for controlling the quality of the RNA obtained in step b) comprises at least one step selected from determining the concentration of the RNA in a sample, determining the integrity of the RNA, determining the identity of the RNA, determining the purity of the RNA, determining the pH of a sample comprising the RNA, determining the osmolality of a sample comprising the RNA, determining the presence and/or the amount of the template DNA in a sample comprising the RNA, and determining the presence and/or the amount of an organic solvent in a sample comprising the RNA, wherein the at least one step is a step as described herein. In a particularly preferred embodiment, the inventive method comprises controlling the quality of the RNA obtained in step b) by determining the concentration of the RNA in a sample, determining the integrity of the RNA, determining the identity of the RNA, determining the purity of the RNA, determining the pH of a sample comprising the RNA, determining the osmolality of a sample comprising the RNA, determining the presence and/or the amount of the template DNA in a sample comprising the RNA, and determining the presence and/or the amount of an organic solvent in a sample comprising the RNA. In a particularly preferred embodiment, the at least one step for controlling the quality of the RNA obtained in step b) is a step as described herein, preferably a step as described herein under section 'B. Quality Control 2'.

The at least one step for controlling the quality of the RNA obtained in step b) is typically carried out in a sample, which is taken from the composition comprising the RNA. In a preferred embodiment, the sample is a liquid sample. In one embodiment, the sample may be taken from the production batch without further processing it. Alternatively, a sample comprising the RNA obtained in step b) may be processed before the quality control. This applies in particular, if a step for quality control is carried out at a stage of the process, where the RNA in the production batch is present in solid form (e.g. after precipitation or lyophilization). In one preferred embodiment, a sample may therefore comprise RNA that has been resuspended in a suitable solvent (e.g. water for injection).

As used herein, the expression 'controlling the quality of the RNA obtained in step b)' may refer to a quality control carried out using the final RNA product (e.g. a purified RNA as described herein) obtained by the inventive method. Furthermore, the expression 'controlling the quality of the RNA obtained in step b)' may also refer to a quality control carried out using any intermediate RNA product obtained in step b) of the inventive method (e.g. the raw RNA product in the (terminated) in vitro transcription batch). In a preferred embodiment of the inventive method, the quality of the RNA is controlled at least at two stages of step b) of the method, wherein preferably at least in one stage the quality of an intermediate RNA product is controlled and at least in one further stage the quality of the final RNA product is controlled.

According to an embodiment of the invention, the method comprises a step of determining by photometric measurement the concentration of the RNA obtained in step b), preferably as described herein.

The inventive method may further comprise at least one step for controlling the quality of the RNA obtained in step b), wherein the integrity of the RNA obtained in step b) is determined by determining the integrity of the RNA e.g. by determining the percentage of full-length RNA, preferably as described herein.

According to the invention, the at least one step for controlling the quality of the RNA obtained in step b) preferably comprises determining the identity of the RNA obtained in step b) by determining the length of the RNA; by digesting the RNA with a ribonuclease; by determining the length of a cDNA obtained by RT-PCR using the RNA as a template; by oligonucleotide mapping; by determining the sequence of the RNA by RNA sequencing; and/or by determining the sequence of a cDNA obtained by RT or RT-PCR using the RNA as a template.

Further preferably, the inventive method comprises determining the purity of the RNA obtained in step b) by determining in a sample comprising the RNA the presence and/or the amount of protein; the presence and/or the amount of endotoxin; the presence and/or the amount of bacterial DNA; the presence and/or the amount of plasmid DNA; and/or the presence and/or the amount of organic solvent. According to one embodiment, the presence of a protein, an endotoxin, a bacterial DNA, a plasmid DNA and/or an organic solvent may be determined in a qualitative manner. More preferably, such impurities are quantified by using suitable quantiative methods in order to determine the respective amounts. For example, the presence and/or the amount of bacterial DNA in a sample comprising the RNA obtained in step b) may be determined by using a PCR method. As described above with respect to a step for controlling the quality of the template DNA, the presence and/or the amount of bacterial DNA can be determined by using an universal primer pair for bacterial DNA. Alternatively, a primer pair specific for E. coli DNA may be used in order to determine the presence and/or the amount of E. coli DNA in a sample comprising the RNA obtained in step b) of the inventive method. Preferably, a primer pair specific for the E. coli uidA gene is used. This embodiment is particularly preferred if E. coli is used for DNA template amplification.

In addition or alternatively to any of the steps described above, the pH and/or the osmolality of a sample comprising the RNA obtained in step b) may be determined. The respective values of the sample are preferably in the ranges as defined herein.

According to the inventive method, step a) may also comprise a step of selecting an RNA sequence. Preferably, the selected RNA sequence is an RNA sequence, which encodes a protein or a fragment or variant thereof, preferably as described herein. In a preferred embodiment, an mRNA sequence is selected in step a) of the method. In that embodiment, the template DNA comprises a nucleic acid sequence encoding an mRNA. Alternatively, the selected RNA may be any other type of RNA or an RNA as defined herein, preferably a small interfering RNA (siRNA), an antisense RNA, a CRISPR RNA, a ribozyme, an aptamer, a riboswitch, an immunostimulating RNA, a transfer RNA (tRNA), a ribosomal RNA (rRNA), a small nuclear RNA (snRNA), a small nucleolar RNA (snoRNA), a microRNA (miRNA), or a Piwi-interacting RNA (piRNA).

According to a preferred embodiment, step a) comprises synthesis of the template DNA, wherein the synthesis of the template DNA or a fragment thereof comprises a step of reverse transcription (RT), more preferably a step of RT-PCR. Preferably, the selected RNA sequence is used as a template in a step of RT-PCR. By using RT or RT-PCR, respectively, cDNA can be synthesized, which corresponds to the selected RNA sequence or a fragment thereof.

In addition or alternatively, the template DNA or a fragment thereof may be synthesized chemically in step a) of the inventive method.

In a preferred embodiment, the synthesis of the template DNA comprises ligating at least two DNA fragments, preferably as described herein, wherein each of the DNA fragments comprises a nucleic acid sequence encoding a fragment of the selected RNA sequence.

According to an embodiment of the invention, the template DNA is a DNA plasmid, preferably a circular DNA plasmid comprising a bacterial origin of replication and a selection marker. Such a plasmid DNA is typically produced in bacteria. Preferably, the plasmid DNA (which—in this embodiment—is the template DNA) is transformed into bacteria, the bacteria are cultured under selective conditions and the plasmid DNA is isolated from the bacteria.

In order to control the quality of the template DNA, at least one step of controlling the quality of the template DNA is preferably carried out after isolation from the bacteria by at least one step selected from photometrically determining the concentration of the template DNA in a sample; determining the presence and/or the amount of RNA contamination; determining the identity of the template DNA by restriction analysis; determining the identity of the template DNA by sequence analysis; determining the presence and/or the amount of endotoxin; determining the presence and/or the amount of protein; determining the bioburden; determining the presence and/or the amount of bacterial DNA; and determining the presence and/or the amount of E. coli DNA. More preferably, the quality of the template DNA is controlled after isolation from the bacteria by using all of the above steps in combination. All of the above steps may be used sequentially, so that certain quality control steps are applied after a certain step in the method and all of the above quality control steps are used over the entire method. Alternatively, all of the above quality control steps are used in combination in order to control the quality of the template DNA at a certain stage or at each of the stages of the inventive method. According to a particularly preferred embodiment, the quality of the template DNA is controlled at a certain stage of the method, preferably after isolation of the template DNA from bacteria after cultivation of the bacteria by photometrically determining the concentration of the template DNA in a sample; determining the presence and/or the amount of RNA contamination; determining the identity of the template DNA by restriction analysis; determining the identity of the template DNA by sequence analysis; determining the presence and/or the amount of endotoxin; determining the presence and/or the amount of protein; determining the bioburden; determining the presence and/or the amount of bacterial DNA; and determining the presence and/or the amount of E. coli DNA. In a particularly preferred embodiment, the quality of the template DNA is controlled after isolation of the template DNA from bacteria after cultivation of the bacteria by at least one step as described herein, preferably a step as described herein under section 'A. Quality Control 1'.

According to an embodiment of the invention, step a) comprises linearization of the template DNA, in particular where the template DNA is a circular molecule, such as a DNA plasmid.

The quality of the template DNA may also be controlled, preferably after linearization of the template DNA, by at least one step selected from the group consisting of controlling the linearization; estimating RNA yield in an in vitro transcription reaction; determining the identity of an RNA obtained in an in vitro transcription reaction; and determining a ribonuclease contamination. A single one of the above steps or all of the above steps may be used sequentially, so that certain quality control steps are applied after a certain step in the method and all of the above quality control steps are used over the entire method. Alternatively, all of the above quality control steps are used in combination in order to control the quality of the template DNA at a certain stage or at each of the stages of the inventive method It is particularly preferred in this embodiment, that all of the steps above are used in combination. Preferably, the quality of the template DNA is controlled at at least one stage of the method, preferably after linearization of the template DNA, by controlling the linearization; estimating RNA yield in an in vitro transcription reaction; determining the identity of an RNA obtained in an in vitro transcription reaction; and determining a ribonuclease contamination.

According to the inventive method, step b) comprises an in vitro transcription reaction. Without any limitation, this reaction may be carried out as known in the art. Preferably, the in vitro transcription of step b) of the inventive method is carried out in presence of naturally occuring nucleotides. Alternatively, the in vitro transcription may also be carried out by using modified nucleotides, preferably as defined herein. In a particularly preferred embodiment, the in vitro transcription reaction is performed in presence of naturally occuring and modified nucleotides.

In a preferred embodiment, the RNA obtained in step b) is a capped RNA, preferably a co-transcriptionally capped RNA.

It is further preferred that the in vitro transcription in step b) is carried out in presence of a cap analog. The cap analog is preferably selected from the group consisting of N7-MeG-pppG (=m7G(5')ppp(5')G), m7G(5')ppp(5')A, ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In a particularly preferred embodiment of the inventive method, the in vitro transcription in step b) is carried out in presence of a cap analog, GTP, ATP, CTP and UTP, wherein the amount of GTP is reduced with respect to the amounts of ATP, CTP and UTP. In that embodiment, ATP, CTP and UTP are preferably present in equal amounts. The ratio of the cap analog to GTP is preferably in a range from 10:1 to 1:1.

The in vitro transcription in step b) is preferably carried out in presence of a DNA dependent RNA polymerase, which is preferably selected from the group consisting of T3 RNA polymerase, T7 RNA polymerase and SP6 RNA polymerase.

In a preferred embodiment, the RNA obtained in step b) is an enzymatically capped RNA. In that embodiment, step b) comprises a step of enzymatically capping the RNA, preferably as described herein.

In some embodiments, the RNA obtained in step b) comprises a poly(A) sequence. Preferably, the RNA obtained in step b) is polyadenylated in a step of enzymatic polyadenylation, wherein the enzyme is preferably a bacterial poly(A) polymerase.

According to a particularly preferred embodiment of the inventive method, the RNA obtained in step b) is purified by at least one purification step in order to obtain purified RNA. The RNA obtained by the in vitro transcription reaction in step b) may optionally be purified by any suitable purification step known in the art or by any combination of such steps. Preferred purification steps include methods for purification compatible with RNA, in particular methods that do not modify the identity of the RNA or that do not have a negative impact on the integrity of the RNA. Further preferred are purification steps, which are compatible with subsequent clinical use of the RNA product.

In a preferred embodiment, the inventive method comprises at least one purification step, which comprises at least one selected from the group consisting of a precipitation step and a chromatographic step. The precipitation step is preferably an alcoholic precipitation step or a LiCl precipitation step. The chromatographic step is preferably selected from the group consisting of HPLC, preferably RP-HPLC, anion exchange chromatography, affinity chromatography, hydroxyapatite chromatography and core bead chromatography.

In particularly preferred embodiments, the RNA obtained in step b) is purified by at least one first and at least one second purification step. The at least one first and at least one second purification step may be the same or different. In certain embodiments, the same purification step may be carried out more than once. In a particularly preferred embodiment, different purification steps are combined with each other, typically by carrying out one purification step after another one. Preferably, the at least one first purification step is carried out prior to the at least one second purification step.

According to a preferred embodiment of the present invention, the at least one first purification step comprises a precipitation step and the at least one second purification step comprises a chromatographic step. Without being bound by any theory, it is believed that the combination of a precipitation step and a chromatographic step is particularly useful for obtaining purified RNA. In that embodiment, it is further preferred that the at least one first purification step comprises an alcohol precipitation step or a LiCl precipitation step and that the at least one second purification step comprises a chromatographic step selected from the group consisting of HPLC, preferably RP-HPLC, anion exchange chromatography, affinity chromatography, hydroxyapatite chromatography and core bead chromatography. Most preferably, the at least one first purification step comprises a LiCl precipitation step and the at least one second purification step comprises a step of RP-HPLC.

According to preferred embodiments of the invention, the method comprises at least one step for controlling the quality of the purified RNA. In this respect, reference is made to the description of the at least one step for controlling quality of the RNA obtained in step b). The steps described herein in this respect equally apply to a purified RNA obtained after an optional purification step as described herein. It is particularly preferred that the quality of the purified RNA is controlled by at least one step as described herein, preferably a step as described herein under section 'B. Quality Control 2'. It is preferred that the success of the at least one optional purification step is controlled by applying at least one step for controlling the quality of the RNA, preferably as defined herein. More preferably, the quality of the purified RNA is controlled after the at least one purification step by at least one step selected from determining the identity of the purified RNA and determining the integrity of the purified RNA.

In embodiments comprising more than one purification step it is preferred that the success of each of the steps is controlled individually by using at least one step for controlling the quality of the RNA as described herein. More preferably, the quality of the purified RNA is controlled after the at least one first purification step and after the at least one second purification step by at least one step selected from determining the identity of the purified RNA and determining the integrity of the purified RNA. The identity of the purified RNA and/or the integrity of the purified RNA are preferably determined by gel electrophoresis, more preferably as described herein.

The RNA obtained in step b), such as the purified RNA as described herein, may further be dried by any suitable method. Preferably, the composition comprising the RNA obtained in step b) or a composition comprising the purified RNA obtained by the inventive method including at least one optional purification step is lyophilized.

According to a particularly preferred embodiment, the quality of the RNA obtained in step b) or the quality of the purified RNA is controlled by at least one step selected from the group consisting of determining the identity of the RNA by digesting the RNA with a ribonuclease; determining the identity of the RNA by using RT or RT-PCR; determining the identity and/or the integrity of the RNA by gel electrophoresis; determining the pH of a sample comprising the RNA; determining the osmolality of a sample comprising the RNA; determining the bioburden; determining the presence and/or the amount of endotoxin; determining the presence and/or amount of protein; determining the presence and/or amount of the template DNA; determining the presence and/or the amount of bacterial DNA; and determining the presence and/or the amounts of organic solvent. It is further particularly preferred that the quality of the RNA is controlled by combining all of the above steps. For instance, the steps above may be applied sequentially by applying one or more of these quality control steps after a certain step in the method for producing RNA, preferably after a certain step following the in vitro transcription in step b) of the inventive method, so that all of these steps are used (at different stages) in the inventive method for producing RNA. Alternatively, all of these steps may be carried out in combination after certain steps in the inventive method or after each step of the inventive method, preferably after the in vitro transcription in step b) of the inventive method or after at least one optional purification step. In a particularly preferred embodiment of the invention, the quality of the RNA obtained in step b) or the quality of the purified RNA is controlled by determining the identity of the RNA by digesting the RNA with a ribonuclease; determining the identity of the RNA by using RT or RT-PCR; determining the identity and/or the integrity of the RNA by gel electrophoresis; determining the pH of a sample comprising the RNA; determining the osmolality of a sample comprising the RNA; determining the bioburden; determining the presence and/or the amount of endotoxin; determining the presence and/or amount of protein; determining the presence and/or amount of the template DNA; determining the presence and/or the amount of bacterial DNA; and determining the presence and/or the amounts of organic solvent.

According to a preferred embodiment, step a) of the inventive method comprises the selection of an RNA sequence. The selected RNA sequence selected typically comprises an RNA sequence, which corresponds to an RNA molecule, which is produced by the inventive method. The selected RNA sequence may be a coding RNA, which encodes a protein sequence or a fragment or variant thereof (e.g. fusion proteins), preferably selected from therapeutically active proteins or peptides, including adjuvant proteins, tumor antigens, pathogenic antigens (e.g. selected, from animal antigens, from viral antigens, from protozoal antigens, from bacterial antigens), allergenic antigens, autoimmune antigens, or further antigens, from allergens, from antibodies, from immunostimulatory proteins or peptides, from antigen-specific T-cell receptors, biologies, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome, for which no therapeutic indication has been identified but which nonetheless have utility in areas of research and discovery. The coding RNAs may be e.g. mRNAs, viral RNAs, or replicon RNAs.

Alternatively, the selected RNA sequence may be any further RNA as defined herein, particularly a small interfering RNA (siRNA), an antisense RNA, a CRISPR RNA, a ribozyme, an aptamer, a riboswitch, an immunostimulating RNA, a transfer RNA (tRNA), a ribosomal RNA (rRNA), a small nuclear RNA (snRNA), a small nucleolar RNA (snoRNA), a microRNA (miRNA), or a Piwi-interacting RNA (piRNA).

If the target RNA sequence that is selected encodes a peptide or a protein, the coding sequence may be readily identified by one of skill in the art by using public and private databases, e.g. GenBank.

In preferred embodiments, the RNA produced by the inventive method comprises naturally occuring and/or modified nucleotides. Several modifications are known in the art, which can be applied to a nucleotide comprised in the RNA obtained by using the inventive method. In a preferred embodiment, the invention thus provides a method for providing a modified RNA, preferably as defined herein, more preferably an RNA comprising at least one modification as described herein.

Chemical Modifications:

The term "RNA modification" as used herein may refer to chemical modifications comprising backbone modifications as well as sugar modifications or base modifications.

In this context, a modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in an RNA molecule as defined herein are chemically modified. A sugar modification in connection with the present invention is a chemical modification of the sugar of the nucleotides of the RNA molecule as defined herein. Furthermore, a base modification in connection with the present invention is a chemical modification of the base moiety of the nucleotides of the RNA molecule. In this context, nucleotide analogues or modifications are preferably selected from nucleotide analogues, which are applicable for transcription and/or translation.

Sugar Modifications:

The modified nucleosides and nucleotides, which may be incorporated into a modified RNA molecule as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), —O(CH$_2$CH$_2$O)nCH$_2$CH$_2$OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diary) amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA molecule can include nucleotides containing, for instance, arabinose as the sugar.

Backbone Modifications:

The phosphate backbone may further be modified in the modified nucleosides and nucleotides, which may be incorporated into a modified RNA molecule as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into a modified RNA molecule as described herein can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-aminopurine-riboside-5'-triphosphate; 2-am inoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methyl inosine-5'-triphosphate 4-thiouridine-5'-triphosphate, 5-am inoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5-triphosphate, 5-bromo-2'-deoxyuridine-5'-triphosphate, 5-iodocytidine-5'-triphosphate, 5-iodo-2'-deoxycytidine-5-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group. In specific embodiments, a modified nucleoside is 5'-O-(1-thiophosphate)-adenosine, 5'-O-(1-thiophosphate)-cytidine, 5'-O-(1-thiophosphate)-guanosine, 5'-O-(1-thiophosphate)-uridine or 5'-O-(1-thiophosphate)-pseudouridine.

In further specific embodiments, a modified RNA may comprise nucleoside modifications selected from 6-aza-cytidine, 2-thio-cytidine, α-thio-cytidine, pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-chloro-purine, N6-methyl-2-amino-purine, pseudo-iso-cytidine, 6-chloro-purine, N6-methyl-adenosine, α-thio-adenosine, 8-azido-adenosine, 7-deaza-adenosine.

In the following, individual preferred aspects and embodiments of the invention are described. Each of these aspects and embodiments, or any combination thereof, may apply in the context of the present invention as defined above and in the claims. In particular, any one of the individual quality control steps, synthesis steps and/or purification steps described in the following, or any combination thereof, may apply to any embodiment of the inventive method.

Reverse Transcription of the Target RNA Sequence:

In order to generate a template DNA for RNA in vitro transcription, the target RNA sequence, which is preferably selected as described above, is preferably reverse transcribed into a DNA sequence (cDNA, complementary DNA). This cDNA may be produced e.g. by using a reverse transcriptase and an RNA sequence comprising the target RNA sequence as template (this is also termed herein as "enzymatic reverse transcription"). Alternatively the reverse transcription may be performed in silico which means that the reverse transcription is performed virtually e.g by a computer.

Synthesis of a Template DNA Comprising a DNA Sequence Encoding the RNA Sequence:

For in vitro transcription, the template DNA preferably comprises at least the following elements in 5'-3' orientation:

a promoter/binding site for a DNA-dependent RNA polymerase such as T3, T7 and SP6 (e.g. as shown in FIG. 2); and a DNA sequence encoding the target RNA sequence.

In case the encoded RNA sequence encodes a peptide or protein, the encoded RNA sequence, which is preferably selected as described above, may be optimized/engineered to generate proteins with desired features (optimized stability, defined localization, membrane integration etc.).

Optionally, the open reading frame encoding the protein encoded by the RNA is sequence-modified (exploiting the degeneration of the genetic code) without altering the encoded protein sequence, for example by GC-enrichment (according to WO02098443), codon optimization (according to WO02098443), elimination of restriction sites used for sub-cloning, elimination of instability motifs (e.g. AU-rich elements, miRNA binding sites). These AU-rich signatures are particularly prevalent in genes with high turnover rates. Based on their sequence features and functional properties, AU-rich elements (AREs) can be categorized into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A) (U/A) nonamers. Molecules containing this type of AREs include GM-CSF and TNF-a. Class III ARES are less well defined. These U-rich regions do not contain an AUUUA motif.

Alternatively, the wild type nucleic acid sequence encoding a protein of interest may be selected.

The DNA sequence encoding the target RNA sequence (unmodified (wild type) or modified) can be produced, for instance, by artificial gene synthesis e.g. by solid-phase DNA synthesis, by oligonucleotide annealing or by PCR.

Synthesis of the Template DNA by PCR:

The template DNA may be synthesized and/or amplified by PCR using the cDNA (complementary to the target RNA sequence) or any DNA comprising the cDNA (e.g. a plasmid vector comprising the cDNA) as template. In this case, the 5'-primer used for PCR preferably comprises the sequence of a promoter of DNA-dependent RNA polymerase to generate a PCR product comprising at least a promoter for a DNA-dependent RNA polymerase and the DNA sequence encoding the target RNA sequence. This synthesized or amplified PCR product used as template for in vitro transcription is termed herein as template PCR product.

The quality of the template PCR product may be controlled by determination of the identity of the DNA sequence encoding the target RNA sequence. Preferably, a method as described herein under section 'A. Quality Control 1' with respect to determination of the identity of the DNA sequence encoding the RNA sequence may be performed. Particularly preferred is PCR or sequencing of the DNA sequence encoding the target RNA sequence.

Synthesis of the Template DNA by Cloning of a DNA Sequence Encoding the RNA Sequence into a Plasmid DNA Vector and Subsequent Amplification:

One alternative for using a PCR product as template for in vitro transcription is the use of plasmid DNA vectors comprising a DNA sequence encoding the RNA sequence (also termed herein "insert DNA sequence") and a promoter of a DNA-dependent RNA polymerase. In this case plasmids can be chosen, which can be amplified e.g. in bacteria particularly *E. coli* by fermentation. This alternative has the advantage that it produces less mutations in the amplified DNA compared to PCR. Alternatively, the insert DNA sequence may be amplified by PCR and therefore the PCR product is used as template for in vitro transcription.

Selection and Design of a Plasmid DNA Vector Backbone:

Plasmid DNA vectors for synthesis of the template DNA plasmids are preferably selected depending on the host organism. For production/replication/amplification of plasmid DNA, bacteria, particularly *Escherichia coli* (*E. coli*) is used.

Plasmids are frequently used as vectors in genetic engineering. Plasmids serve as important tools in genetics and biotechnology labs, where they are commonly used to multiply (make many copies of) or express (translate gene into proteins) particular genes. Many plasmids are commercially available for such uses, including pDP (Ambion), pGEM (Promega), pBluescript (Stratagene), pCRII (Invitrogen), pUC57, pJ204 (from DNA 2.0) and pJ344 (from DNA 2.0), pUC18, pBR322 and pUC19.

Commonly, cDNA encoding or corresponding to the RNA sequence of interest (target RNA sequence) is inserted into a plasmid that typically contains a number of features (possible features listed below). These include a gene that makes the bacterial cells resistant to particular antibiotics (normally kanamycin or ampicillin), an origin of replication to allow bacterial cells to replicate the plasmid DNA, and a multiple cloning site (MCS, or polylinker). A multiple cloning site is a short region containing several commonly used restriction sites allowing the easy insertion of DNA fragments at this location.

Although a very large number of host organisms and molecular cloning vectors are in use, the great majority of molecular cloning experiments begin with a laboratory strain of the bacterium *Escherichia coli* (*E. coli*) and a plasmid cloning vector. *E. coli* and plasmid vectors are in common use because they are technically sophisticated, versatile, widely available, and offer rapid growth of recombinant organisms with minimal equipment.

Particularly useful cloning vectors for *E. coli* are vectors based on pUC19 or pBR322 (J. Vieira, J. Gene. Band 19, Nummer 3, Oktober 1982, S. 259-268, ISSN 0378-1119. PMID 6295879; Sue Lin-Chao et al. Molecular Microbiology. 6, Nr. 22, November 1992, ISSN 0950-382X, S. 3385-3393, doi:10.1111/j.1365-2958.1992.tb02206.x, PMID 1283002. C. Helmer-Citterich et al. (1988). The EMBO journal 7(2), 557-66; C. Yanisch-Perron et al. (1985), Gene. Bd. 33, S. 103-119. PMID 2985470; F. Bolivar et al., Gene. 2, 95-113 (1977); L. Covarrubias et al., Gene. 13, 25-35 (1981)).

For the use as template in in vitro transcription reactions, the plasmid DNA vector typically carries a binding site for a DNA-dependent RNA polymerase, preferably for T3, T7 or SP6 polymerase (T3-, T7-, or SP6 promoter).

To increase the transcription, translation and/or stability further elements can be included in the plasmid:

a 5'-UTR (particularly preferred are TOP-UTRs according to WO2013143700 and WO2013143699);

a Kozak sequence, or another translation initiation element (CCR(A/G)CCAUGG (SEQ ID NO: 21)), where R is a purine (adenine or guanine) three bases upstream of the start codon (AUG), which is followed by another 'G'. 5'UTR also have been known to form secondary structures, which are involved in elongation factor binding);

a 3'-UTR (particularly preferred are UTRs from stable RNAs particularly from albumin gene, an α-globin gene, a β-globin gene, a tyrosine hydroxylase gene, a lipoxygenase gene, and a collagen alpha gene according to WO2013143700;

a poly(A) sequence;

a poly(C) sequence; and/or a stem-loop sequences, e.g. histone stem-loop sequences according to WO2012019780

Particularly preferred are plasmids based on the DNA plasmid pUC19. The different variants (pCV19, pCV26, pCV32, and pCV22 min) differ in restriction sites and 5'- and/or 3'-UTRs. Vectors are preferably based on pCV26 as shown in FIG. 3.

Synthesis of a Template Plasmid DNA Vector:

In certain embodiments, the template DNA comprising a nucleic acid sequence encoding an RNA may be a plasmid DNA vector.

Synthesis of a Template Plasmid DNA Vector by Cloning:

According to a preferred embodiment, a DNA plasmid vector backbone (as defined above) is treated with a restriction endonuclease to linearize the DNA at the site, where the DNA sequence encoding the target RNA sequence (the insert DNA sequence) will be inserted.

The restriction enzyme is commonly chosen so as to generate a configuration at the cleavage site on the vector that is compatible with the one generated at the ends of the insert sequence. Typically, this is done by cleaving the plasmid DNA vector backbone and insert DNA sequence (PCR product, DNA sequence synthesized by artificial gene synthesis e.g. by solid-phase DNA synthesis, or insert retrieved from a plasmid) with the same restriction enzyme(s), for example EcoRI.

To facilitate an oriented integration, two different enzymes, generating two different cleavage site-configurations may be chosen in order to add an insert into a vector (one enzyme at the 5' end and a different enzyme at the 3' end). This ensures that the insert will be integrated in the desired orientation and prevents the vector from ligating to itself during the ligation process.

Recent vectors typically contain a variety of convenient cleavage sites, accumulated in the multiple cloning site (MCS) that are unique within the vector molecule (so that the vector can only be cleaved at a single site). Optionally the MCS is located within a reporter gene (frequently beta-galactosidase) whose inactivation can be used to distinguish recombinant from non-recombinant constructs at a later step in the process (colonies without insert develop a blue color in the presence of the respective substrate and an (optionally) an inducer; blue white selection).

To improve the ratio of recombinant to non-recombinant constructs, the cleaved vector may additionally be treated with an enzyme (a phosphatase, e.g. alkaline phosphatase) that removes the 5' phosphate and therefore prevents the ligase from being able to fuse the two ends of the linearized vector together, and therefore avoids self-ligation. Moreover, linearized vector molecules with dephosphorylated ends are unable to replicate, and replication can only be restored if insert DNA is integrated into the cleavage site.

DNA inserts, encoding the target RNA sequence, and the linearized vector are preferably mixed together at appropriate concentrations (commonly 1:1 or 1:3 molar ratio) and exposed to an enzyme (DNA ligase) that covalently links compatible ends together (that is: sticky ends produced by the same or compatible restriction endonucleases, or blunt ends). This joining reaction is commonly termed ligation (e.g., T4 DNA Ligase). The resulting DNA mixture is then ready for introduction into the host organism (*Escherichia coli*) by means of common transformation techniques, including chemical transformation or electroporation.

Synthesis of the Template Plasmid DNA Vector by Oligonucleotide Annealing:

Alternatively, the template DNA plasmid vector may be synthesized by integrating the DNA sequence encoding the target RNA sequence by oligonucleotide annealing. In this case, the insert DNA sequence is directly synthesized into the sequence of a plasmid DNA vector backbone. This alternative is particularly preferred if the target RNA sequence is not a wild type sequence comprised in a naturally occurring RNA and therefore the reverse transcription cannot be performed by an enzymatic reverse transcription.

The quality of the template plasmid DNA may be controlled by determination of the identity of the DNA sequence encoding the target RNA sequence. Preferably, a method as described herein under section 'A. Quality Control 1' with respect to determination of the identity of the DNA sequence encoding the RNA sequence may be performed. Particularly preferred is restriction analysis and sequencing of the insert DNA sequence.

Amplification of the Template Plasmid DNA Vector:
Transformation:

The template DNA plasmid vector may be amplified by propagation in bacteria, particularly in *E. coli*. Therefore the plasmid is inserted into bacteria by a process called transformation. Particularly preferred are *Escherichia coli* host strains.

Different methods for transformation of plasmid DNA are well known for a person skilled in the art, comprising electroporation of electro-competent cells or heat shock transformation of chemically competent cells.

Particularly preferred is the transformation of chemical competent cells by heat shock, using strains comprising DH5alpha, DH10B, Mach1, OmniMax 2, Stbl2, Top 10, Top 10F.

In this context, 1-10 ng, preferably (4-5 ng) purified plasmid are mixed with 50 µl chemical competent cells, e.g. CaCl$_2$-competent cells, preferably DH5 alpha. The mixture is incubated for at least 30 minutes at 0-5° C. Subsequently, the mixture is incubated for 20 s at 42° C. After the heat shock the mixture is incubated at 0-5° C. for several minutes.

For plating the cells, 900 µl LB-medium is added; incubated for 1-3 h at 37° C. and plated on LB agar plates containing antibiotics e.g. ampicillin or kanamycin, dependent on the antibiotic resistance gene encoded on the vector, and incubated 12-24 h at 37° C.

The transformation efficacy is evaluated based on the number of colonies formed. *E. coli* cells are transformed for each production campaign. Only bacteria that take up copies of the plasmid survive, since the plasmid makes them resistant (ampicillin resistance). In particular, the resistance genes are expressed (used to make a protein) and the expressed protein either breaks down the antibiotics or prevents it from inhibiting certain bacterial pathways. In this way, the antibiotics act as a filter to select only the bacteria containing the plasmid DNA. Now these bacteria can be grown in large amounts, harvested, and lysed to isolate the plasmid of interest.

Fermentation:

In a preferred embodiment, a single transformed *E. coli* colony is taken from the agar plate and used to inoculate a liquid LB medium culture (containing antibiotics, e.g. 100 µg/ml ampicillin). The culture is grown for 4-8 h at 37° C. under shaking. 5-10 ml of that culture are then used to inoculate a larger volume (e.g. 1 l LB medium containing antibiotic) contained in the fermenter.

During fermentation overnight (12-20 h), standard parameters are precisely regulated and continuously monitored (e.g., pH, oxygen concentration, anti-foam, shaking, temperature). The cell density is controlled by photometric determination at 600 nm. After fermentation, a culture sample is preferably taken for quality control and cells are harvested and centrifuged. The cell pellet can be stored at ≤−20° C.

Quality Control: Isolation of Plasmid DNA and Subsequent Analysis of the Plasmid DNA Plasmid DNA is preferably isolated from 1 ml of *E. coli* cells using a standard plasmid preparation kit known in the art. The concentration of the isolated plasmid DNA is determined by a standard photometric method for nucleic acids via measurement of the absorption at 260 nm (OD260) to estimate the expected total plasmid DNA yield of the whole fermentation. To confirm the correct gene, the restriction pattern of the extracted plasmid DNA is preferably analyzed and evaluated according to 'Quality Control 1' as described herein.

Alternatively, a person skilled in the art may conduct a PCR using suitable primer pairs with *E. coli* cells as template. The PCR product may be analyzed using agarose gel electrophorese (see section 'A. Quality Control 1')

Isolation of plasmid DNA by mini preparation kit:

Preparations of plasmid DNA can be obtained by various methods known in the art, comprising the alkaline lysis method and the boiling method (see e.g. Sambrook et al., Molecular Cloning, a laboratory manual, 2nd edition, Cold Spring Harbor Laboratory Press 1989. 1.25)

Moreover, various kits for preparation of plasmid DNA are commercially available (e.g. NucleoSpin Plasmid Kit; Macherey Nagel; QIAprep Miniprep kit; QIAGEN) which commonly use a silica membrane that binds DNA in the presence of a high concentration of chaotropic salt, and allows elution in a small volume of low-salt buffer. This technology eliminates time consuming phenol-chloroform extraction and alcohol precipitation.

The concentration of the isolated plasmid DNA is determined preferably by a standard photometric method for nucleic acids via measurement of the absorption at 260 nm (OD260).

Quality Control of the Plasmid DNA:

Determination of the identity of the DNA sequence encoding the target RNA sequence. Preferably, any method known in the art or as described in section 'A. Quality Control 1' herein to determine the identity of the DNA sequence encoding the target RNA sequence may be performed. Particularly preferred is restriction analysis.

Plasmid Preparation: Plasmid DNA is isolated from the frozen *E. coli* cell culture pellet by any method known in the art, preferably by chromatography using a giga preparation kit, most preferably by an endotoxin-free giga preparation kit (e.g. EndoFree Plasmid Giga Kit of Qiagen, or Endotoxin-free plasmid DNA purification of Macherey Nagel).

For the production of medicaments it is very important to minimize the endotoxin level during the production process.

The concentration of the isolated plasmid DNA is preferably determined by a standard photometric method for nucleic acids via measurement of the absorption at 260 nm (OD260).

The yield of the isolated plasmid DNA is calculated. (Determination of the content of the template DNA plasmid)

Quality Control of the Plasmid DNA: Determination of the Identity of the DNA Sequence Encoding the Target RNA Sequence and Determination of Purity of Template DNA Plasmid Any method as described in section 'A. Quality Control 1' herein to determine the identity of the DNA sequence encoding the target RNA sequence may be performed. Particularly preferred is restriction analysis and sequencing of the insert DNA sequence. In addition, the purity of the plasmid preparation is preferably determined. Any method as described in section 'A. Quality Control 1' to determine the purity may be used. Particularly preferred is the determination of RNA contaminations, determination of endotoxins, determination of protein content, determination of bioburden, and determination of residual E. coli DNA.

Linearization:

The isolated plasmid DNA is typically linearized by a specific, preferably singular, enzymatic restriction to provide a defined linear template for the following RNA in vitro transcription process. This ensures a defined termination of the in vitro RNA transcription procedure by avoiding transcriptional read-through. The linearized DNA template is preferably purified and the content and yield of the linear DNA is determined.

Preferred endonucleases for linearizing the pDNA template include BciVI, XbaI, SpeI, HindIII, NotI, EcoRI, NdeI, AflIII, HindIII, and SapI. The most preferred restriction enzyme is EcoRI.

Further details regarding restriction digestion is disclosed in section 'A. Quality Control 1' herein.

Particularly preferred are the following conditions:
Composition of One Reaction:
1 µg plasmid DNA
0.5 µl reaction buffer
3 units restriction enzyme
Add. 5 µl with WFI (water for injection)

The composition is calculated according to the amount of plasmid DNA used for linearization (at least 1000 reactions, preferably 10000 reactions).

The reaction is incubated for 4 to 5 hours at 37° C.

Purification of the Linearized Template Plasmid DNA:

The linearized template DNA is preferably purified. Different methods can be used, e.g. phenol/chloroform extraction with subsequent alcohol precipitation, chromatographic methods or filtration methods, or silica-based DNA capture methods.

This step also ensures the reduction of impurities (e.g. proteins) from the previous manufacturing steps, including E. coli proteins, restriction enzymes and BSA (contained in reaction buffers).

In this context, phenol/chloroform/isoamylalcohol precipitation with subsequent isopropanol precipitation is particularly preferred. These methods are described in Sambrook et al., Molecular Cloning, Second Edition, 1989, Cold Spring Harbor Laboratory Press).

After precipitation, the plasmid DNA is resuspended in a suitable buffer, preferably water for injection.

Quality Control of Linearized Template Plasmid DNA Vector: Determination of Completeness of Linearization, Estimation of RNA Yield and Determination of Identity of RNA Determination of Completeness of Linearization Linear template plasmid DNA is preferably analyzed for successful/complete linearization. The band uniqueness and band size of the linear plasmid DNA are preferably analyzed via agarose gel electrophoresis. The agarose gel electrophoresis is carried out as described in section 'Quality Control 1' herein in the context of restriction analysis. Alternatively, any other method known in the art for determining DNA fragments may be used, in particular the methods as described herein. Preferably, 0.5 µg linearized plasmid DNA are analyzed by agarose gel electrophoresis.

Therefore, in one aspect the present invention provides a method for analysis of successful linearization of plasmid DNA, in particular, a method for analysis of successful linearization of plasmid DNA for use as quality control in the manufacture of plasmid DNA and/or in a method for producing RNA.

Test Transcription:

A small scale transcription test with linear template DNA into RNA via a polymerization reaction by RNA polymerase is preferably performed. This small scale test in vitro transcription is performed to estimate the expected yield of in vitro transcribed RNA and to analyze the identity of the in vitro transcribed RNA.

An in vitro transcription reaction commonly contains, but is not limited to, DNA template, a suitable buffer (HEPES, Tris-HCl pH 7.5), DNA dependent RNA polymerase (e.g. T7, T3, SP6), a suitable nucleotide mixture (natural and/or modified nucleotides), DTT, spermidine, NaCl, $MgCl_2$, RNAse inhibitor and pyrophosphatase. More details are described in the section RNA transcription herein specifically dedicated to in vitro transcription as such.

Subsequently, the in vitro transcribed RNA is preferably purified. Different methods for RNA purification are known in the art including phenol/chloroform/isoamylalcohol extraction with subsequent ethanol or isopropanol precipitation, precipitation with alcohol and a monovalent cation such as sodium or ammonium ion, LiCl precipitation, chromatographic methods or filtration methods.

In this context, LiCl precipitation is particularly preferred. LiCl precipitation is preferably performed by adding 50% of the volume 8 M LiCl. The reaction is mixed and incubated at room temperature. Subsequently the reaction is centrifuged, the supernatant discarded and the RNA pellet washed with 75% ethanol. After drying the RNA is preferably resuspended in water.

Estimation of RNA Yield by Photometric Determination of the RNA Concentration

The concentration of the test in vitro transcription is preferably determined by photometry as described in section 'B. Quality Control 2'. Therefore, the yield of in vitro transcribed RNA can be estimated.

Determination of RNA Identity in Test In Vitro Transcription

The RNA identity in the test in vitro transcription is preferably determined by any method known in the art, particularly by any method described herein in section 'B. Quality Control 2'. Particularly preferred is agarose gel electrophoresis as described herein in section 'B. Quality Control 2'.

Therefore, in one aspect the present invention provides a small scale test in vitro transcription used as quality control for the manufacture of template DNA and/or for the manufacture of in vitro transcribed RNA. It is used for estimation of the yield of in vitro transcribed RNA and to analyze for identity of the in vitro transcribed RNA.

A. Quality Control 1

In this section (section A and subsections), preferred steps are described for controlling the quality of the template DNA comprising a nucleic acid sequence encoding the RNA. In particular, this section relates to preferred steps for determination of the template DNA content, determination of the identity of the DNA sequence encoding the target RNA sequence and/or determination of the purity of the template DNA.

A.1 Determination of Template Plasmid DNA Content

The concentration of the isolated template plasmid DNA (dsDNA) is preferably determined by a standard photometric method for nucleic acids via measurement of the absorption. Moreover, the OD 260/280 value is preferably determined which measures the purity of a nucleic acid sample. For pure DNA, A260/280 is approximately 1.8.

A.2 Determination of the Identity of the DNA Sequence Encoding the Target RNA Sequence A.2.1 Determination of the Identity of the DNA Sequence Encoding the Target RNA Sequence by PCR:

To confirm that the obtained template DNA comprises the nucleic acid sequence encoding the RNA sequence, PCR with appropriate primers may be performed. Primers located in the nucleic acid sequence encoding the target RNA sequence or primers located outside of the nucleic acid sequence encoding the target RNA sequence may be used for PCR.

If a plasmid DNA vector is used as template for the in vitro transcription, also primers located on the backbone of the plasmid DNA vector may be used, e.g. standard primers such as M13, Sp6, or T7 primers flanking the insert DNA sequence encoding the target RNA sequence.

The resulting PCR-amplified products may be analyzed by any method known in the art such as by gel electrophoresis e.g. agarose gel electrophoresis, DNA sequencing or chromatography e.g. HPLC). Particularly preferred is the analysis by agarose gel electrophoresis or HPLC.

In one aspect, the present invention provides PCR used as a method for analysis of template DNA, for controlling the identity of the DNA sequence encoding the target RNA sequence. Particularly, this method is used as a quality control for the production of template DNA in a method for producing RNA, preferably in the production process of in vitro transcribed RNA.

A.2.2 Determination of the Identity of the DNA Sequence Encoding the Target RNA Sequence by Restriction Analysis Alternatively or additionally to other methods, such as PCR, restriction analysis of the template plasmid DNA vector comprising the insert DNA sequence encoding the target RNA sequence is preferably conducted and the resulting fragments of the plasmid DNA vector are analyzed to confirm that the template plasmid DNA vector contains the insert DNA sequence encoding the target RNA sequence.

Restriction Reaction:

Restriction enzymes specifically bind to and cleave double-stranded DNA at specific sites within or adjacent to a particular sequence known as the recognition site. Most of the restriction enzymes recognize a specific sequence of nucleotides that are four, five or six nucleotides in length and display twofold symmetry. Some cleave both strands exactly at the axis of symmetry, generating fragments of DNA that carry blunt ends; others cleave each strand at similar locations on opposite sides of the axis of symmetry, creating fragments of DNA that carry single-stranded termini (See Definitions).

The reaction conditions used for the restriction digestion are dependent on the used restriction enzymes. Particularly, the salt concentration differs depending on the used restriction enzyme. Therefore, the manufacturer of restriction enzymes optimized buffers for their restriction enzymes.

Preferred conditions for a restriction reaction with one restriction enzyme are:
0.5 µg plasmid DNA (0.2-2 µg plasmid DNA)
1.5 µl 10× reaction buffer
1 µl restriction enzyme (1 µl normally comprises 1 u)
Add. 15 µl WFI (water for injection)

Preferred conditions for a restriction reaction with two restriction enzymes are:
0.5 µg plasmid DNA (0.2-2 µg plasmid DNA)
1.5 µl 10× reaction buffer
1 µl restriction enzyme 1 (1 µl normally comprises 1 u)
1 µl restriction enzyme 2 (1 µl normally comprises 1 u)
Add. 15 µl WFI (water for injection)

The restriction reaction is typically mixed as shown above and incubated preferably for 1-4 hours at 37° C.

In this context, it is particularly preferred that restriction enzymes are combined, which cut 5'- and 3' of the insert DNA sequence. Alternatively, a specific combination of restriction enzymes is chosen dependent on the insert DNA sequence. In this case, it is particularly preferred to choose a restriction enzyme, which cuts only once in the DNA plasmid backbone and a restriction enzyme, which cuts once in the insert DNA sequence.

It is particularly preferred to perform at least one, 2, 3, 4 or 5 different restriction reactions using different restriction enzyme(s) (combinations) in order to control the identity of the insert DNA sequence comprising the nucleic acid sequence encoding the target RNA sequence.

The identity of the insert DNA sequence contained in the template plasmid DNA vector is controlled by enzymatic restriction and subsequent analysed preferably via agarose gel electrophoresis. For this purpose, template plasmid DNA is incubated with a certain number of specific restriction enzymes (preferably in at least five independent reactions) leading to a specific fragmentation of the template plasmid DNA vector. Subsequently, the restricted DNA samples are analyzed by separation of the obtained fragments of different sizes e.g. on an agarose gel or by e.g. by HPLC. The received fragmentation pattern of the DNA is compared to the theoretically expected restriction pattern.

Analysis of the DNA Fragments Resulting from Restriction Reaction:

Exemplary methods for analyzing DNA fragments are, for instance, agarose gel electrophoresis, polyacrylamide gel electrophoresis, chip gel electrophoresis, capillary electrophoresis, fluorescence-based automatic DNA-fragment analysis and HPLC (e.g. WAVE™ DNA Fragment Analysis System).

Particularly preferred is agarose gel electrophoresis as described in Sambrook et al., Molecular Cloning, a laboratory manual, 2nd edition, Cold Spring Harbor Laboratory Press 1989. 6.

Electrophoresis through agarose gels is a method to separate DNA fragments. The DNA can be determined in the agarose gel by addition of the fluorescent intercalating dye ethidium bromide or other commercially available DNA dyes (SybrSafe DNA stain, Cybr Green, Orange DNA loading dye)

Different running buffers can be used, e.g. TBE (Tris-borate) or TAE (Tris-acetate) buffer:

1×TBE (Tris-borate):

89 mM Tris base 89 mM boric acid 2 mM EDTA

1×TAE (Tris-acetate):

40 mM Tris 20 mM acetic acid 1 mM EDTA

For the preparation of the agarose gel 0.3-5% (w/v) agarose or more preferably 0.8% (w/v) agarose is melted in 1× running buffer, preferably 1×TBE buffer. Ethidium bromide is added to the solution, preferably 1-5 µl per 100 µl agarose gel solution.

The solution is poured into a mold and allowed to harden. When an electric field is applied across the gel, DNA, which is negatively charged, migrates to the anode. As running buffer the same buffer as used for preparation of the agarose gel is used.

Loading buffer (e.g. 6× Orange DNA Loading Dye) is added to the sample and loaded onto the agarose gel. In this context the whole reaction (15 µl) is mixed with an appropriate volume of loading buffer e.g. 3 µl 6 Orange DNA Loading Dye.

After gel running the DNA fragments can be determined by ultraviolet light. The pattern of fragments can be compared to the predicted restriction pattern and therefore allows the determination if the correct DNA sequence encoding the target RNA sequence is integrated into the plasmid.

Therefore, in one aspect, the present invention provides restriction analysis used as a method for analysis of plasmid DNA, particularly for controlling the identity of the insert DNA sequence. Particularly this method is used as a quality control for the production of template plasmid DNA in a method for producing RNA, preferably in a production process of in vitro transcribed RNA.

A.2.3 Determination of the Identity of the DNA Sequence Encoding the Target RNA Sequence by DNA Sequencing:

Automated DNA sequencing of the insert DNA sequence of the plasmid DNA or of the PCR product encoding the target RNA sequence may be performed to confirm the identity of the DNA sequence encoding the target RNA sequence. The DNA sequencing may be performed by any method known in the art, particularly by any method defined herein. Selection of appropriate primers for DNA sequencing ensures that the complete length of the DNA sequence encoding the target RNA sequence is completely covered for both complementary strands of the DNA primers (primers flanking the DNA sequence encoding the target RNA sequence e.g. the insert DNA sequence, located on the backbone of the plasmid, e.g., M13 forward, and M13 reverse). The received sequence information is compared to the expected sequence of the DNA sequence encoding the target RNA sequence.

Therefore, it is particularly preferred in the context of the present invention to confirm or to control the identity of the DNA sequence encoding the target RNA sequence. In this context it is particularly preferred to use primers which lay 5' and/or 3' of the DNA sequence encoding the target RNA sequence e. g. comprised in the template plasmid DNA vector or in the template PCR product.

The following primer is particularly preferred:

```
M13-universal Primer:
5'- CGCCAGGGTTTTCCCAGTCACGAC    (SEQ ID NO: 7)
```

Therefore, in one aspect the present invention provides DNA sequencing used as a method for analysis of template DNA, particularly for controlling the identity of the DNA sequence encoding the target RNA sequence. Particularly this method is used as a quality control for the production of template DNA in a method for producing RNA, preferably in a production process of in vitro transcribed RNA.

A.3 Determination of Purity of Template Plasmid DNA Preparation:

A.3.1 Determination of RNA Contaminations in the Template DNA Preparation Using RNAse Treatment Template DNA may further be controlled with respect to RNA-contamination. Preferably, the template DNA e.g. plasmid DNA is incubated with RNase A. Afterwards the concentration of the purified template DNA is determined again and the difference before and after RNase treatment is calculated.

The following reaction is particularly preferred:

1-20 µg template DNA, preferably 10-15 µg template DNA are incubated with 1 µl RNAse A (1 g/l) for 1 h at 37° C.

Nucleotides are separated e.g. by alcohol precipitation, chromatography, preferably on Sephadex columns.

Preferably, the concentration of the isolated template DNA, preferably after RNase A digestion, is determined by a standard photometric method for nucleic acids via measurement of the absorption at 260 nm (OD260) (see above).

Calculation of the percentage of template DNA contained in the template DNA preparation:

$$\% \text{ template } DNA = \frac{\text{concentration of nucleic acids after } RNase \ A \text{ digestion}}{\text{concentration of nucleic acids before } RNase \ A \text{ digestion}} \times 100\%$$

Therefore, in one aspect the present invention provides RNAse digestion used as a method for analysis of DNA, particularly for controlling the contamination with RNA. Particularly this method is used as a quality control for the production of template DNA in a method for producing RNA, preferably in a production process of in vitro transcribed RNA.

A.3.2 Determination of Endotoxins in Template DNA Preparation:

A test for bacterial endotoxins is preferably carried out in order to determine the presence and/or the amount of endotoxins in the template DNA preparation. Preferably, endotoxins of gram-negative bacterial origin are detected and/or quantified by using amoebocyte lysate from horseshoe crab (*Limulus polyphemus* or *Tachypleus tridentatus*). The principle has been discovered by Levin (Levin, J. 1979. The reaction between bacterial endotoxin and amebocyte lysate, p. 131-146. In E. Cohen (ed.), Biomedical Applications of the Horseshoe Crab (Limulidae), Progress in Clinical and Biological Research, Vol. 29. Alan R. Liss, Inc., NewYork).

In general, there are at least 3 techniques for performing this test: the gel-clot technique, which is based on gel formation; the turbidimetric technique, based on the development of turbidity after cleavage of an endogenous substrate; and the chromogenic technique, based on the development of colour after cleavage of a synthetic peptide-chromogen complex.

Preferred is the LAL-test. The amount of endotoxins per volume of plasmid DNA is determined and evaluated via kinetic-turbidometric LAL (*Limulus*-Amoebocyte-Lysate) test according to Ph. Eur. 2.6.14 (Pharmacopoea Europaea).

Therefore, in one aspect the present invention provides a method for determination of endotoxins in DNA preparations, preferably plasmid DNA preparations, particularly used as quality control for the production of plasmid DNA. Particularly, this method is used as a quality control for the production of template plasmid DNA in a method for producing RNA, preferably in a production process of in vitro transcribed RNA.

A.3.3 Determination of protein concentration in template DNA preparation: The total protein content per volume of template plasmid DNA is preferably calculated. Several different methods are known in the art for detection of protein, including UV absorbance measurements at 280 nm (due to the presence of aromatic amino acids), the Lowry assay, the Biuret assay, the Bradford assay, and the BCA (Bichinonic Acid) assay.

The BCA (Bichinonic Acid) assay, a colorimetric method of detection is based on complexation of proteins with copper and BCA. The total protein concentration contained in the RNA is measured via absorption at 562 nm compared to a protein standard (BSA). The principle of the bicinchoninic acid (BCA) assay is similar to the Lowry procedure (Lowry, O. H. et al, J. Biol. Chem., 193, 265-275 (1951)). Both rely on the formation of a $Cu^{2+}$-protein complex under alkaline conditions, followed by reduction of the $Cu^{2+}$ to $Cu^+$. The amount of reduction is proportional to the protein present. It has been shown that cysteine, cystine, tryptophan, tyrosine, and the peptide bond are able to reduce $Cu^{2+}$ to $Cu^+$. BCA forms a purple-blue complex with $Cu^+$ in alkaline environments, thus providing a basis to monitor the reduction of alkaline $Cu^{2+}$ by proteins at absorbance maximum 562 nm.

Another method, which can be used for the determination of protein is the Bradford method. The Bradford assay, a colorimetric protein assay, is based on an absorbance shift of the dye Coomassie Brilliant Blue G-250 in which under acidic conditions the red form of the dye is converted into its bluer form to bind to the protein being assayed. The (bound) form of the dye has an absorption spectrum maximum historically held to be at 595 nm. The cationic (unbound) forms are green or red. The binding of the dye to the protein stabilizes the blue anionic form. The increase of absorbance at 595 nm is proportional to the amount of bound dye, and thus to the amount (concentration) of protein present in the sample.

Particularly preferred is the BCA assay. For performing a BCA assay, several commercially available kits may be used.

Therefore, in one aspect the present invention provides a method for determination of protein in DNA preparations, preferably plasmid DNA preparations, particularly used as quality control in the manufacture of plasmid DNA and/or in a method for producing RNA, such as the manufacture of in vitro transcribed RNA.

A.3.4 Determination of the Bioburden in Template DNA Preparation:

To determine sterility of the template DNA preparation, a PCR using universal bacterial primers (detecting universal occurring genes in bacteria) may be performed. Moreover, a plating assay may be conducted.

Particularly Preferred is a Plating Assay According to PhEur 2.6.12.:

For determination of the bioburden the presence/absence of bacteria is tested under aerobe and anaerobe conditions after plating the plasmid DNA on agar- and/or glucose plates and incubation for several days (e.g. 5 and 7 days, respectively). The bioburden is assessed by counting the bacteria clones grown on bacteria plates.

For this purpose, different media for plating can be used. Tryptic Soy Agar (TSA) (Soybean Casein Digest Agar (CSA)) and Sabouraud Glucose (2%) Agar plates are particularly preferred.

Therefore, in one aspect the present invention provides a method for determination of the bioburden in DNA preparations, preferably plasmid DNA preparations, particularly used as quality control for the manufacture of plasmid DNA and/or for the manufacture of in vitro transcribed RNA.

A.3.5 Determination of Residual Bacterial DNA:

In case *E. coli* is used for amplification of the template plasmid DNA, the residual *E. coli* DNA is preferably determined.

Residual *E coli* DNA may be detected via PCR, preferably via quantitative PCR (qPCR) using primers and probes specific for *E. coli* genes. In this context primers and probes specific for any genomic sequence or gene comprised in the respective bacterial strain (e.g. *E. coli* strain) is particularly useful to perform a PCR or qPCR to determine residual bacterial DNA. Particularly preferred are primers and probes specific for the *E. coli* gene uidA.

Plasmid DNA is checked for residual *E. coli* DNA. For this purpose quantitative PCR (qPCR) is performed with the plasmid DNA sample together with a positive and a negative control and the calculated number of copies of genomic *E. coli* DNA is assessed. For this purpose the *E. coli* specific gene uidA is amplified and quantified. Preferably the Light Cycler from Roche is used in combination with FastStart DNA MasterPlus Hybridization Probes.

The following primers and probes are preferably used for the quantitative PCR detecting the uidA gene:

```
Primer EC 679U:
GGACAAGGCACTAGCG            (SEQ ID NO: 8)

Primer EC 973 L:
ATGCGAGGTACGGTAGGA          (SEQ ID NO: 9)

Probe EC1 FL:
CATCCGGTCAGTGGCAGT-FL       (SEQ ID NO: 10)

Probe EC1 LC:
LC640-AAGGGCGAACAGTTCCTGA-ph (SEQ ID NO: 11)
```

Alternatively, any other gene of the respective bacterial strain (particularly *E. coli* strain) used for fermentation may be used for the PCR or quantitative PCR.

Therefore, in one aspect the present invention provides a method for determination of residual bacterial DNA particularly used as quality control in the manufacture of plasmid DNA and/or in a method for producing RNA, such as the manufacture of in vitro transcribed RNA.

A.3.6 Determination of RNase Contaminations in Template DNA:

The template DNA (e.g. the linear template plasmid DNA) is preferably analyzed for RNase contamination using commercially available RNase detection kits, including RNaseAlert® (Applied Biosystems), RNase contamination assay (New England Biolabs) or an assay where the incubation of the template DNA with a reference RNA serves as a readout for RNase contamination.

The template DNA may be analyzed for RNase contamination by using the RNaseAlert® kit, which utilizes an RNA substrate tagged with a fluorescent reporter molecule (fluor) on one end and a quencher of that reporter on the other. In the absence of RNases, the physical proximity of the quencher dampens fluorescence from the fluor. In the presence of RNases, the RNA substrate is cleaved, and the fluor and quencher are spatially separated in solution. This causes the fluor to emit a bright green signal when excited by light of the appropriate wavelength. Fluorescence can be readily detected with a filter-based or monochromator-based fluorometer.

The template DNA may be alternatively analyzed for RNase contamination by using an RNase Contamination Assay Kit (New England Biolabs) which detects general RNase activities including non-enzyme based RNA degradation due to heavy metal contamination in samples and high pH. The assay probe is a fluorescein labeled RNA transcript (300-mer). After incubation with a pDNA sample the integrity of the RNA probe is analyzed on denaturing PAGE followed by SYBR Gold staining or preferably by scanning with a FAM/Fluorescein capable imaging system.

In a preferred embodiment, the template DNA is analyzed for RNase contamination by incubation of the template DNA (preferably the linear template plasmid DNA) with a reference RNA and subsequent analysis via RNA agarose gel electrophoresis. In case of absence of RNase both the linear DNA and the reference RNA can be detected on the agarose gel, in case of RNase contamination, only the DNA band can be detected.

Therefore in one aspect the present invention provides a method for determination of RNases particularly used as quality control for the manufacture of template DNA and/or for the manufacture of in vitro transcribed RNA.

RNA Transcription

RNA can be produced "in vitro", for example, from a PCR-based DNA template, or a plasmid DNA based linearized DNA template using DNA dependent RNA polymerases.

Particularly preferred is in vitro transcription of RNA using a linearized plasmid DNA template.

The linearized template DNA plasmid produced in the previous steps is transcribed using DNA dependent RNA in vitro transcription. That reaction typically comprises a transcription buffer, nucleotide triphosphates (NTPs), an RNase inhibitor and a DNA-dependent RNA polymerase. The NTPs can be selected from, but are not limited to, those described herein including naturally occuring and modified NTPs. The DNA-dependent RNA polymerase can be selected from, but is not limited to, T7 RNA polymerase, T3 RNA polymerase, SP6 RNA polymerase and mutant polymerases such as, but not limited to, polymerases able to incorporate modified nucleic acids.

Particularly preferred is T7 RNA polymerase as an enzyme for RNA in vitro transcription.

During polymerization, the mRNA may be co-transcriptionally capped at the 5' end with a standard cap analogue as defined herein (e.g. N7-MeGpppG).

As transcription buffer following buffers are preferred: 40 mM Tris pH 7.5 or 80 mM HEPES. 80 mM HEPES is particularly preferred.

Template DNA: 10-500 µg/ml, particularly preferred are 50 µg/ml

Nucleotide triphosphates of the desired chemistry are used, including naturally occuring nucleotides (e.g. at least one of the nucleotides ATP, CTP, UTP and GTP) and/or modified nucleotides, preferably modified nucleotides as described herein, or any combination thereof.

ATP, CTP, UTP and GTP are preferably used in a concentration of 0.5-10 mM, preferably in a concentration of 3-5 mM and most preferably in a concentration of 4 mM.

Useful guanine analogs include, but are not limited to, N7-MeGpppG (=m7G(5')ppp(5')G), m7G(5')ppp(5')A, ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine. If 5'-CAP (cap analog) is used, the concentration of GTP is decreased compared to the other used nucleotides. Preferably 10 to 50% of GTP is used compared to the concentration of ATP, CTP and UTP. Most preferably 20-30% of GTP is used.

Furthermore the cap analog is used in a concentration which is at least the same as the concentration of ATP, CTP and UTP.

The ratio of cap analog:GTP can be varied from 10:1 to 1:1 to balance the percentage of capped products with the efficiency of the transcription reaction, preferably a ratio of cap analog:GTP of 4:1-5:1 is used. In this context it is particularly preferred to use 5.8 mM Cap analog and 1.45 mM GTP if ATP, UTP and CTP are used in a concentration of 4 mM. $MgCl_2$ can optionally be added to transcription reaction. Preferred is a concentration of 1-100 mM. Particularly preferred is a concentration of 5-30 mM and most preferably 24 mM $MgCl_2$ is used.

Spermidine can optionally be added to the transcription reaction, preferably 1-10 mM, most preferably 2 mM spermidine.

Dithiothreitol (DTT) can optionally be added to the transcription reaction, preferably at a concentration of 1-100 mM, more preferably 10-100 mM, most preferably 40 mM.

An RNase inhibitor can optionally be added to the transcription reaction, preferably 0.1-1 U/µl, most preferably 0.2 U/µl.

*E. coli* pyrophosphatase can optionally be added to the transcription reaction, preferably in a concentration of 1-10 U/µg template DNA, and most preferably in a concentration of 5 U/µg template DNA. This ensures that magnesium, which is essential for transcription, remains in solution and does not precipitate as magnesium pyrophosphate.

The following viral DNA-dependent RNA polymerases can be used: T3, T7 and Sp6 polymerases. 1-1000 Units/µg DNA can be used. Preferably in a concentration of 100 U/µg DNA.

BSA can optionally be used, preferably in a concentration of 1-1000 µg/ml, most preferably in a concentration of 100 µg/ml. Most preferably, BSA is not present in the transcription reaction.

Most preferably, the in vitro transcription reaction comprises the following components:

1 µg linearized plasmid DNA
4 mM ATP, CTP and UTP
1.45 mM GTP,
5.8 mM CAP analogue
80 mM HEPES
24 mM $MgCl_2$
2 mM Spermidine
40 mM DTT
5 u pyrophosphatase
4 u RNase inhibitor
100 u T7 RNA polymerase The in vitro transcription reaction is preferably incubated at 37° C., more preferably for at least 4 hours.

Purification of the In Vitro Transcribed RNA:

Removal of Template DNA:

The template DNA is preferably removed from the in vitro transcription, e.g., the DNA template is separated from the RNA transcript. In one embodiment, the RNA transcript is removed chromatographically using a polyA capture, e.g., oligo dT, based affinity purification step. The RNA transcript binds affinity substrate, while the DNA template flow through and is removed.

In one embodiment, the polyA capture based affinity purification is oligo dT purification. For example, a polythymidine ligand is immobilized to a derivatized chromatography resin. The mechanism of purification involves hybridization of the polyA tail of the RNA transcript to the oligonucleotide ligand. The DNA template will not bind. In addition, RNA transcripts that do not contain PolyA stretches (short aborts and other truncates formed during in vitro transcription) will not bind to the resin and will not form a duplex with the affinity ligand. Polyadenylated RNA can then be eluted from the resin utilizing a low ionic strength buffer or a competitive binding oligonucleotide solution. A one pot purification method can yield highly purified poly A containing RNA with recoveries >80% actively removes endotoxin, DNA template, and enzymes utilized in the production of RNA using a simple capture and elute methodology with no subsequent fraction of captured poly A containing RNA. This purification increases mRNA product purity and in turn significantly increases target protein expression.

Particularly preferred is the enzymatic removal of DNA template using DNAse I.

Following transcription, the DNA template can be removed using methods known in the art comprising DNase I digestion. Such step additionally removes residual bacterial genomic DNA.

In this context, it is particularly preferred to add 6 µl DNAse I (1 mg/ml) and 0.2 µl $CaCl_2$ solution (0.1 M)/µg DNA template to the transcription reaction, and to incubate it for at least 3 h at 37° C.

Enzymatic Capping:

In a preferred embodiment, the RNA obtained by the inventive method may further be capped. As an alternative to co-transcriptional capping using CAP analogs, the RNA may be capped enzymatically.

Capping may be performed either before or after purification of the RNA transcript.

For large scale manufacturing, 5' capping of RNA transcripts is typically performed using a chemical cap analog. This is performed co-transcriptionally where the cap analog:GTP molar ratio in the reaction is ~4:1. This typically results in ~80% capping efficiency, as well as reduced RNA transcript yields due to consumption of GTP. This high abundance of uncapped species is undesirable when developing therapeutic RNA. Since only capped mRNA is translated into protein, the presence of a high abundance of uncapped species (ie 20%) is problematic as efficacy (protein production/mg RNA) is reduced by 20%> and 20%> of the final drug substance is an inert impurity, decreasing process productivity.

In a preferred embodiment, following RNA purification (e.g. LiCl precipitation), a 5' Cap can enzymatically added to the RNA transcript (if no Cap analog has been used in the in vitro transcription mix).

Optionally, recombinant Vaccinia Virus Capping Enzyme and recombinant 2'-O-methyltransferase enzyme can create a canonical 5'-5'-triphosphate linkage between the 5'-terminal nucleotide of an RNA and a guanine cap nucleotide wherein the cap guanine contains an N7 methylation and the 5'-terminal nucleotide of the RNA contains a 2'-O-methyl. Such a structure is termed Cap1 structure.

In a preferred embodiment, a natural Cap0/Cap1 structure is post-transcriptionally added to the RNA using vaccinia virus capping enzyme, (and potentially 2'-O-Methyltransferase) GTP and the Methyl donor SAM in suitable buffer conditions.

Kits comprising capping enzymes are commercially available (e.g. ScriptCap™ Capping Enzyme and Script-Cap™ 2'-O-Methyltransferase (both from CellScript)). Therefore, the RNA transcript is preferably treated according to the manufacturer's instructions.

In a preferred embodiment, RNA dissolved in WFI is first denatured at 65° C. for 10 minutes and then placed on ice. A capping reaction mixture is then prepared containing 0.6 g/l RNA, 1 mM GTP, 0.5 mM S-adenosyl-methionine (SAM), 0.4 units/µl Capping Enzyme, 4 units/µl 2'-O-Methyltransferase, 0.05 M Tris-HCl (pH 8.0), 6 mM KCl and 1.25 mM MgCl2 and added to the RNA. The capping reaction mixture is incubated at 37° C. for 60 min, adding a Cap1 to the RNA transcript.

Alternatively, only Capping Enzyme (without 2'-O-Methyltransferase) can be used to generate Cap0 structures.

The capping reaction is followed by precipitation or purification of the RNA transcript, preferably as described herein.

Enzymatic Polyadenylation:

In particular embodiments, the RNA obtained by the inventive method may further be polyadenylated.

Enzymatic Polyadenylation can be performed either before or after further purification of the RNA transcript.

The RNA transcript is incubated with a bacterial poly (A) polymerase (polynucleotide adenylyltransferase) e.g., from *E. coli* together with ATP in the respective buffers. The poly (A) polymerase catalyzes the template independent addition of AMP from ATP to the 3' end of RNA.

In a preferred embodiment the RNA transcript is reacted with *E. coli* poly(A) polymerase (e.g. from Cellscript) using 1 mM ATP at 37° C. for at least 30 min. Immediately afterwards, the RNA is purified according to the purification methods as described herein (e.g. LiCl purification). RNA is run on an agarose gel to assess RNA extension as described herein under section 'B. Quality Control 2'.

Quality Control: Size Determination of Poly-A-Tail

Determination of the Poly-A-Tail Length Via polyA Binding Protein Assay:

The poly(A) length is preferably determined in units of or as a function of polyA binding protein binding. In this embodiment, the polyA tail is long enough to bind at least 4 monomers of polyA binding protein. PolyA binding protein monomers bind to stretches of approximately 38 nucleotides. As such, it has been observed that polyA tails of about 80 nucleotides and 160 nucleotides are functional.

Other Poly(A) Tail Assays:

Three methods for measuring the length of a poly(A) tail are presented herein as exemplary methods: the poly(A) length assay, the ligation-mediated poly(A) test (LM-PAT), and the RNase H assay. The first two methods are PCR-based assays involving cDNA synthesis from an oligo(dT) primer. The third method involves removing the poly(A) tail from the mRNA of interest. A major obstacle to studying the enzymatic step of mammalian mRNA decay has been the inability to capture mRNA decay intermediates with structural impediments such as the poly(G) tract used in yeast. To overcome this, we combined a standard kinetic analysis of mRNA decay with a tetracycline repressor-controlled reporter with an Invader RNA assay. The Invader RNA assay is a simple, elegant assay for the quantification of mRNA. It is based on signal amplification, not target amplification, so it is less prone to artifacts than other methods for nucleic acid quantification. It is also very sensitive, able to detect attomolar levels of target mRNA. Finally, it requires only a short sequence for target recognition and quantitation. Therefore, it can be applied to determining the decay polarity of a mRNA by measuring the decay rates of different portions of that mRNA.

Purification of In Vitro Transcribed RNA:

In a particularly preferred embodiment, the inventive method comprises at least one step of purifying the RNA obtained by in vitro transcription in step b) of the inventive method. In the following, exemplary purification steps are described, which may be used in preferred embodiments of the invention.

RNA purification may include any purification method known in the art such as alcohol precipitation, chromatography, or LiCl precipitation.

LiCl Precipitation:

LiCl precipitation is particularly preferred.

High-molar LiCl solution is added to specifically precipitate the RNA transcript. Following precipitation the RNA transcript is re-suspended in water for injection.

LiCl precipitation is preferably performed by adding 50% of the volume 8M LiCl. The reaction is mixed and incubated at room temperature. Subsequently the reaction is centrifuged, the supernatant discarded and the RNA pellet washed with 75% ethanol. After drying, the RNA is preferably resuspended in water.

This step also further ensures the removal of proteins from previous manufacturing steps, including *E. coli* proteins, restriction enzymes, RNA polymerase, RNase inhibitor, DNase I, and BSA. Moreover, the RNA-specific precipitation also removes contamination with residual plasmid DNA and bacterial (genomic) DNA.

Purification by HPLC

According to another embodiment, the purification of the RNA transcript by HPLC is particularly preferred.

HPLC (abbreviation for "High Performance (High Pressure) Liquid Chromatography") is an established method of separating mixtures of substances, which is widely used in biochemistry, analytical chemistry and clinical chemistry. An HPLC apparatus consists in the simplest case of a pump with eluent reservoir containing the mobile phase, a sample application system, a separation column containing the stationary phase, and the detector. In addition, a fraction collector may also be provided, with which the individual fractions may be separately collected after separation and are thus available for further applications.

Reversed phase HPLC consists of a non-polar stationary phase and a moderately polar mobile phase. One common stationary phase is e.g. silica, which has been treated with $RMe_2SiCl$, where R is a straight chain alkyl group such as $C_{18}H_{37}$ or $C_8H_{17}$. The retention time is therefore longer for molecules, which are more non-polar in nature, allowing polar molecules to elute more readily. Retention time is increased by the addition of polar solvent to the mobile phase and decreased by the addition of more hydrophobic solvent.

The product RNA can be purified from various contaminations from previous manufacturing steps. These include buffer contaminations, protein impurities (*Escherichia coli* proteins, Restriction enzymes, T7-RNA-Polymerase, RNase-Inhibitor, DNase I, and BSA), impurities from RNA-RNA hybrids, from DNA-RNA hybrids or their fragments, from pDNA contaminations and bacterial genomic DNA contaminations, and solvent contaminations (Acetonitrile, Chloroform, TEAA, 2-Propanol and Phenol) and free nucleotides.

Moreover, size exclusion occurs during that procedure (smaller and larger RNAs can be excluded).

The RNA obtained in step b) of the inventive method is preferably purified by a size-selective HPLC based technique. Moreover, it allows monitoring structural and size heterogeneity. The purified mRNA is preferably concentrated by alcohol precipitation and re-suspended in water for injection.

Particularly preferred is a RP-HPLC method as described in WO2008077592, which preferably comprises the following components:

PLRP-S 4000 Å 8 µm 50×25 mm column crosslinked macroporous poly(styrene/divinylbenzene) reversed phase packing Reagents:

Eluent A (100 mM Triethylammoniumacetat in WFI, pH 7.0 (+/−0.5))

Eluent B (100 mM Triethylammoniumacetat in 25% acetonitrile, pH 7.0 (+/−0.5)) 1M Triethylammoniumacetat Alternatives for (Common) HPLC: Ion/Anion Exchange HPLC AEX chromatography is an alternative method of purification that leverages ionic interaction between positively charged sorbents and negatively charged molecules. AEX sorbents typically include a charged functional group crosslinked to solid phase media. Ion exchange chromatography for preparative RNA transcript also provides a solution that allows for separations of longer RNA transcripts, including lengths of up to at least 10,000 nucleotides. In addition, the methods allow for separations of chemically modified RNA transcripts (WO2014144767A1).

A sample comprising the RNA transcript is preferably contacted with an ion exchange sorbent comprising a positively-charged functional group linked to solid phase media, and the sample is delivered with at least one mobile phase, where the RNA transcript in the sample binds the positively-charged functional group of the ion exchange sorbent. In one embodiment, the sample is delivered under denaturing conditions, for example, the sample can be contacted with urea. In other embodiments, the mobile phase is a Tris-EDTA-acetonitrile buffered mobile phase, or there are two mobile phases made of Tris-EDTA-acetonitrile. In other embodiments, the mobile phase comprises a chaotropic salt, such as sodium perchlorate. The ion exchange sorbent elutes a portion of the sample comprising the RNA transcript and one or more separate portions of the sample comprising any impurities. At least one aspect of the portion of the sample comprising the RNA transcript and the separate portions of the sample comprising the impurities are then analyzed, where the aspect is charge heterogeneity of the RNA transcript, mass heterogeneity of the RNA transcript, process intermediates, impurities, or degradation products. The RNA transcript is then characterized by using the analysis to determine the charge heterogeneity of the RNA transcript.

Affinity Purification (Oligo-dT)

In one embodiment, the poly A capture based affinity purification is oligo dT purification. For example, a polythymidine ligand is immobilized to a derivatized chromatography resin. The mechanism of purification involves hybridization of the poly A tail of the RNA transcript to the oligonucleotide ligand. The DNA template will not bind. In addition, RNA transcripts that do not contain Poly A stretches (short aborts and other truncates formed during in vitro transcription) will not bind to the resin and will not form a duplex with the affinity ligand. Poly adenylated RNA can then be eluted from the resin utilizing a low ionic strength buffer or a competitive binding oligonucleotide solution. A one pot purification method can yield highly purified poly A containing RNA with recoveries >80% actively removes endotoxin, DNA template, and enzymes utilized in the production of RNA using a simple capture and elute methodology with no subsequent fraction of captured poly A containing RNA. This purification increases mRNA product purity and in turn significantly increases target protein expression.

Hydroxyapatite Chromatography

Purification of RNA transcript is described in WO2014140211.

Hydroxyapatite chromatography involves hydroxyapatite as stationary phase. Hydroxyapatite is a form of calcium phosphate having the chemical formula $Ca_5(PO_4)_3(OH)$. Hydroxyapatite chromatography of nucleic acids is believed to exploit the charge interaction between their negatively charged phosphate backbone and the positively charged calcium ions on the surface of the hydroxyapatite medium. Differential elution {e.g. to separate protein, DNA and undesired RNA species from desired RNA species) is accomplished by the application of an increasing phosphate gradient. Phosphate ions present in the buffer compete with the phosphate groups of the retained nucleic acid species for calcium on the hydroxyapatite medium, thus allowing separation by selective elution of molecules. In this mixed mode chromatography, the binding is a balance of attraction of the RNA phosphate backbone to the calcium ions of the hydroxyapatite medium and repulsion of the RNA phosphate backbone from the phosphate of the hydroxyapatite medium. Compared to ion exchange chromatography, the strength of the binding on a hydroxyapatite medium is dependent on charge density rather than total charge. This important difference allows for the separation of molecules upon their charge density (e.g. RNA vs DNA vs proteins) and the binding and elution of RNA regardless of its total charge, and therefore regardless of its length. Therefore this method can be used for the purification of RNA molecules of any length. The fractionation of nucleic acids using hydroxyapatite was described in the 1960s (Bernardi et al. 1965). This approach has been exploited for applications including isolation and separation of viral RNA, dsDNA and ssDNA from environmental samples (Andrews-Pfannkoch et al. 2010), separation of DNA and RNA from tissue-extracted nucleic acids (Beland et al. 1979) and separation of DNA for hybridization studies (Kamalay et al. 1984).

Core Bead Chromatography (does not Require Prior DNA Digest)

Purification of RNA transcript by core bead chromatography is described in WO 2014140211A1.

Preferably, RNA is selectively recovered from the column in the flow-through. Proteins and short nucleic acids are retained in the beads. Flow-through fractions containing RNA may be identified by measuring UV absorption at 260 nm. The composition comprising the RNA of interest collected in the flow-through is highly purified relative to the preparation before the core bead chromatography step. Multiple eluted fractions containing the RNA of interest may be combined before further treatment. An exemplary core bead flow-through chromatography medium is Capto™ Core 700 beads from GE Healthcare. Suitable chromatography setups are known in the art, for example liquid chromatography systems such as the AKTA liquid chromatography systems from GE Healthcare.

Parameters can be set in a way that pDNA and proteins are captured in the beads, and RNA products flow through. Afterwards, HPLC purification can be conducted to get rid of RNA fragments etc.

Alternatively or additionally the RNA is recovered by other purification methods (e.g. affinity chromatography, size exclusion chromatography, anion exchange chromatography, etc.)

In one embodiment purification of the RNA transcript by LiCl precipitation, RP-HPLC using a crosslinked macroporous poly(styrene/divinylbenzene) reversed phase and subsequent isopropanol precipitation using $Na^+$ as monovalent cation is particularly preferred.

Lyophilization of the Purified RNA Transcript:

In a particularly preferred embodiment, the RNA transcript is lyophilized after purification by any lyophilization method known in the art. Lyophilization of the RNA transcript particularly increases the half-life of the RNA.

Resuspension of Lyophilized RNA and Adjustment of the RNA Concentration:

The resuspension is preferably performed using the respective amount of WFI-water (water for injection) or pyrogen free water at RT. The final concentration is set, and the medicament is sterile-filtered, preferably through a pore size 0.22 μm, for bioburden reduction. A sample of the produced RNA solution is used for photometric determination of the RNA content. Eventually, the RNA-solution is sterile filtered. For long-term storage, the sterile-filtered, concentration-adjusted RNA solution is stored at −80° C.

The RNA solution is resuspended in a concentration of 0.1-50 g/l, more preferably in a concentration of 1-20 g/l, more preferably in a concentration of 1-10 g/l and most preferably in a concentration of 5 g/l.

B. Quality Control 2

In the following section (section B and subsections), preferred steps are described for controlling the quality of the RNA obtained by the inventive method. Any of the steps described herein may be applied to any quality control carried out at any stage of the method. Preferably, the steps may independently be applied to the final RNA product as well as to intermediates (such as the raw RNA obtained in the in vitro transcription reaction). In particular, this section relates to preferred steps for determination of RNA identity, determination of RNA integrity and/or determination of the purity of the RNA preparation.

B.1 Determination of the RNA Concentration/RNA Content/RNA Amount

The RNA content is preferably determined by spectrometric analysis.

Spectrophotometric analysis is based on the principles that nucleic acids absorb ultraviolet light in a specific pattern. In the case of DNA and RNA, a sample that is exposed to ultraviolet light at a wavelength of 260 nanometers (nm) will absorb that ultraviolet light. The resulting effect is that less light will strike the photodetector and this will produce a higher optical density (OD).

An optical density of 1 measured at 260 nm corresponds to a concentration of 40 μg/ml single stranded RNA.

The yield of the test transcription is evaluated measurement of the absorption at 260 nm (OD260).

B.2 Determination of RNA Identity

B.2.1 Determination of Transcript Length and Transcript Uniqueness

The correct transcript length and transcript uniqueness is preferably confirmed in order to verify identity and purity of the RNA obtained in step b) of the inventive method.

The band uniqueness and band size of mRNA is preferably analyzed by agarose gel electrophoresis, capillary gel electrophoresis, polyacrylamide gel electrophoresis or HPLC.

Particularly preferred is agarose gel electrophoresis.

Electrophoresis through agarose gels is a method to separate RNA. The RNA can be determined in the agarose gel by addition of the fluorescent intercalating dye ethidium bromide or other commercially available dyes (SybrSafe DNA stain, Cybr Green, Orange DNA loading dye)

As running usually 1×MOPS buffer is used (MOPS, 0.74% Formaldehyde, in ultra-pure water)

For the preparation of the agarose gel, 0.5-3% (w/v) agarose or more preferably 1.2% (w/v) agarose is melted in 1× running buffer.

The solution is poured into a mold and allowed to harden. When an electric field is applied across the gel, RNA, which is negatively charged, migrates to the anode. As running buffer the same buffer as used for preparation of the agarose gel is used.

Loading buffer (e.g. Gel loading buffer with ethidium bromide (10 mg/l)) is added to the sample and loaded on the agarose gel. After gel running the RNA can be determined, for example, by ultraviolet light. The RNA length can be compared to the predicted length and therefore allows the determination if the correct DNA sequence encoding the target RNA sequence is integrated into the plasmid.

Alternatively, polyacrylamide gel electrophoresis, capillary gel electrophoresis, or HPLC may be used.

B.2.2 Determination of RNA Identity by RNAse Treatment with Subsequent Analysis of the Degraded Product In a preferred embodiment, RNA identity is confirmed by a test, which uses RNAse A digestion of a sample of the RNA obtained in step b) of the inventive method. The digested RNA is preferably compared with an untreated sample on an RNA gel electrophoresis.

In this context, it is particularly preferred to digest 1 µg RNA transcript with 10 µg RNAse A.

B.2.3 Determination of RNA Identity by RT-PCR with Subsequent Analysis of the Product Via-Agarose Gelelectrophoresis In a first step, the RNA is preferably converted into complementary DNA (cDNA) using the enzyme reverse transcriptase. In a second step, the resulting cDNA is amplified via PCR (polymerase chain reaction) using appropriate primers to provide a PCR product of a certain size. The PCR product is analyzed via agarose gel electrophoresis for correct band size.

RT-PCR using the RNA as a template is preferably used to determine the size of the RNA product. For reverse transcription, kits are commercially available.

Afterwards, produced cDNA is amplified with target-specific primers and product band sizes are analysed in a conventional DNA agarose gel electrophoresis, preferably as described in the context of Quality Control 1.

B.2.4 Determination of RNA Identity by Reverse Transcription Sequencing:

The RNA transcript can be characterized by reverse transcription sequencing. The RNA product is incubated with a common reverse transcriptase, a set of primers, and dNTPs to obtain cDNA samples. The cDNA serve as a template for PCR to amplify the cDNA. The PCR product is then characterized by analysis using a sequencing procedure as defined herein such as Sanger sequencing or bidirectional sequencing.

B.2.5 Determination of RNA Identity by Oligonucleotide Mapping:

The RNA obtained in step b) of the inventive method is preferably incubated with various nucleotide probes under conditions sufficient to allow hybridization of the probes to the RNA to form duplexes, where each of the nucleotide probes includes a sequence complementary to a different region of the RNA transcript.

The formed duplexes are then contacted with an RNase (such as RNase H or RNase TI) under conditions sufficient to allow RNase digestion of the duplexes to form reaction products.

Next, the reaction products are analyzed, for example by using a procedure such as reverse phase high performance liquid chromatography (RP-HPLC), anion exchange HPLC (AEX), or RP-HPLC coupled to mass spectrometry (MS). Finally, the RNA is characterized by using the analysis of the reaction products to determine the sequence of the RNA.

B.2.6 Determination of RNA Identity by RNA Sequencing.

In a preferred embodiment, the identity of the RNA may be determined by RNA sequencing. Methods for RNA sequence analysis are known in the art and may be used herein.

B.3 Determination of RNA Integrity

The relative integrity of the RNA obtained in step b) of the invention is preferably determined as the percentage of full-length RNA (i.e. non-degraded RNA) with respect to the total amount of RNA (i.e. full-length RNA and degraded RNA fragments (which appear as smears in gel electrophoresis)).

B.4 Determination of pH

Potentiometric determination of the pH content using a conventional volt-meter, according to the european pharmacopedia (PhEur) 2.2.3 is preferably used to determine the pH value in the RNA preparation.

B.5 Determination of Osmolality

In a preferred embodiment, the osmolality of the RNA obtained in step b) of the inventive method is determined. The measurement of the osmolality is performed using a conventional osmometry device according to PhEur 2.2.35.

B.6 Determination of Bioburden/Microbial Content

To determine sterility of the RNA preparation, an RT-PCR using universal bacterial primers (detecting universal occurring genes in bacteria) may be performed. Moreover, a plating assay may be conducted.

Particularly Preferred is a Plating Assay According to PhEur 2.6.12.:

For determination of the bioburden the presence/absence of bacteria is tested under aerobe and anaerobe conditions after plating the RNA on agar- and/or glucose plates and incubation for several days (e.g. 5 and 7 days, respectively). The bioburden is assessed by counting the bacteria clones grown on bacteria plates.

For this purpose, different media for plating can be used. Tryptic Soy Agar (TSA) (Soybean Casein Digest Agar (CSA)) and Sabouraud Glucose (2%) Agar plates are particularly preferred.

B.7 Determination of Endotoxin Contamination:

A test for bacterial endotoxins is preferably used to detect or quantify endotoxins of gram-negative bacterial origin by using amoebocyte lysate from horseshoe crab (*Limulus polyphemus* or *Tachypleus tridentatus*). The principle has been discovered by Levin (Levin, J. 1979. The reaction between bacterial endotoxin and amebocyte lysate, p. 131-146. In E. Cohen (ed.), Biomedical Applications of the Horseshoe Crab (Limulidae), Progress in Clinical and Biological Research, Vol. 29. Alan R. Liss, Inc., NewYork).

In general, there are 3 techniques for performing this test: the gel-clot technique, which is based on gel formation; the turbidimetric technique, based on the development of turbidity after cleavage of an endogenous substrate; and the chromogenic technique, based on the development of colour after cleavage of a synthetic peptide-chromogen complex Preferred is the LAL-test. The amount of endotoxins per volume of RNA is determined and evaluated via kinetic-turbidometric LAL (*Limulus*-Amoebocyte-Lysate) test according to Ph. Eur. 2.6.14 (Pharmacopoea Europaea).

B.8 Determination of Protein Contamination:

The total protein content per volume of RNA obtained in step b) of the inventive method is calculated.

Several different methods in the art are known for detection of protein, including UV absorbance measurements at 280 nm (due to the presence of aromatic amino acids), the Lowry assay, the Biuret assay, the Bradford assay, and the BCA (Bichinonic Acid) assay.

The BCA (Bichinonic Acid) assay, a colorimetric method of detection based on complexation of proteins with copper and BCA. The total protein concentration contained in the RNA is measured via absorption at 562 nm compared to a protein standard (BSA). The principle of the bicinchoninic acid (BCA) assay is similar to the Lowry procedure (Lowry, O. H. et al, J. Biol. Chem., 193, 265-275 (1951)). Both rely on the formation of a $Cu^{2+}$-protein complex under alkaline conditions, followed by reduction of the $Cu^{2+}$ to $Cu^+$. The amount of reduction is proportional to the protein present. It has been shown that cysteine, cystine, tryptophan, tyrosine, and the peptide bond are able to reduce $Cu^{2+}$ to $Cu^+$. BCA forms a purple-blue complex with $Cu^+$ in alkaline environments, thus providing a basis to monitor the reduction of alkaline $Cu^{2+}$ by proteins at absorbance maximum 562 nm.

Another method which could be used for the determination of protein is the Bradford method. The Bradford assay, a colorimetric protein assay, is based on an absorbance shift of the dye Coomassie Brilliant Blue G-250 in which under acidic conditions the red form of the dye is converted into its bluer form to bind to the protein being assayed. The (bound) form of the dye has an absorption spectrum maximum historically held to be at 595 nm. The cationic (unbound) forms are green or red. The binding of the dye to the protein stabilizes the blue anionic form.

The increase of absorbance at 595 nm is proportional to the amount of bound dye, and thus to the amount (concentration) of protein present in the sample.

Particularly preferred is the BCA assay. For performing a BCA assay, several commercially available kits may be used.

B.9 Determination of Plasmid DNA Contamination:

Residual plasmid DNA may optionally be detected by PCR or quantitative PCR as described herein using specific primers and probes for DNA plasmid used for in vitro transcription. Particularly preferred is the detection of residual plasmid DNA via quantitative PCR as described herein using specific primers and probes for the ampicillin gene hosted in the production vector. The probes are used as positive control and thus for calculation of the plasmid DNA concentration.

The use of following primers and probes are particularly preferred:

```
Sense-Primer bla13U:
GATACCGCGAGACCCAC              (SEQ ID NO: 12)

Antisense-Primer bla355L:
GGAACCGGAGCTGAATG              (SEQ ID NO: 13)

Probe BL04FL:
GCCAGCCGGAAGGGCC-FL            (SEQ ID NO: 14)

Probe BL04LC:
LC Red640-GCGCAGAAGTGGTCCTGCA-Ph  (SEQ ID NO: 15)
```

B.10 Determination of Bacterial DNA Contamination:

Residual bacterial DNA may optionally be detected e.g. by PCR or quantitative PCR using specific primers and probes for bacterial genomic sequences. Particularly preferred is the detection of residual bacterial DNA is detected via quantitative PCR using specific primers and probes for the *E. coli* gene uidA. The probes are preferably used as positive control and thus for calculation of the bacterial DNA concentration.

The following primers and probes are preferably used for the quantitative PCR:

```
Primer EC 679U:
GGACAAGGCACTAGCG               (SEQ ID NO: 8)

Primer EC 973 L:
ATGCGAGGTACGGTAGGA             (SEQ ID NO: 9)

Probe EC1 FL:
CATCCGGTCAGTGGCAGT-FL          (SEQ ID NO: 10)

Probe EC1 LC:
LC640-AAGGGCGAACAGTTCCTGA-ph   (SEQ ID NO: 11)
```

B.11 Determination of Residual Solvent Contamination

Residual solvents are preferably analyzed based on the PhEur 2.2.28 method via headspace gas chromatography using the standard addition method. Samples are heated to 80° C., equilibrated, and the gas phase is injected and analyzed using FID (flame ionization detection).

The analysis preferably includes acetonitrile, chlorophorm, triethylammonium acetate (TEAA), isopropanol, and phenol.

In the following section, the present invention is further illustrated by particularly preferred embodiments, which are preferably characterized by the features as described in the following, wherein any one of said features may be combined with any other feature described herein.

According to a preferred embodiment, step a) of the inventive method comprises at least one of the following steps A) to K):

A) selection of a RNA sequence (to be produced by in vitro transcription);

B) reverse transcription of the target RNA sequence;

C) synthesis of a plasmid template DNA comprising a nucleic acid sequence encoding the RNA sequence;

D) quality control of the plasmid template DNA: determination of the identity of the nucleic acid sequence encoding the RNA sequence;

E) transformation of the plasmid template DNA into bacteria;

F) fermentation;

G) quality control of the plasmid template DNA: yield estimation of the plasmid template DNA and determination of the identity of the nucleic acid sequence encoding the RNA sequence;

H) plasmid template DNA isolation (giga preparation)
I) quality control of isolated plasmid template DNA: determination of the identity of the nucleic acid sequence encoding the RNA sequence and determination of the purity of the plasmid template DNA preparation;
J) linearization of plasmid template DNA;
K) quality control of linearized plasmid template DNA, e.g. completeness of linearization, estimation of RNA yield and determination of RNA identity.

In a further preferred embodiment, step a) of the inventive method comprises the steps A) to K) as defined above, preferably in alphabetical order.

Preferably, step a) of the inventive method comprises a step I) as defined above, wherein the step I) comprises at least one of
i) photometric determination of the plasmid template DNA content;
ii) determination of RNA contaminations;
iii) determination of the identity of the nucleic acid sequence encoding the RNA sequence by restriction analysis of the test plasmid isolation
iv) determination of the identity of the nucleic acid sequence encoding the RNA sequence by sequencing of the insert DNA sequence
v) determination of the presence and/or the amount of an endotoxin;
vi) determination of protein content;
vii) determination of bioburden; and
viii) determination of bacterial DNA.

In addition or alternatively, step a) of the inventive method may comprise a step K) as defined above, wherein the step K) comprises at least one of
i) control of linearization;
ii) determination of RNA identity in test in vitro transcription by agarose gel electrophoresis; and/or
iii) determination of RNAse contaminations in linearized plasmid template DNA;

It is further preferred that step b) of the inventive method comprises at least one of the following steps L) to P)
L) in vitro transcription;
M) first purification of the in vitro transcribed RNA by precipitation, preferably LiCl-precipitation;
N) quality control of the in vitro transcribed RNA: determination of RNA identity
O) second purification of the in vitro transcribed RNA by preparative RP-HPLC and precipitation
P) quality control of the in vitro transcribed RNA: determination of RNA identity and RNA integrity,
wherein the identity and/or the integrity of the RNA are preferably determined via gel electrophoresis, more preferably agarose gel electrophoresis.

According to a particular embodiment, the inventive method comprises a step Q), which comprises lyophilization of the in vitro transcribed RNA, resuspension of the freeze-dried RNA and sterile filtration of the resuspended RNA. Preferably, the sterile filter used in step Q) is tested by carrying out a bubble-point test. More preferably, the RNA yield is determined photometrically after resuspending the RNA.

In another preferred embodiment, the inventive method comprises controlling the quality of the (final) product RNA by at least one step selected from the following steps i) to xi)
i) determination of RNA identity by RNAse digestion;
ii) determination of RNA identity by RT-PCR;
iii) determination of RNA identity and RNA integrity by agarose gel electrophoresis;
iv) determination of pH;
v) determination of osmolality;
vi) determination of bioburden;
vii) determination of endotoxins;
viii) determination of protein content;
ix) determination of plasmid template DNA;
x) determination of bacterial DNA and/or
xi) determination of the presence and/or the amount of an organic solvent (acetonitrile, chloroform, triethylammonium acetate (TEAA), isopropanol, and phenol).

More preferably, all of steps i) to xi) as defined above are employed, preferably in numerical order.

In a particularly preferred embodiment, the inventive method comprises the following steps:
A) selection of a RNA sequence (to be produced by in vitro transcription);
B) reverse transcription of the target RNA sequence;
C) synthesis of a plasmid template DNA comprising a nucleic acid sequence encoding the RNA sequence;
D) quality control of the plasmid template DNA: determination of the identity of the nucleic acid sequence encoding the RNA sequence
  i) by restriction analysis and/or
  ii) by sequencing of the nucleic acid sequence encoding the RNA sequence;
E) transformation of the plasmid template DNA into bacteria;
F) fermentation;
G) quality control of the plasmid template DNA: yield estimation of the plasmid template DNA and determination of the identity of the nucleic acid sequence encoding the RNA sequence;
  i) test plasmid template DNA isolation (mini preparation) and photometric determination of the plasmid template DNA content to estimate yield of plasmid template DNA and/or
  ii) determination of the identity of the nucleic acid sequence encoding the RNA sequence by restriction analysis of the test plasmid isolation
H) plasmid template DNA isolation (giga preparation)
I) quality control of isolated plasmid template DNA: determination of the identity of the nucleic acid sequence encoding the RNA sequence and determination of the purity of the plasmid template DNA preparation
  i) photometric determination of the plasmid template DNA content;
  ii) determination of RNA contaminations;
  iii) determination of the identity of the nucleic acid sequence encoding the RNA sequence by restriction analysis of the test plasmid isolation
  iv) determination of the identity of the nucleic acid sequence encoding the RNA sequence by sequencing of the insert DNA sequence
  v) determination of the presence and/or the amount of an endotoxin;
  vi) determination of protein content;
  vii) determination of bioburden; and/or
  viii) determination of bacterial DNA
J) linearization of plasmid template DNA;
K) quality control of linearized plasmid template DNA, e.g. completeness of linearization, estimation of RNA yield and determination of RNA identity:
  i) control of linearization;
  ii) determination of RNA identity in test in vitro transcription by agarose gel electrophoresis; and/or
  iii) determination of RNAse contaminations in linearized plasmid template DNA;

L) in vitro transcription;
M) first purification of the in vitro transcribed RNA by precipitation, preferably LiCl-precipitation;
N) quality control of the in vitro transcribed RNA: determination of RNA identity
   i) determination of RNA identity by agarose gel electrophoresis;
O) second purification of the in vitro transcribed RNA by preparative RP-HPLC and precipitation
P) quality control of the in vitro transcribed RNA: determination of RNA identity and RNA integrity
   i) determination of the RNA identity and RNA integrity by agarose gel electrophoresis;
Q) lyophilization of the in vitro transcribed RNA, resuspension of the freeze-dried RNA and sterile filtration of the resuspended RNA;
R) quality control: determination of the RNA yield
   i) photometric determination of RNA content and/or
   ii) bubble-point-test for control of the sterile filter;
S) end-product-control: Determination of RNA identity, RNA integrity and purity of in vitro transcribed RNA:
   i) determination of RNA identity by RNAse digestion;
   ii) determination of RNA identity by RT-PCR;
   iii) determination of RNA identity and RNA integrity by agarose gel electrophoresis;
   iv) determination of pH;
   v) determination of osmolality;
   vi) determination of bioburden;
   vii) determination of endotoxins;
   viii) determination of protein content;
   ix) determination of plasmid template DNA;
   x) determination of bacterial DNA and/or
   xi) determination of the presence and/or the amount of an organic solvent (acetonitrile, chloroform, triethylammonium acetate (TEAA), isopropanol, and phenol).

It is particularly preferred that the quality of the plasmid template DNA obtained in step J) above is controlled by carrying out a test in vitro transcription.

BRIEF DESCRIPTION OF THE FIGURES

The figures shown in the following are merely illustrative and shall describe the present invention in a further way. These figures shall not be construed to limit the present invention thereto.

FIGURES

Figure 1:
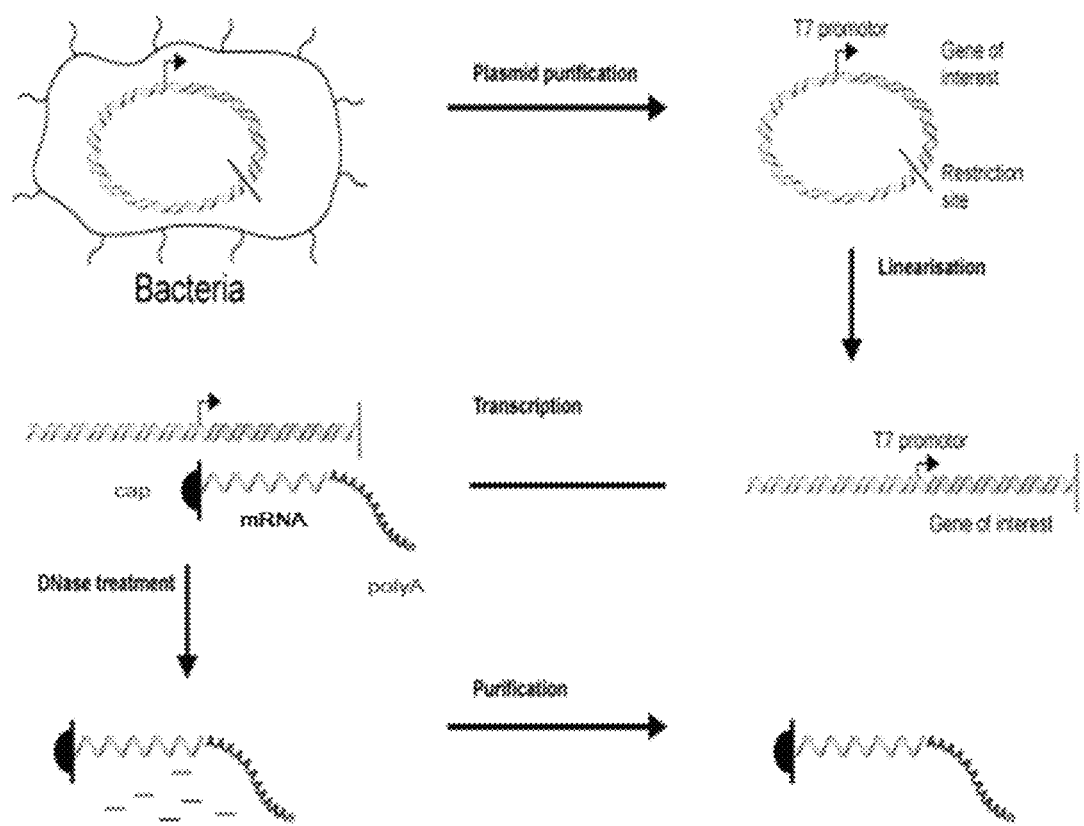
Figure 3:
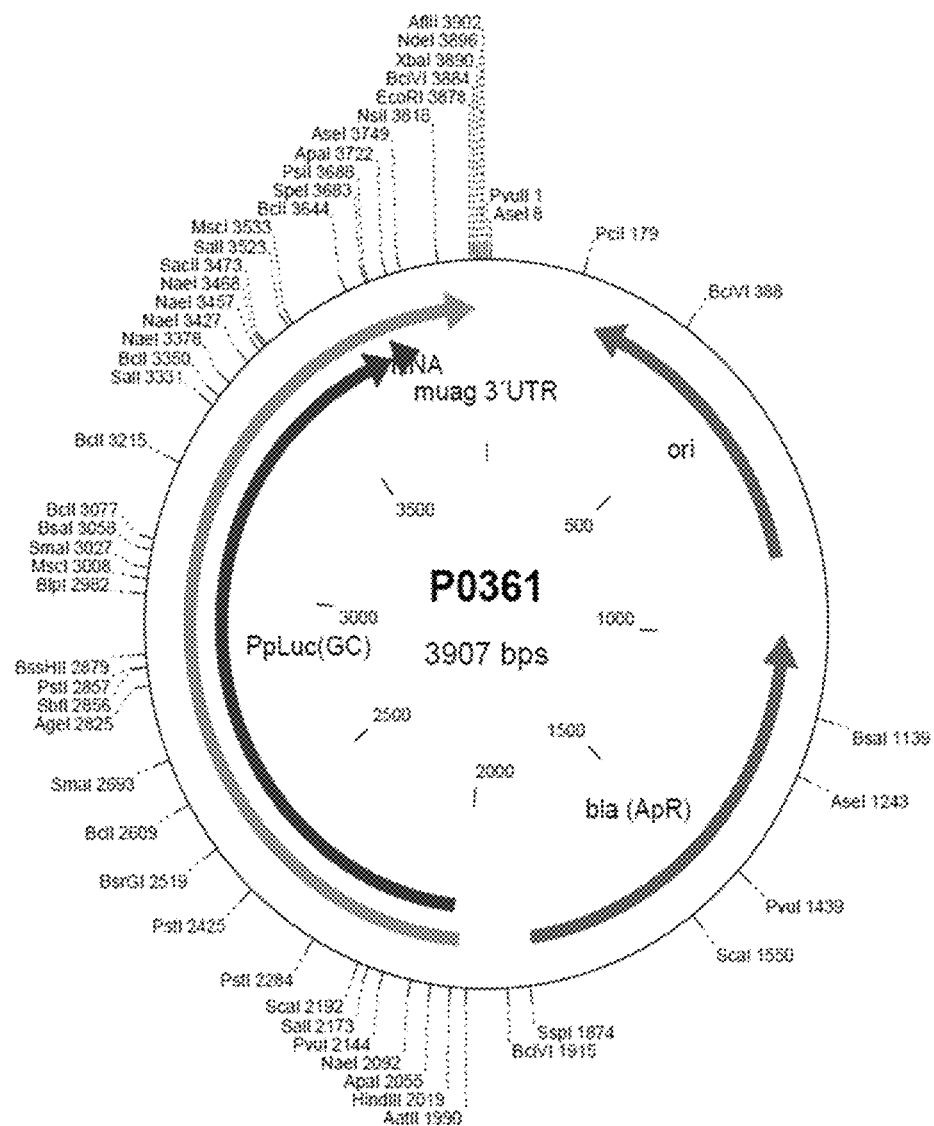
Figure 4:
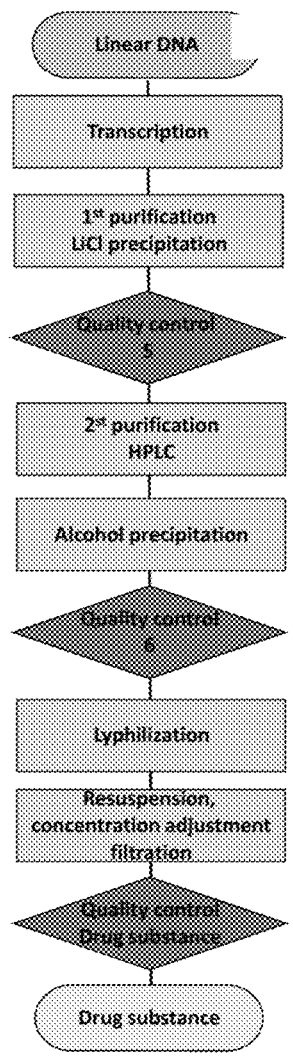
Figure 5:
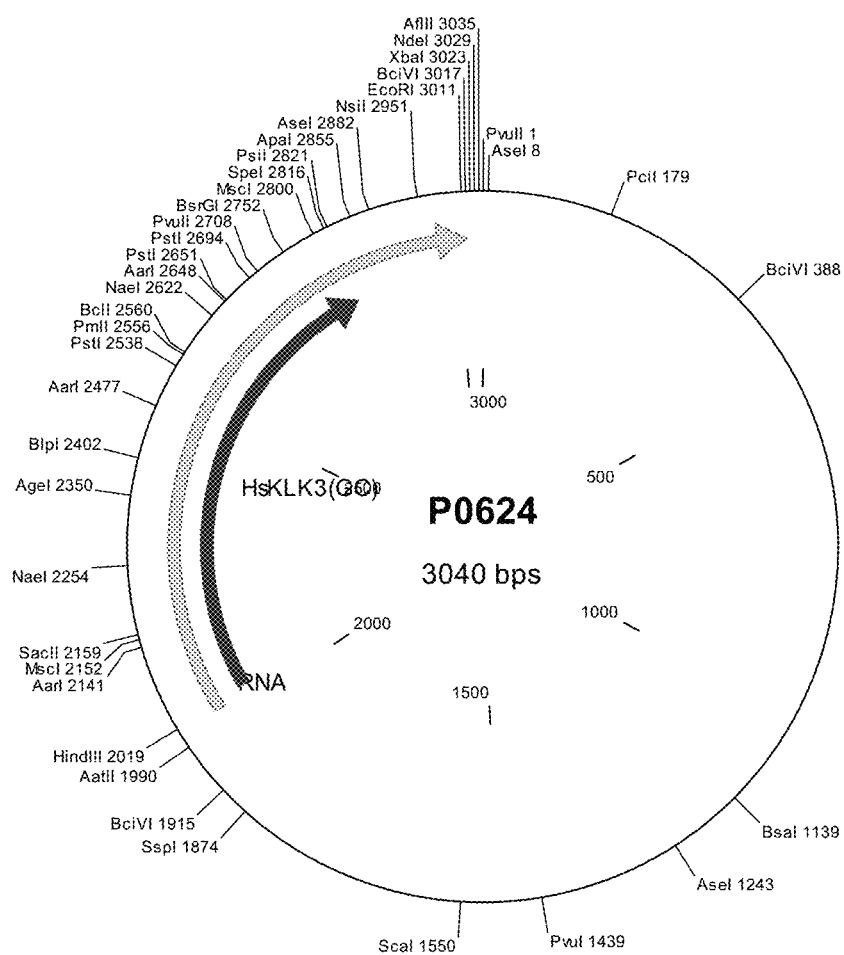
Figure 9:
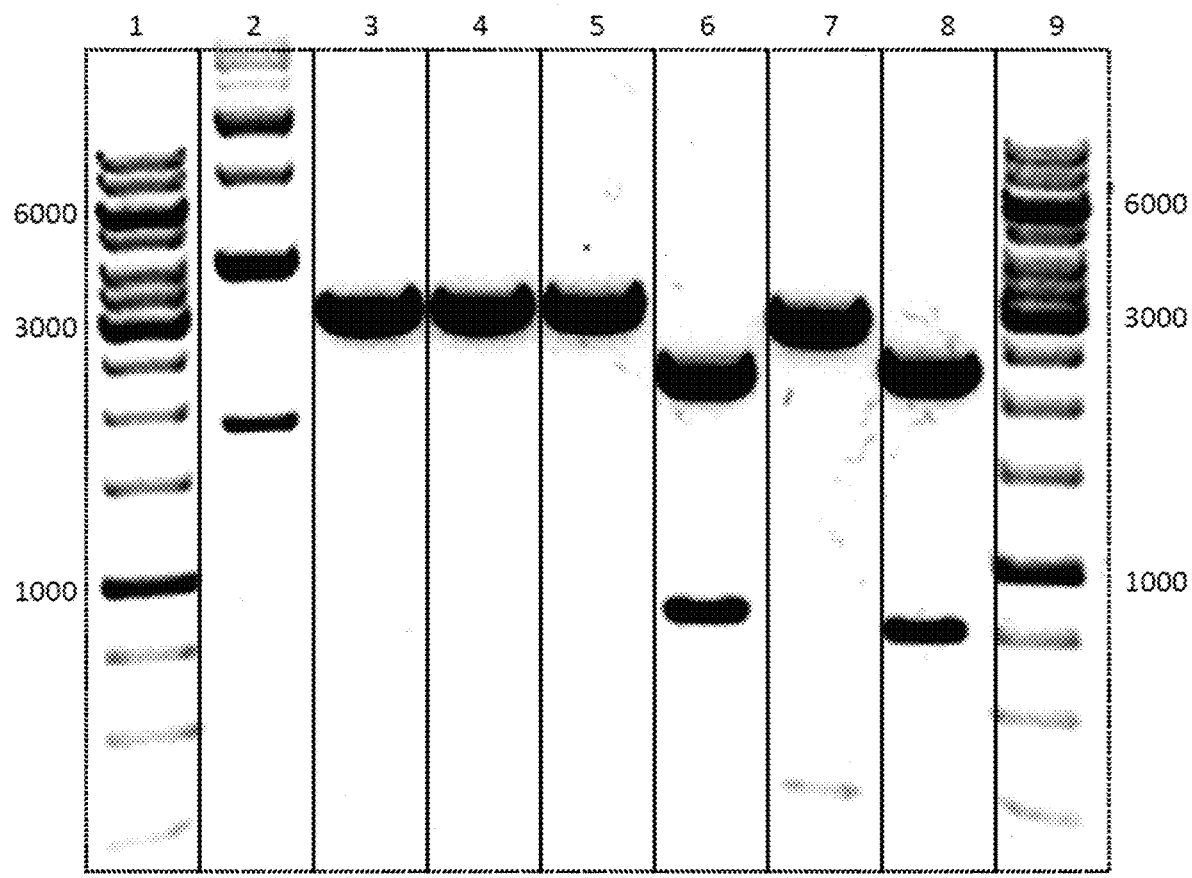
Figure 10:
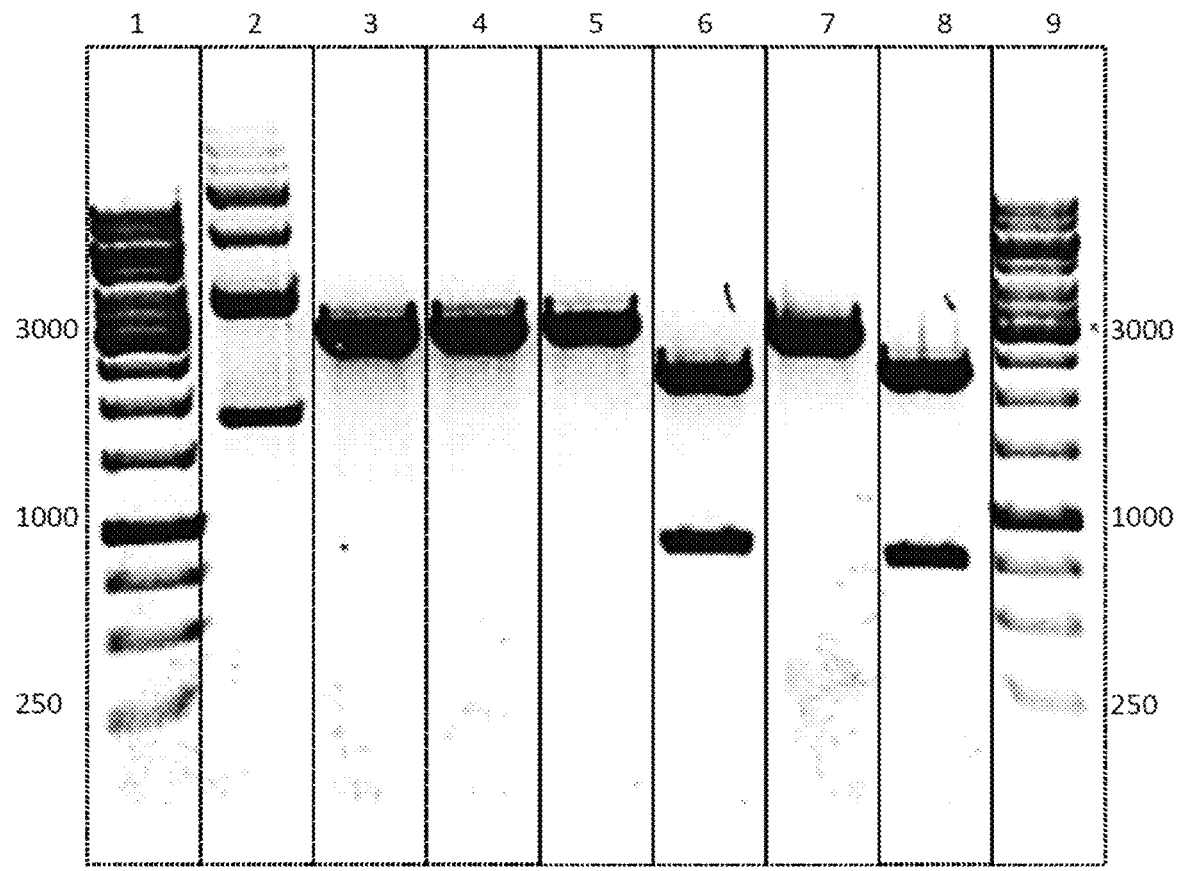
Figure 11:
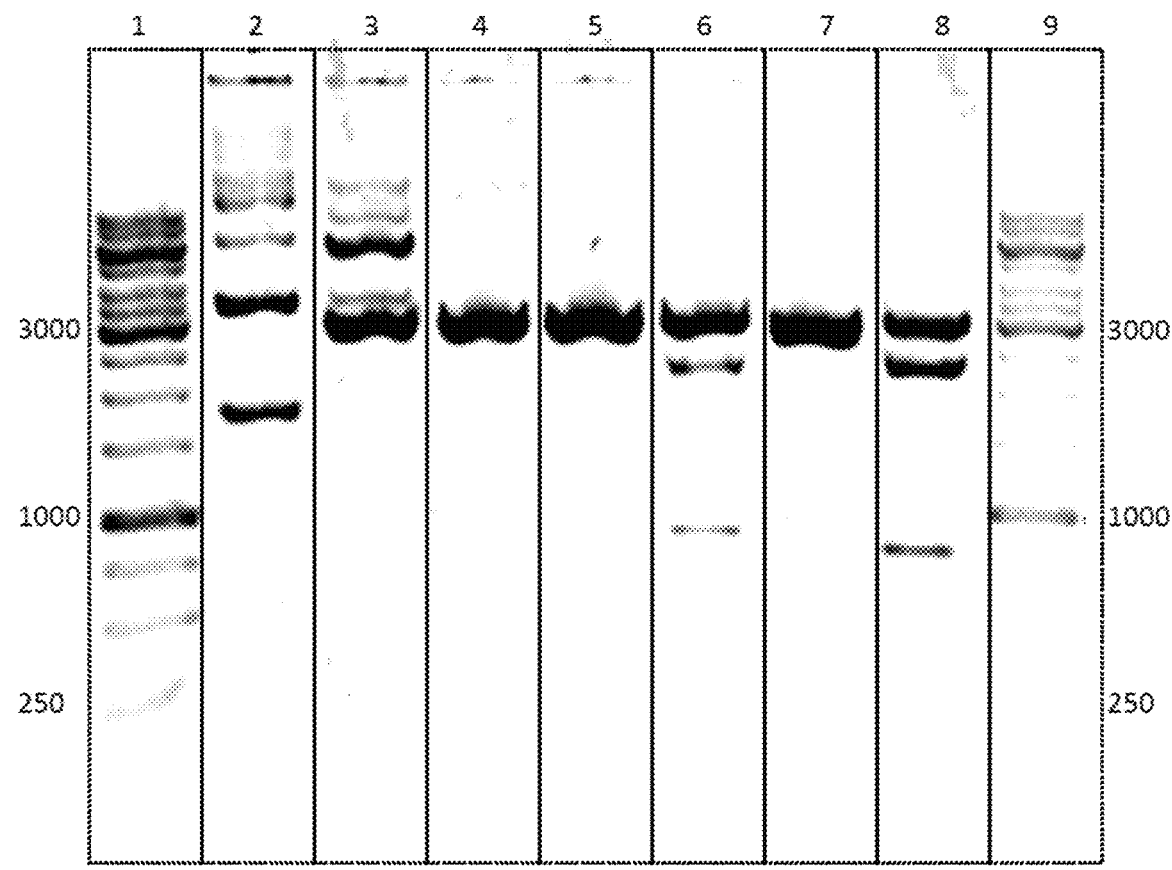
Figure 12:
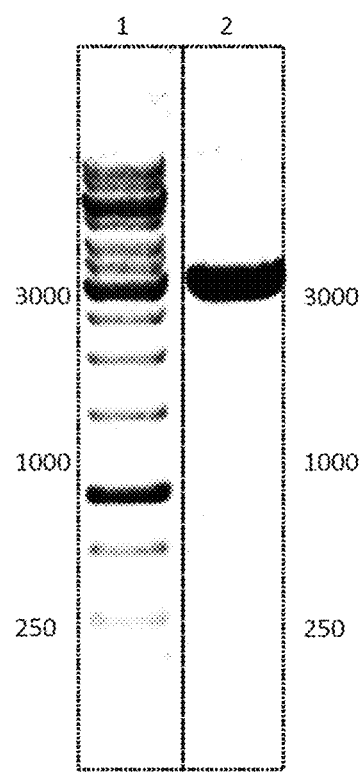
Figure 13:
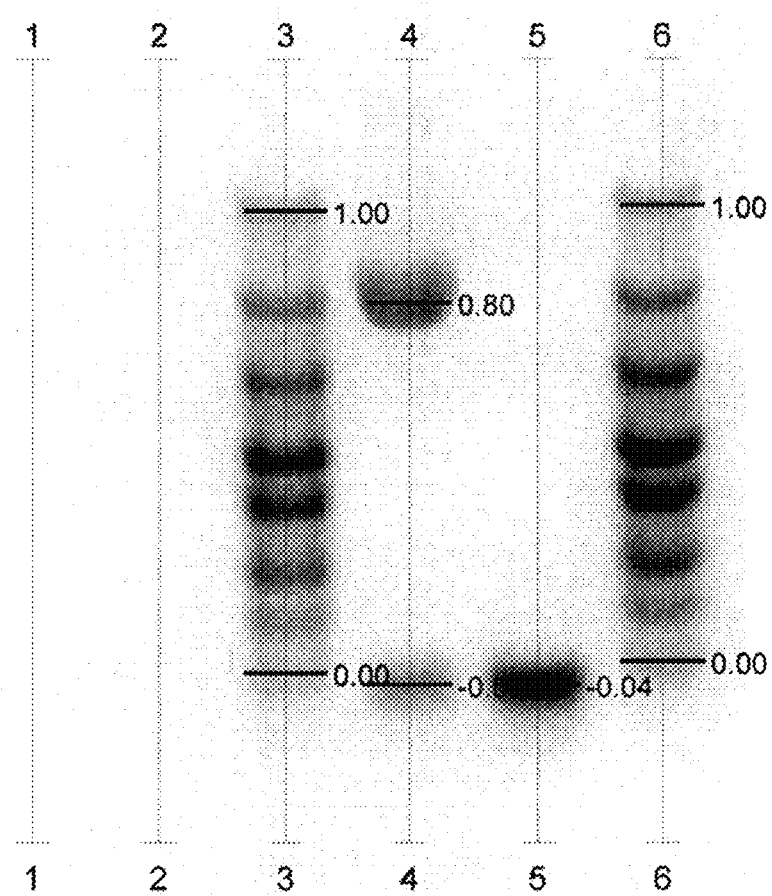
Figure 14:
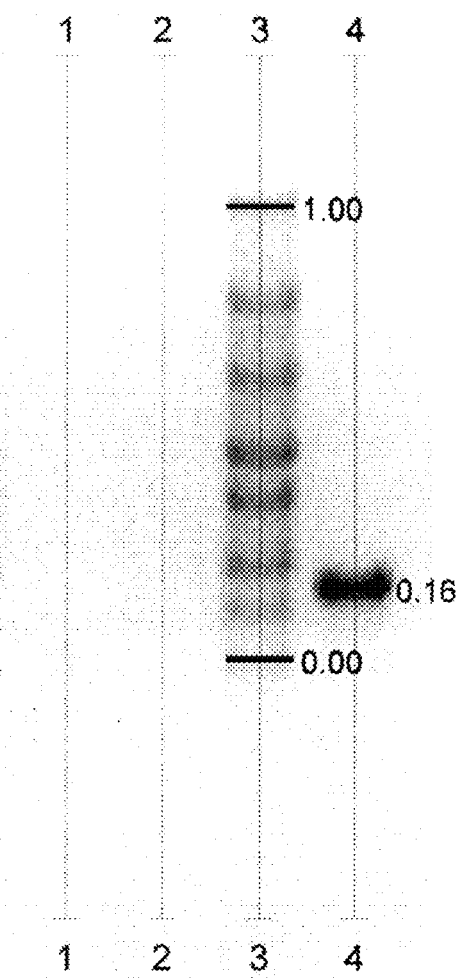
Figure 15:
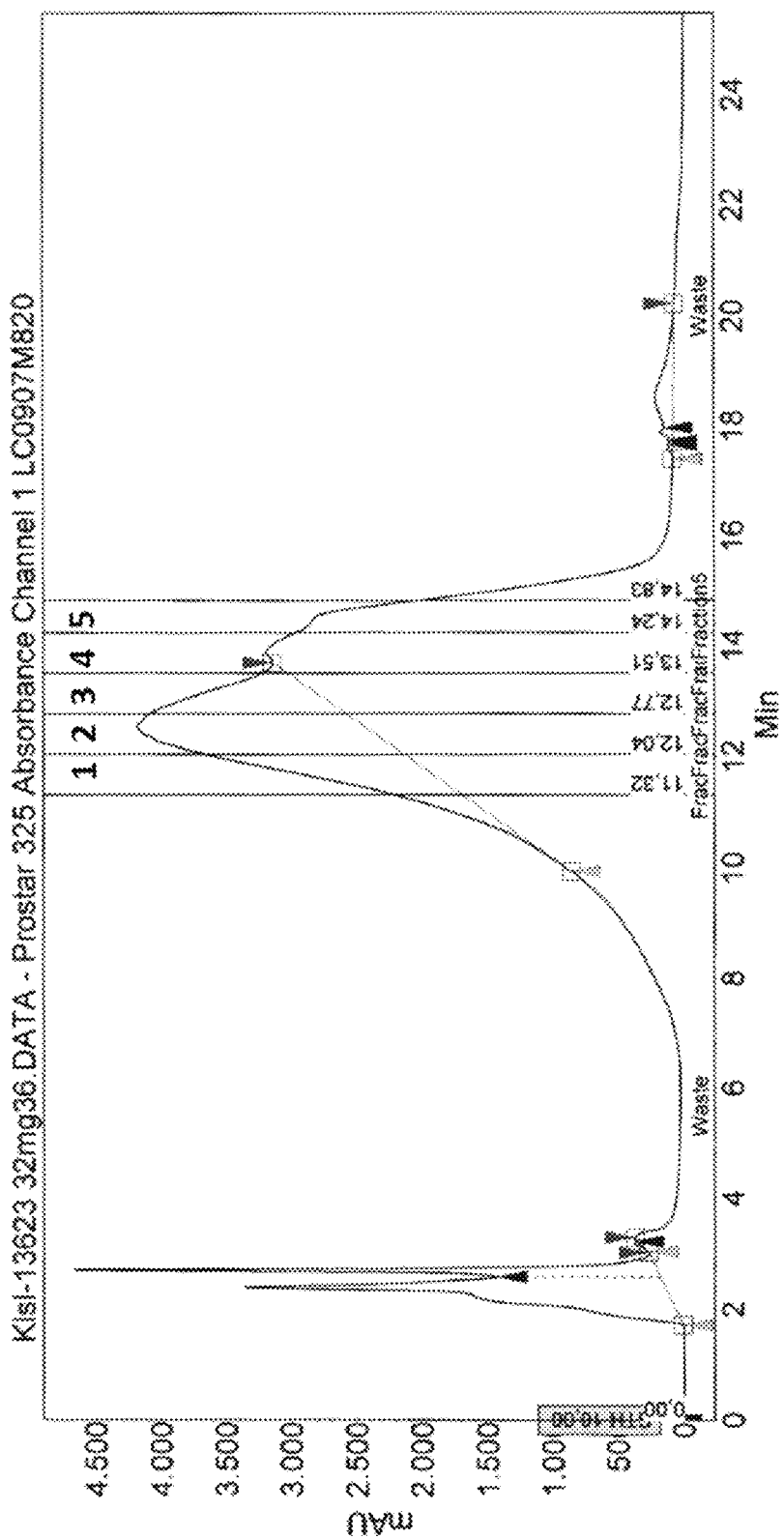
Figure 16:
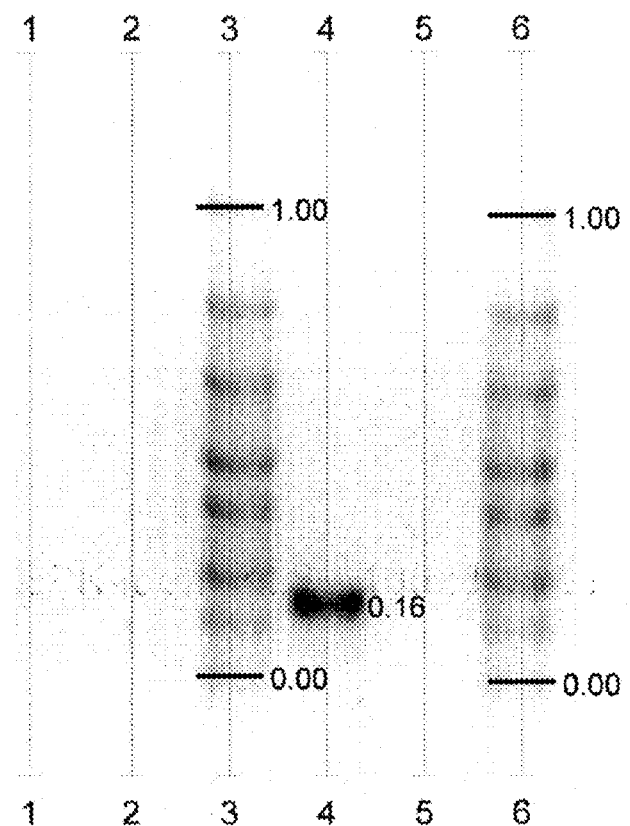
Figure 17:
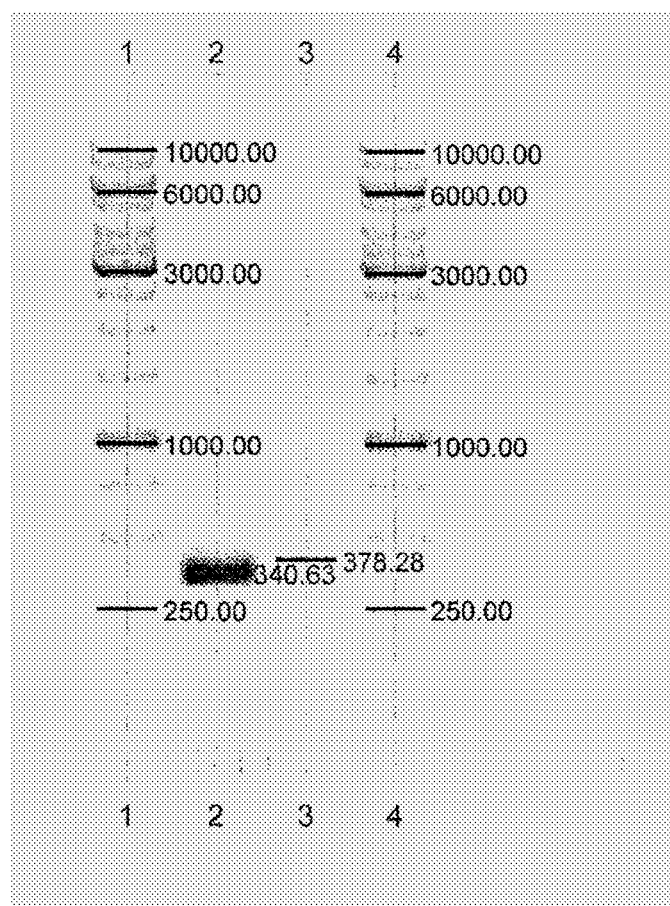

FIG. 1: Schematic overview of the major production steps in an exemplary process.
FIG. 2: Consensus Promoter Sequences (SEQ ID NOs: 4, 5, and 6, as shown top to bottom). The +1 base is the first base incorporated into RNA during transcription. The underline indicates the minimum sequence required for efficient transcription.
FIG. 3: P0361 encoding PpLuc (Photinus pyralis Luciferase).
FIG. 4: Overview of an exemplary process for manufacturing a drug substance comprising RNA.
FIG. 5: Plasmid map of P0624 (P0624-pCV26-HsKLK3(GC)-muag-A64-N5-C30-histoneSL-N5), which was used for RNA production.
FIG. 6: DNA sequence of the nucleic acid sequence encoding the RNA in P0624 (HsKLK3(GC)-muag-A64-N5-C30-histoneSL-N5; SEQ ID NO: 1).
FIG. 7: RNA sequence corresponding to DNA according to SEQ ID NO: 1 (R1869; SEQ ID NO: 2).
FIG. 8: Protein sequence corresponding to RNA according to SEQ ID NO: 2 (SEQ ID NO: 3).
FIG. 9: Gel image of the plasmid DNA test restriction digestion. Agarose gelelectrophoresis of the plasmid DNA test digest, using a DNA ladder gene ruler 1 kb (1), a sample without restriction endonuclease (2), HindIII digestion (3), SpeI digestion (4), EcoRI digestion (5), double digest with HindIII/SpeI (6), double digest with BsrGI/NsiI (7), double digest with BsrGI/HindIII (8), and DNA ladder gene ruler 1 kb (9).
FIG. 10: Gel image of the plasmid DNA test restriction digestion. Agarose gelelectrophoresis of the plasmid DNA test-digest, using a DNA ladder gene ruler 1 kb (1), a sample without restriction endonuclease (2), HindIII digestion (3), SpeI digestion (4), EcoRI digestion (5), double digest with HindIII/SpeI (6), double digest with BsrGI/NsiI (7), double digest with BsrGI/HindIII (8), and DNA ladder gene ruler 1 kb (9).
FIG. 11: Gel image of the plasmid DNA test restriction digestion. Agarose gelelectrophoresis of the plasmid DNA test-digest, using a DNA ladder gene ruler 1 kb (1), a sample without restriction endonuclease (2), HindIII digestion (3), SpeI digestion (4), EcoRI digestion (5), double digest with HindIII/SpeI (6), double digest with BsrGI/NsiI (7), double digest with BsrGI/HindIII (8), and DNA ladder gene ruler 1 kb (9).
FIG. 12: Gel image of the plasmid DNA linearization. Agarose gelelectrophoresis of the plasmid DNA EcoRI digest, using a DNA ladder gene ruler 1 kb (1), EcoRI digested plasmid DNA (2). Size of the DNA ladder is indicated.
FIG. 13: Determination of the reference RNA. Lane 1: control without DNA/RNA; lane 2: empty; lane 3: RNA size ladder; lane 4: reference RNA incubated with linear DNA; lane 5: reference RNA (without DNA).
FIG. 14: Determination of the specific RNA length. Lane 1: negative control; lane 2: empty; lane 3: RNA size ladder; lane 4: RNA product.
FIG. 15: Preparative HPLC—of in vitro transcribed RNA. Exemplary chromatogram of one preparative HPLC run. Product fractions, separated by vertical lines are numbered from 1-5. Fractions were pooled (pool 1: fraction 1; pool 2: fraction 2-3; pool 3: fraction 4-5).
FIG. 16: RNA identity test via RNase treatment. Lane 1: blind control (without RNA); lane 2: empty; lane 3: RNA size ladder; lane 4: RNA product, not treated with RNase; lane 5: RNA product, treated with RNAse A; lane 6: RNA size ladder.
FIG. 17: Agarose gel electrophorese image of the RT-PCR experiment. A photograph of the gel was taken, and the size of the respective bands was determined. Lane 1: DNA ladder gene ruler 1 kb; lane 2: PCR reaction 1; lane 3: PCR reaction 2

EXAMPLES

The Examples shown in the following are merely illustrative and shall describe the present invention in a further way. These Examples shall not be construed to limit the present invention thereto.

Example 1: Sequence of the Template DNA Plasmid

P0624 (P0624-pCV26-HsKLK3(GC)-muag-A64-N5-C30-histoneSL-N5) was used for RNA production. The Figures illustrate the respective plasmid map (FIG. 5), DNA sequence encoding RNA R1869 (SEQ ID NO: 1; FIG. 6), the RNA sequence corresponding to SEQ ID NO: 1 (HsKLK3 (GC)-muag-A64-N5-C30-histoneSL-N5; R1869; SEQ ID NO: 2; FIG. 7) and the corresponding protein sequence (SEQ ID NO: 3; FIG. 8).

Example 2: Restriction Analysis of the Initial Plasmid DNA (QK 1-1)

The identity and quality of the initial plasmid DNA was analyzed using restriction digest. Restriction analysis with one single restriction enzyme (HindIII, SpeI and EcoRI):

1 µl plasmid DNA (1.2 g/l)
1.5 µl 10× reaction buffer
1 µl restriction enzyme (1 U/µl)
11.5 µl WFI (water for injection)
The reaction mix was incubated for 2 h at 37° C.

Restriction analysis with two restriction enzymes (HindIII and SpeI, BsrGI and NsiI, BsrGI and HindIII):

1 µl plasmid DNA (1.2 g/l)
1.5 µl 10× reaction buffer
1 µl restriction enzyme 1 (1 U/µl)
1 µl restriction enzyme 2 (1 U/µl)
10.5 µl WFI (water for injection)
The reaction mix was incubated for 2 h at 37° C.

TABLE 1

Performed restriction enzyme with respective expected band sizes as indicated

| Restriction endonuclease | Expected band size [bp] |
|---|---|
| HindIII | 3040 |
| SpeI | 3040 |
| EcoRI | 3040 |
| HindIII and Spe I | 2243 and 797 |
| BsrGI and NsiI | 2837 and 733 |
| BsrGI and HindIII | 2307 and 733 |

Agarose Gelelectrophoresis:

Samples were prepared for agarose gelelectrophoresis by adding 3 µl of DNA loading dye (6× Orange DNA Loading Dye) to each reaction. Band-separation occurred using a common agarose gelelectrophoresis method. An agarose gel was prepared comprising 0.8 g agarose in 100 ml 1×TBE buffer and 3 µl ethidium bromide. As running buffer, 1×TBE buffer was used. The results are shown in FIG. 9.

Results:

The observed band pattern was in accordance to the theoretically expected pattern (see Table 1).

Example 3: Sequencing of the RNA Coding Region on the Plasmid DNA (QK3-4)

The RNA coding region in the initial plasmid DNA obtained was sequenced with an AB13130XL sequencer, using M13-universal primer: 5'-CGCCAGGGTTTTCCCA-GTCACGAC (SEQ ID NO: 7) and suitable sequence specific primers.

Results:
3'-UTR: sequence correct
ORF: sequence correct
5'-UTR: sequence correct

Example 4: Transformation

Heat-Shock Transformation

For amplification of plasmid DNA in bacteria, the chemically competent bacteria cells (*Escherichia coli* DH5α) were defrosted in the fridge (4° C.). After defrosting, 4 ng of the plasmid DNA solution (P0624, pCV26, insert HsKLK3sl (GC), SEQ ID NO: 1) were added to 50 µl of the competent cells, mixed gently, and incubated for 30 minutes at 4° C. Then, cells were heat-shocked for 20 seconds at 42° C. Following heat shock, cells were put back to 4° C. for 2 minutes. Then, 900 µl pre-warmed (37° C.) LB-bouillon medium without antibiotics was added to the cells and incubated for 1 hour at 37° C. in a shaking incubator (170 rpm).

Then, 10 µl, 100 µl and 800 µl of the sample were plated on LB agar plates containing 100 µg/ml ampicillin and incubated for 16 hours at 37° C. The number of bacterial colonies was counted on each plate (see Table 2). Moreover, plates were inspected for contaminations (e.g., colony shape, colony color, smell).

Results:

TABLE 2

Manual inspection of agar plates

| Volume of plated cells | Number of colonies | Contaminations |
|---|---|---|
| 10 µl | 3 | NO |
| 100 µl | 64 | NO |
| 800 µl | 270 | NO |

Example 5: Fermentation

Inoculation of First Pre-Culture

One bacterial colony of the transformation (see example above) was picked and used to inoculate 5 ml LB-Bouillon containing 100 µg/ml ampicillin as an antibiotic. The first pre-culture was incubated in a 37° C. shaking incubator (170 rpm) for 16 hours.

Inoculation of a Second Pre-Culture 1 ml of the first pre-culture ($OD_{600}$=3.64) was used to inoculate a larger second 50 ml pre-culture and incubated in a 37° C. shaking incubator for 7 hours. 2 ml of the culture were used for determination of cell-density ($OD_{600}$=2.52).

Fermentation Process 48 ml of the second pre-culture were used to inoculate 81 LB medium comprising ampicillin (100 µg/ml) at 37° C. To obtain optimal bacteria growth, feeding solution (LB medium comprising ampicillin (100 µg/ml) with 2% glucose) was constantly fed into the fermenter tank. During fermentation, standard parameters were precisely regulated and continuously monitored (e.g. pH: 7.0, temperature: 37° C.). The cell density was controlled by photometric determination at 600 nm. The fermentation procedure was stopped after 21 hours of incubation time. The final volume of the culture was determined to be 11950 ml, with a cellular density of $OD_{600}$=4.66. After fermentation, 1 ml of the culture was taken for quality control and cells were centrifuged at 11,000 rcf at room temperature for 2 minutes. The supernatant was discarded and the cell pellet was stored at −20° C.

Cell Harvest 11950 ml of bacterial culture (OD600=4.66) were split into 7 different batches (approximately 1707 ml per batch). The bacterial culture batches were spun down at 6000 g for 15 minutes at room temperature, the supernatant was discarded and the cell pellet was frozen at −20° C.

Example 6: Plasmid Preparation (Mini-Preparation)

The mini-preparation was performed using a Mini Plasmid Kit according to the manufacturer's instructions. Following that, the content of dsDNA was determined. The value was used to estimate the total amount of dsDNA produced during the fermentation.

Photometric Determination of the dsDNA Content:

The concentration of the isolated plasmid DNA (dsDNA) was determined by a standard photometric method for nucleic acids via measurement of the absorption at 260 nm (OD260). Measurements were performed in triplicates.

Results:

TABLE 3

Values of the photometric determination of dsDNA in the pDNA sample

| Sample | value 1 [µg/µl dsDNA] | value 2 [µg/µl dsDNA] | value 3 [µg/µl dsDNA] | average [µg/µl dsDNA] |
|---|---|---|---|---|
| Plasmid DNA sample | 0.1915 | 0.1923 | 0.2024 | 0.1954 |

Calculation of the Total Yield of the Fermentation Process:

0.1954 µg/µl*50 µl (volume of plasmid DNA preparation) = 9.77 µg

The culture volume used for the mini preparation was 1 ml. Therefore, 1 ml of bacterial culture contained 9.77 µg plasmid DNA. The expected total plasmid DNA yield of the whole fermentation culture (11.950 ml) is therefore 116752 µg plasmid DNA.

Example 7: Restriction Analysis of the Plasmid DNA Obtained from the Miniprep To analyze the plasmid DNA obtained from the mini preparation (see example above), a test digest using suitable restriction endonucleases was performed according to Example 2.

Results:

The obtained band pattern was in accordance to the theoretically expected pattern (see FIG. 10).

Example 8: Plasmid Giga Preparation

The giga-preparation was performed using an Endotoxin-free plasmid DNA purification kit according to the manufacturer's instructions.

Example 9: Determination of the Plasmid DNA Concentration and OD260/280 (QK3-1)

Plasmid DNA concentration (dsDNA) of the DNA sample obtained from the giga preparation was determined photometrically according to Example 6. The measurements were performed in triplicates. Moreover, the OD 260/280 value was determined, which is a measure for nucleic acid purity.

Results:

TABLE 4

Values of the photometric determination of dsDNA in the pDNA sample

| Sample | value 1 [µg/µl dsDNA] | value 2 [µg/µl dsDNA] | value 3 [µg/µl dsDNA] | average [µg/µl dsDNA] |
|---|---|---|---|---|
| Plasmid DNA | 1.0464 | 1.1077 | 1.0789 | 1.08 |

TABLE 5

Values of the photometric determination of $OD_{260/280}$.

| Sample | value 1 $[OD_{260/280}]$ | value 2 $[OD_{260/280}]$ | value 3 $[OD_{260/280}]$ | average |
|---|---|---|---|---|
| Plasmid DNA | 1.81 | 1.82 | 1.81 | 1.81 |

The concentration of the plasmid DNA preparation was determined to be 1.08 µg/µl. The total yield of the giga-preperation was 30.24 mg.

Moreover, the OD 260/280 value was determined to be 1.81.

Example 10: Determination of RNA Contamination Using RNAse Treatment

Plasmid DNA was checked for RNA contamination. Therefore the plasmid DNA was incubated with RNase A. Afterwards the concentration of the purified plasmid DNA was determined again and the difference before and after RNase treatment was calculated.

Therefore a sample of the plasmid DNA solution obtained from the giga preparation was adjusted to a concentration of 0.4 g/l. Following that, the DNA concentration was determined (dsDNA) photometrically according to Example 6 The measurements were performed in triplicates.

Following that, 38 µl of the plasmid DNA solution were incubated with 1 µl RNase A (1 g/l) and incubated for 1 h at 37° C. The RNAse treated solution was then added on a Sephadex-column to separate nucleotides. After centrifugation at 2000 rpm for 2 minutes, the eluate was used for photometric determination of the DNA content at 260 nm according to Example 6. The values before and after RNAse treatment were used to calculate the percentage of DNA in the sample:

Calculation of the percentage of plasmid DNA contained in the plasmid preparation:

$$\% \text{ plasmid } DNA = \frac{\text{concentration of nucleic acids after } RNase \text{ } A \text{ digestion}}{\text{concentration of nucleic acids before } RNase \text{ } A \text{ digestion}} \times 100\%$$

Results:

TABLE 6

Results of the photometric DNA determination

| Sample | value 1 [μg/μl dsDNA] | value 2 [μg/μl dsDNA] | value 3 [μg/μl dsDNA] | average |
|---|---|---|---|---|
| Before RNase treatment | 0.4262 | 0.4190 | 0.4095 | 0.4182 |
| After RNase treatment. | 0.3921 | 0.3476 | 0.3727 | 0.3708 |

Percentage plasmid DNA: 88.66%

The dsDNA values (in triplicates) are indicated before and after treatment with RNase A. The percentage of plasmid DNA was calculated.

The percentage of plasmid DNA was 88.66%.

Example 11: Test Restriction Digestion of pDNA

To analyze the plasmid DNA obtained from the giga-preparation, a test digest using suitable restriction endonucleases was performed according to Example 2 (see Table 1 for expected band sizes and used enzymes; FIG. 11).

Example 12: Sequencing of the RNA Coding Region on the Plasmid DNA

The RNA coding region in the plasmid DNA obtained from the giga preparation was sequenced with an AB13130XL sequencer, using M13-universal primer: 5'-CGCCAGGGTTTTCCCAGTCACGAC (SEQ ID NO: 7).

Results:
3'-UTR: sequence correct
ORF: sequence correct
5'-UTR: sequence correct

Example 13: Determination of the Bacterial Endotoxin Level in the Plasmid DNA Solution Plasmid DNA solution (0.5 g/l) was analysed for bacterial endotoxin content (expressed as endotoxin units, EU) using the LAL-test (kinetic-turbidimetric method) according to Ph. Eur., 7th Edition, 2.6.14.

Result:
The endotoxin value of the plasmid DNA solution was determined to be <0.2 EU/ml.

Example 14: Determination of Protein Contamination in the Plasmid DNA Solution To determine the protein contamination in the plasmid DNA, a commercially available Bradford test and/or BCA-test was used. The test was performed according to the manufacturer's instructions.

Photometric Determination of Protein Contamination:
The measurements were performed in a standard photometer, using UV cuvettes. The measurements were performed in duplicates per sample (standards and plasmid DNA sample) at 595 nm (Bradford) or 562 nm (BCA). The protein concentration in the plasmid DNA sample was determined using a BSA standard curve.

Results:

TABLE 7

Results of the OD measurement of the plasmid DNA.

| Plasmid DNA probe | OD Value 1 | OD Value 2 | OD average | OD average corrected | Sample dilution factor | $C_{protein}$ [μg/ml] |
|---|---|---|---|---|---|---|
| 0 | 0.262 | 0.187 | 0.225 | 0.056 | 1 | 1.6 |

The respective OD value of the plasmid DNA sample was determined twice, and an average was calculated. The OD value was used to determine the protein contamination in the sample, using a standard curve.

The protein contamination in the plasmid DNA sample was determined to be 1.6 μg/ml.

Example 15: Determination of the Bioburden in the Plasmid DNA Sample Using a Plate Count Method For determination of the bioburden, the presence of bacteria was tested under aerobic or anaerobic conditions after plating the plasmid DNA on agar and glucose plates and incubating the plates for 5 and 7 days, using a plate count method (according to PhEur 2.6.12.).

The bioburden is typically monitored by counting the growth of bacteria clones/colonies (colony forming units (CFU)) on bacteria agar plates over a certain timespan. For this purpose, soybean casein digest agar (CSA) and sabouraud glucose (2%) agar plates were prepared. 100 μl of plasmid DNA were plated on respective agar plates under sterile conditions and incubated at approximately 22° C. (SG, Sabouraud Glucose plates) or at 32° C. under aerobic or anaerobic conditions (CSA plates).

Results:

TABLE 8

Results of the plate count assay

| | Day 2 CFU | Day 5 CFU | Day 6 CFU | Day 7 CFU |
|---|---|---|---|---|
| Plate ID 1 | 2 | 2 | | |
| Plate ID 2 | 9 | 14 | | |
| Plate ID 3 | | 1 | 1 | 1 |

The plate count assay resulted in the indicated numbers of CFUs.

In total, 17 CFUs were counted after plating 100 μl of plasmid DNA solution on the respective agar plates, grown under conditions explained above The bioburden of the plasmid DNA solution was therefore 1.7 CFU/ml.

Example 16: Determination of Residual E. coli DNA by Quantitative PCR

Quantitative PCR was performed to determine the contamination with genomic Escherichia coli DNA. For this purpose the E. coli specific gene uidA was amplified and quantified using a LightCycler qPCR thermocycle (Roche).

The following probes and primers were used in the experiment:

```
Primer EC 679U:
GGACAAGGCACTAGCG              (SEQ ID NO: 8)

Primer EC 973 L:
ATGCGAGGTACGGTAGGA            (SEQ ID NO: 9)

Probe EC1 FL:
CATCCGGTCAGTGGCAGT-FL         (SEQ ID NO: 10)

Probe EC1 LC:
LC640-AAGGGCGAACAGTTCCTGA-ph  (SEQ ID NO: 11)
```

Results:

The quantitative PCR determined an *E. coli* copy number of 281 in 10 μg of the plasmid DNA preparation. This results in an *E. coli* copy number of 28.1 per μg plasmid DNA.

Example 17: Linearization of the Plasmid DNA

To generate a linear template DNA for enzymatic RNA in vitro transcription, plasmid DNA obtained by giga-preparation (see Example 8) was linearized using restriction endonuclease EcoRI.

Plasmid DNA Linearization:

27.5 ml plasmid DNA [1.08 mg/ml], 9 ml EcoRI restriction enzyme [10 U/μl], 15 ml 10× restriction buffer and 98.5 ml WFI (water for injection) were mixed and divided evenly into 6 reactions. The reactions were incubated for 4 hours at 37° C.

Plasmid DNA Extraction 17.5 ml phenol/chloroform/isoamylalcohol (25/24/1) were added to each reaction and mixed by vortexing for 5 minutes. Subsequently, the reactions were centrifuged at 3000 rcf at 10° C. for 10 minutes. The upper aqueous phase of the reaction was carefully transferred to a new reaction tube.

Plasmid DNA Precipitation 17.5 ml isopropyl alcohol was added to each reaction, mixed by vortexing for 10 seconds, and centrifuged for 60 minutes at 3000 rcf. The supernatant was discarded.

DNA pellets were washed with 10 ml ethanol (75%) for 10 minutes at 3000 rcf. After discarding the supernatant, the pellets were centrifuged again (1 minute) and residual ethanol was carefully removed with a pipette.

Re-Suspension of DNA

DNA pellets were dissolved in 5 ml WFI each. The six separate samples were pooled and used for photometric determination of dsDNA via measurement of the absorption at 260 nm (OD260) (final volume: 30 ml).

TABLE 9

Photometric determination of the dsDNA content

| Sample | value 1 [μg/μl dsDNA] | value 2 [μg/μl dsDNA] | value 3 [μg/μl dsDNA] | average [μg/μl dsDNA] |
|---|---|---|---|---|
| linearized DNA | 0.77 | 0.77 | 0.76 | 0.767 |

The total amount of linearized dsDNA was (0,767 mg/ml*30 ml)=23.01 mg.

Example 18: Determination of the Linearization Quality Via Agarose Gelelectrophoresis To analyze the quality of the restriction digest, linearized template DNA was analyzed via agarose gel electrophoresis. The result is shown in FIG. 12.

Result: A complete linearization of the plasmid DNA could be detected by agarose gelelectrophoresis.

Example 19: Test for RNase Contamination of the Linear DNA Template

To test the obtained linear DNA template for RNase contamination, a reference RNA molecule was incubated with the linear DNA template.

2 μl RNA reference (RNA R488, expected size 507 bases) were incubated with 6 μl linear DNA (concentration adjusted to 0.5 g/l), and 2 μl RNA reference with 6 μl WFI as a negative control were incubated for 1 hour at 37° C.

Subsequently, the samples were analyzed using RNA gel electrophoresis.

RNA Agarose Gel Electrophoresis:

A 50 ml RNA gel (1.2%) was prepared to determine the presence of the reference RNA. 0.6 g agarose and 5 ml 10×MOPS buffer (20 mM EDTA, 200 mM MOPS, 50 mM sodium acetate pH 7.0) were added to 45 ml water and incubated at 65° C. for 15 minutes. After agarose had been completely dissolved, 0.9 mL formaldehyde solution (37%) were added, and the liquid was poured into a horizontal gel-chamber. After the gel solidified, RNA running buffer was added to the gel chamber (lx MOPS buffer, 0.74% formaldehyde).

The RNA samples and 10 μl of an RNA size ladder (500-6000b; single RNAs in the size of 492, 742, 992, 1490, 1992, 2991, 3964, and 6001 b, 1 μg/ml) were substituted with 2 μl gel loading buffer and were run on the agarose gel (FIG. 13).

Results:

TABLE 10

Summary and analysis of the test for RNA contamination

| Integrity values | |
|---|---|
| Integrity of RNA incubated with DNA ($IN_P$) | 84.0% |
| Integrity of RNA negative control ($IN_C$) | 89.2% |
| Relative Difference ($IN_P$ − $IN_C$)/$IN_C$ | 5.8% |
| Specific length | |
| Specific length of the RNA, incubated with DNA ($SL_P$) | −0.03 |
| Specific length of RNA negative control ($SL_C$) | −0.04 |
| Absolute Difference ($SL_P$ − $SL_C$) | 0.01 |

The incubation of a reference RNA with the linear plasmid DNA resulted in an integrity of 84% compared to an integrity of 89.2% of the control RNA and therefore was applicable for in vitro transcription.

Example 20: Large-Scale RNA In Vitro Transcription

A large scale in vitro RNA transcription reaction using the linear template DNA was conducted.

RNA In Vitro Transcription 29.7 ml linear template DNA [0.77 g/l], 92 ml Cap/NTP-mix (20 mM ATP, 20 mM CTP, 20 mM UTP, 7.25 mM GTP, 29 mM m7G(5')ppp(5')G-Cap-analog, 92 ml 5× transcription buffer (containing 400 mM HEPES, 120 mM MgCl$_2$, 10 mM spermidine, 200 mM DTT, 25 U/ml inorganic pyrophosphatase), 2.3 ml RNase inhibitor [40 U/µl], 11.5 ml T7 RNA polymerase [200 U/µl] and 232.5 ml WFI were gently mixed and divided to 36 different 50 ml reaction tubes. The reactions were incubated at 37° C.

DNA Template Removal: DNase I Treatment

To digest DNA template, 3.83 ml DNase I [1 U/µl] and 127 µl 0.1M $CaCl_2$ were added to each reaction tube (36 reactions in total) and incubated at 37° C.

Precipitation of RNA

After DNase digest, 15.33 ml WFI and 15.97 ml 8M $LiCl_2$ were added to the reaction and well mixed via vortexing for 15 seconds. The 36 reactions were incubated over night at −20° C. and subsequently centrifuged at 4° C. The supernatant was discarded, and the RNA pellets were washed with 10 ml 75% ethanol and centrifuged for 10 minutes at 4° C. The supernatant was discarded, and the RNA pellets were again washed with 10 ml 75% ethanol and centrifuged for 1 minute. After discarding the supernatant, the remaining ethanol was carefully removed with a pipette. Following that, the RNA pellets were dried at room temperature.

Re-Suspension of RNA

Each dried RNA pellet was re-suspended in 10 ml WFI. Following that, the 36 reactions were pooled. The RNA concentration of the sample was determined photometrically (Table 11).

Results:

TABLE 11

Photometric determination of the RNA concentration

| Sample | value 1 [µg/µl RNA] | value 2 [µg/µl RNA] | value 3 [µg/µl RNA] | average [µg/µl RNA] |
|---|---|---|---|---|
| RNA | 2.1 | 2.1 | 2.1 | 2.1 |

Measurements were performed in triplicates, and average was calculated.

The RNA concentration of the solution was determined to be 2.1 µg/µl. Therefore, the total yield of the large-scale RNA in vitro transcription (360 ml volume) reaction was 756 mg.

Example 21: Analysis of the In Vitro Transcribed RNA (Large-Scale Reaction) by Agarose Gel Electrophoresis The size and the band uniqueness of the in vitro transcribed RNA were determined by performing RNA agarose gel electrophoresis according to Example 19).

Result:

The determined RNA length was in accordance with the expected length (see FIG. 14). Moreover, no additional band was observed.

Example 22: Preparative HPLC Purification of In Vitro Transcribed RNA

The in vitro transcribed RNA was purified by a size-selective HPLC based technique as described in WO2008077592. The purified RNA was concentrated by alcohol precipitation and re-suspended in water for injection. The concentration of the RNA was determined by photometry.

Preparative HPLC:

A porous, nonalkylated polystyrene/divinylbenzene (polystyrenedivinylbenzene) matrix was used (PLRP-S 4000 Å 8 µm 50×25 mm column) as a stationary phase. The column had a particle size of 8 µm and a pore size of 4000 Å.

The eluent buffers, eluent A (100 mM triethylammonium acetate in WFI, pH 7.0) and eluent B (100 mM Triethylammoniumacetat in 25% acetonitrile, pH 7.0), were de-gassed with helium. 360 ml of a 2.1 mg/ml RNA solution obtained from the large-scale in vitro RNA transcription and 40 ml of 1M triethylammonium acetate (TEAA) were mixed. The RNA was step-wise purified and fractionated. The HPLC fractions were collected, and the product-containing fractions (fractions 1-5 in FIG. 15) were pooled.

Detection proceeded with an UV detector at 254 nm with a reference measurement at 600 nm.

Pool 1: fraction 1
Pool 2: fraction 2-3
Pool 3: fraction 4-5

All 3 product pools were used for precipitation, freeze-drying (lyophilization) and subsequent quality controls.

The RNA lyophilisate was re-suspended in WFI to obtain a final RNA concentration of approximately 5.0 g/l. Following that, RNA solution was sterile-filtered.

Determination of the RNA Concentration:

The RNA concentration of the RNA was determined photometrically according to Example 20 to be 4.80 g/l. Therefore, the total yield of the large scale in vitro transcription, after purification was 458.4 mg.

End-Product Controls

Example 23: RNA Identity Test Using RNase a Treatment

To determine the identity of the product, 8 µl WFI and 1 µg (1 µg/µl) RNA were treated with 1 µl RNase A (10 µg/µl). Additionally, one untreated control was prepared (1 µl RNA (1 µg/µl and 9 µl WFI). Both reactions were incubated for 1 h at 37° C. and subsequently analyzed via conventional RNA gel electrophoresis according to Example 21.

The results are shown in FIG. 16.

Results:

As can be seen from FIG. 18, no RNA band is detectable in the sample with RNAse treatment.

Example 24: RNA Identity Test Using RT-PCR

RNA identity was determined by RT-PCR (Reverse transcription PCR) using M-MuLV Reverse Transcriptase for cDNA generation by reverse transcription and a conventional PCR using gene-specific primers (primer pair I: 204-AS-FW+205-AS-RV; 799-AS-FW and 792-AS-RV).

Reverse Transcription:

2 µl RNA (50 ng/µl) were added to 9 µl WFI and 1 µl oligo dT Primer $(dT)_{18}$ (5 pmol/µl) and incubated for 5 min at 65° C. in a heating block and subsequently put on ice. 4 µl 5× reaction buffer, 1 µl RNase inhibitor (20 U/µl), 2 µl dNTP mix (10 mM) and 1 µl M-MuLV Reverse Transcriptase (200 U/µl) were added, mixed and incubated for 60 min at 42° C. The reaction was stopped by incubation at 70° C. for 5 min. Subsequently, the reaction was cooled on ice.

PCR:

2 µl of the RT reaction were added to 25 µl 2×PCR Master Mix, 5 µl Forward-Primer (5 pmol/µl), 5 µl Reverse-Primer (5 pmol/µl), 11.5 µl WFI and 1.5 µl DMSO (100%).

Primer Pair I for PCR Reaction 1:

```
Forward-Primer 204-AS-FW:
CACTGCATCCGGAACAAG        (SEQ ID NO: 16)

Reverse-Primer 205-AS-RV:
CACGTCGTTGCTGATCAC        (SEQ ID NO: 17)
```

Primer Pair II for PCR Reaction 2:

```
Forward-Primer 799-AS-FW:
CCAGAAGGTGACCAAGTTCA      (SEQ ID NO: 18)

Reverse-Primer 792-AS-RV:
GCTCTGAAAAGAGCCTTTGG      (SEQ ID NO: 19)
```

PCR Program for PCR 1:

| Cycles | Temperature | Time [min:s] |
|---|---|---|
| 1 | 95° C. | 2:00 |
| 30 | 95° C. | 0:30 |
|  | 55° C. | 0:30 |
|  | 72° C. | 0:30 |
|  | 72° C. | 10:00 |
| 1 | 4° C. | ∞ |

PCR Program for PCR 2:

| Cycles | Temperature | Time [min:s] |
|---|---|---|
| 1 | 95° C. | 2:00 |
| 35 | 95° C. | 0:30 |
|  | 55° C. | 0:30 |
|  | 72° C. | 0:30 |
|  | 72° C. | 10:00 |
| 1 | 4° C. | ∞ |

The results of the PCR reactions were analysed by DNA gel electrophoresis according to Example 2. The results are shown in FIG. 17.

Results:

| | | |
|---|---|---|
| PCR reaction 1: | expected size: 357 bp | determined size: 341 bp |
| PCR reaction 2: | expected size: 412 bp | determined size: 378 bp |

Example 25: RNA Identity and Integrity Test Via RNA-Gel Electrophoresis

Size, band uniqueness, and integrity of the pure RNA pools was determined by performing RNA agarose gel electrophoresis according to Example 21. Results are shown in Table 12.

TABLE 12

Results of the RNA agarose gel electrophoresis

| | Additional bands visible? | Band Intergity |
|---|---|---|
| Pure RNA | No | 82.7 |

Results:
For the pure RNA, no additional band was determined. Moreover band integrity met the quality requirements.

Example 26: Photometric Determination of the RNA Content

The RNA concentration of the pure RNA sample was again determined photometrically according to Example 20.

Results:
The RNA concentration of the pure RNA sample was determined to be 5.1 g/l.

Example 27: Determination of the pH

Potentiometric determination of the pH content was performed using a commercially available volt-meter according to the European pharmacopedia (PhEur) 2.2.3.

Results:
The pH of the RNA solution was determined to be 6.43.

Example 28: Determination of the Osmolality

The measurement of the osmolality was performed according to European pharmacopedia (PhEur) 2.2.35, using a commercially available osmometer.

Results:
The osmolality was determined to be 3.7 mOsmol/kg.

Example 29: Determination of Sterility/Bioburden Using a Plating Assay

For determination of the bioburden the presence of bacteria was tested under aerobe and anaerobe conditions after plating the RNA to agar- and glucose plates and incubation for 5 and 7 days, using a plate count method (according to PhEur 2.6.12.). The – test was performed according to Example 15.

Example 30: Determination of the Endotoxin Content of the Pure RNA

For determination of the endotoxin levels the LAL-test (kinetic-turbidimetric method) according to Ph. Eur., 7th Edition, 2.6.14. was performed.

Results:
The endotoxin-level of the pure RNA was determined to be 0.25 EU/ml.

Example 31: Determination of the Protein Content of the Pure RNA

The protein content of the pure RNA sample was determined according to Example 14.

Results:
The protein content was determined to be 2.4 µg/ml.

Example 32: Determination of Residual Plasmid DNA

Residual plasmid DNA was detected via quantitative PCR using specific primers and probes for the ampicillin gene hosted in the production vector. Quantitative PCR to determine the contamination with template pDNA was performed using a LightCycler and LightCycler Master Mix (Roche Diagnostics) according to the manufacturer's instructions.

The following primers and probes were used:

```
Sense-Primer bla13U:
GATACCGCGAGACCCAC                    (SEQ ID NO: 12)

Antisense-Primer bla355L:
GGAACCGGAGCTGAATG                    (SEQ ID NO: 13)

Probe BL04FL:
GCCAGCCGGAAGGGCC-FL                  (SEQ ID NO: 14)

Probe BL04LC:
LC Red640-GCGCAGAAGTGGTCCTGCA-Ph     (SEQ ID NO: 15)
```

Results:
The copy number of pDNA in the RNA was determined to be 2.5 E+03 copies/µg RNA.

Example 33: Determination of Residual Genomic Bacteria DNA

Residual bacterial genomic DNA was determined according to Example 16.

Results:
Genomic DNA of E. coli was undetectable in the RNA sample.

Example 34: Determination of Residual Solvents

The determination of residual solvents in the RNA was determined using quantitative gas-chromatography with flame ionization detector (GC-FID).

Results:

TABLE 13

| Residual solvents as detected by quantitative GC. | |
|---|---|
| Solvent | Detected by GC-FID |
| TEAA | 43 ppm |
| Isopropanol | <50 ppm |
| Chlorophorm | <60 ppm |
| Acetonitrile | <40 ppm |
| Phenol | <20 ppm |

---

The invention claimed is:

1. A method for producing purified mRNA on a preparative scale comprising the following steps:
   a) providing a template DNA comprising a nucleic acid sequence encoding a mRNA sequence;
   b) in vitro transcription of the template DNA in order to obtain a composition comprising the mRNA;
   c) purification of a preparative quantity of the mRNA obtained in step b) by purification steps comprising, at least:
      i) oligo dT-based affinity purification; and
      ii) RP-HPLC,
   thereby producing a preparative quantity of purified mRNA.

2. The method of claim 1, wherein the oligo dT-based affinity purification is performed before the RP-HPLC.

3. The method of claim 1, wherein the RP-HPLC is performed before the oligo dT-based affinity purification.

4. The method of claim 1, wherein the RP-HPLC is performed on a PLRP-S column.

5. The method of claim 1, wherein the following steps are used to control the quality of the template DNA provided in step a):
   I) determining the concentration of the template DNA in a sample;
   II) determining the integrity of the template DNA;
   III) determining the identity of the template DNA; and/or
   IV) determining the purity of the template DNA.

6. The method of claim 1, wherein the following steps are used to assess the quality of the mRNA obtained in steps b) or c):
   i) determining the concentration of the mRNA or the purified mRNA in a sample;
   ii) determining the integrity of the mRNA or the purified mRNA;
   iii) determining the identity of the mRNA or the purified mRNA;
   iv) determining the purity of the mRNA or the purified mRNA;
   v) determining the pH of a sample comprising the mRNA or the purified mRNA;
   vi) determining the osmolality of a sample comprising the mRNA or the purified mRNA;
   vii) determining the presence and/or the amount of the template DNA in a sample comprising the mRNA or the purified mRNA; and/or
   viii) determining the presence and/or the amount of an organic solvent in a sample comprising the mRNA or the purified mRNA.

7. The method of claim 1, wherein the purified mRNA obtain in step c) comprises 1 to 5 grams of mRNA.

8. The method of claim 1, wherein step a) comprises synthesis of the template DNA.

9. The method of claim 1, wherein the template DNA is a DNA plasmid.

10. The method of claim 1, wherein the in vitro transcription in step b) is carried out in presence of modified nucleotides.

11. The method of claim 1, wherein the purification in step c) further comprises a precipitation step.

12. The method of claim 11, wherein the precipitation step is an alcoholic precipitation step or a LiCl precipitation step.

13. The method of claim 1, wherein the purification in step c) comprises a further chromatographic step selected from the group consisting of anion exchange chromatography, affinity chromatography, hydroxyapatite chromatography and core bead chromatography.

14. The method according to claim 11, wherein the precipitation step if before the RP-HPLC.

15. The method according to claim 14, wherein the precipitation step comprises LiCl precipitation.

16. The method according to claim 1, wherein the mRNA obtained in step b) or the purified mRNA obtained in step c) is lyophilized.

* * * * *